US008802106B2

(12) United States Patent
Melnik et al.

(10) Patent No.: US 8,802,106 B2
(45) Date of Patent: Aug. 12, 2014

(54) PEPTIDE COMPOSITIONS AND METHODS FOR INHIBITING HERPESVIRUS INFECTION

(75) Inventors: Lilia I. Melnik, New Orleans, LA (US); Robert F. Garry, New Orleans, LA (US); Cindy A. Morris, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 13/505,099

(22) PCT Filed: Oct. 29, 2010

(86) PCT No.: PCT/US2010/054743
§ 371 (c)(1),
(2), (4) Date: Aug. 20, 2012

(87) PCT Pub. No.: WO2011/053798
PCT Pub. Date: May 5, 2011

(65) Prior Publication Data
US 2013/0005648 A1    Jan. 3, 2013

Related U.S. Application Data
(60) Provisional application No. 61/280,112, filed on Oct. 30, 2009.

(51) Int. Cl.
C07K 14/045    (2006.01)
A61P 31/22     (2006.01)
A61K 39/245    (2006.01)
C07K 14/005    (2006.01)
A61K 39/00     (2006.01)
A61K 38/00     (2006.01)

(52) U.S. Cl.
CPC ............ C07K 14/045 (2013.01); *A61K 39/245* (2013.01)
USPC ..................................................... 424/186.1

(58) Field of Classification Search
CPC .... C07K 14/045; C07K 14/005; A61P 31/22; A61K 39/245; A61K 39/00; A61K 38/00
USPC ..................................................... 424/186.1
See application file for complete search history.

(56) References Cited

U.S. PATENT DOCUMENTS

| 5,464,933 | A |   | 11/1995 | Bolognesi et al. |       |
|-----------|---|---|---------|------------------|-------|
| 5,514,577 | A |   | 5/1996  | Draper et al.    |       |
| 5,633,230 | A | * | 5/1997  | Twist et al.     | 514/3.7 |
| 5,831,001 | A |   | 11/1998 | Twist et al.     |       |
| 2004/0091852 | A1 | * | 5/2004 | Agut et al. | 435/5 |
| 2004/0209241 | A1 | * | 10/2004 | Hermanson et al. | 435/5 |
| 2005/0260199 | A1 |   | 11/2005 | Compton et al. |  |
| 2006/0160177 | A1 | * | 7/2006 | Okkels et al. | 435/69.1 |
| 2009/0181889 | A1 |   | 7/2009 | Dewhurst et al. |  |

FOREIGN PATENT DOCUMENTS

| CN | 101780277 A | 7/2010 |
| WO | 8907143 A1 | 8/1989 |
| WO | 9531555 A1 | 11/1995 |
| WO | 99-01464 | 1/1999 |
| WO | 03000720 A1 | 1/2003 |

OTHER PUBLICATIONS

Navarro, et al., "Humoral immune response to functional regions of human cytomegalovirus glycoprotein B," J. Med. Virol. 52:451-459 (1997.*
Varnum, S.M. et al., Identification of Proteins in Human Cytomegalovirus (HCMV) Particles: The HCMV Proteome, Journal of Virology 78 (20), 10960-10966 (2004).
Lopper, M. et al., Disulfide Bond Configuration of Human Cytomegalovirus Glycoprotein B, Journal of Virology 76 (12), 6073-6082 (2002).
Bold, S. et al., Structural Domains Involved in Human Cytomegalovirus Glycoprotein B-Mediated Cell—Cell Fusion, Journal of General Virology 77, 2297-2302 (1996).
Keay, S. et al., Anti-Idiotype Antibodies That Mimic gp86 of Human Cytomegalovirus Inhibit Viral Fusion But Not Attachment, Journal of Virology 65 (9), 5124-5128 (1991).
Navarro D. et al., Glycoprotein B of Human Cytomegalovirus Promotes Virion Penetration Into Cells, Transmission of Infection From Cell to Cell, and Fusion of Infected Cells, Virology 197, 143-158 (1993).
Tugizov S. et al., Mutated Forms of Human Cytomegalovirus Glycoprotein B Are Impaired in Inducing Syncytium Formation, Virology 209, 580-591 (1995).
Hrobowski, Y.M. et al., Peptide Inhibitors of Dengue Virus and West Nile Virus Infectivity, Virology Journal 2, 49-59 (2005).
Sainz Jr., B. et al., Inhibition of Severe Acute Respiratory Syndrome-Associated Coronavirus (SARS-CoV) Infectivity by Peptides Analogous to the Viral Spike Protein, Virus Research 120, 146-155 (2006).
Lambert, D.M. et al., Peptides From Conserved Regions of Paramyxovirus Fusion (F) Proteins are Potent Inhibitors of Viral Fusion, Proc. Natl. Acad. Sci. USA 93 (5) 2186-2191 (1996).
Pass, "Development and evidence for efficacy of CMV glycoprotein B vaccine" J. Clin. Virology; 2009; 46:S73-S76.
UniProt Database Protein Sequence Accession No. Q9WMX1, Nov. 1, 1999.

* cited by examiner

*Primary Examiner* — Christina Bradley
*Assistant Examiner* — Kristina M Hellman
(74) *Attorney, Agent, or Firm* — Olson & Cepuritis, Ltd.

(57) ABSTRACT

The present invention provides an isolated peptide having an amino acid residue sequence that comprises at least one human cytomegalovirus glycoprotein B (HCMV-gB) sequence segment, each HCMV-gB sequence segment consisting of at least 8 and not more than 60 consecutive amino acid residues from residues 146 to 315, residues 476 to 494 of SEQ ID NO: 1, or from a sequence variant of residues 146 to 315 or 476 to 494 of SEQ ID NO: 1 that has at least 70% sequence identity thereto. The peptides of the invention are useful for treating, preventing, or inhibiting a herpesvirus (e.g., Herpes Simplex Virus-1, Human Cytomegalovirus, and the like) infection in a subject.

2 Claims, 18 Drawing Sheets

A

Figure 2A:
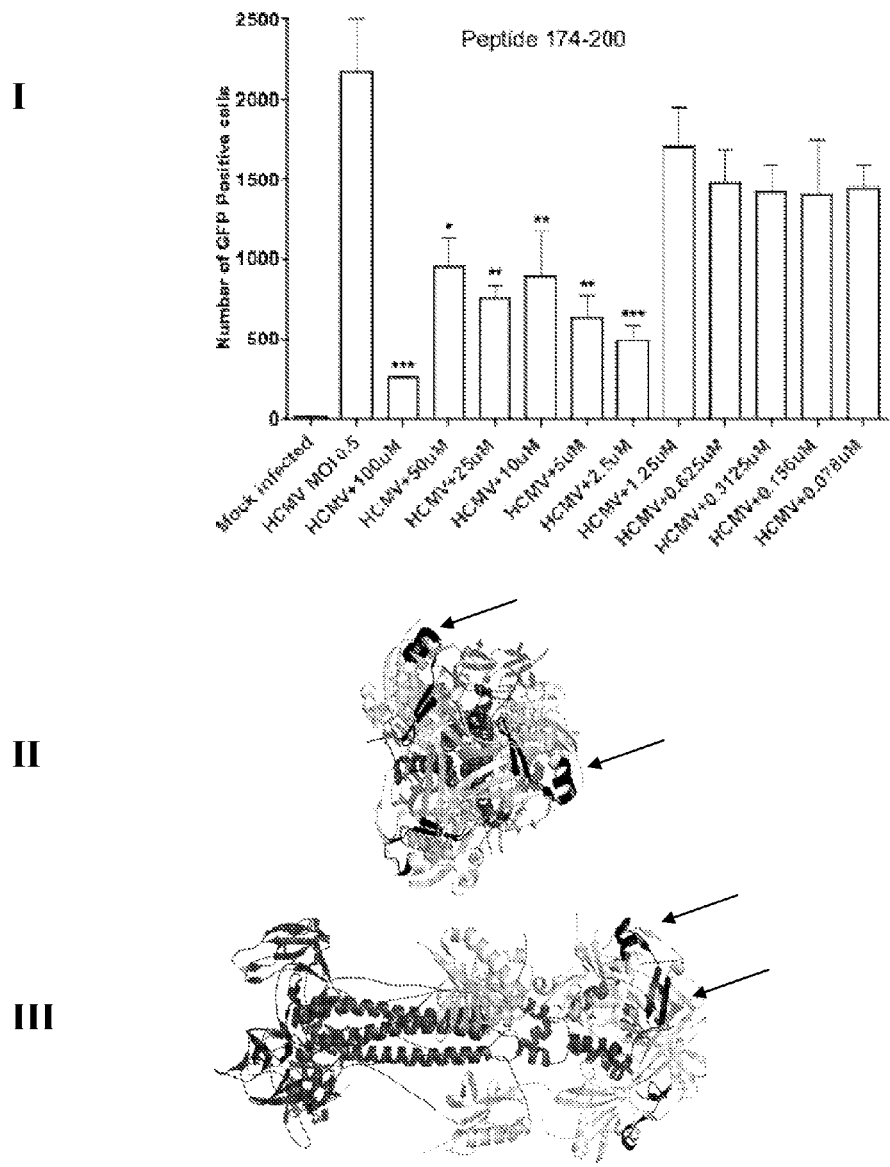

```
1    MESRIWCLVV CVNLCIVCLG AAVSSSSTSH ATSSTHNGSH TSRTTSAQTR SVYSQHVTSS
61   EAVSHRANET IYNTTLKYGD VVGVNTTKYP YRVCSMAQGT DLIRFERNII CTSMKPINED
121  LDEGIMVVYK RNIVAHTFKV RVYQKVLTFR RSYAYIYTTY LLGSNTEYVA PPMWEIHHIN
181  KFAQCYSSYS RVIGGTVFVA YHRDSYENKT MQLIPDDYSN THSTRYVTVK DQWHSRGSTW
241  LYRETCNLNC MLTITTARSK YPYHFFATST GDVVYISPFY NGTNRNASYF GENADKFFIF
301  PNYTIVSDFG RPNAAPETHR LVAFLERADS VISWDIQDEK NVTCQLTFWE ASERTIRSEA
361  EDSYHFSSAK MTATFLSKKQ EVNMSDSALD CVRDEAINKL QQIFNTSYNQ TYEKYGNVSV
421  FETSGGLVVF WQGIKQKSLV ELERLANRSS LNITHRTRRS TSDNNTTHLS SMESVHNLVY
481  AQLQFTYDTL RGYINRALAQ IAEAWCVDQR RTLEVFKELS KINPSAILSA IYNKPIAARF
541  MGDVLGLASC VTINQTSVKV LRDMNVKESP GRCYSRPVVI FNFANSSYVQ YGQLGEDNEI
601  LLGNHRTEEC QLPSLKIFIA GNSAYEYVDY LFKRMIDLSS ISTVDSMIAL DIDPLENTDF
661  RVLELYSQKE LRSSNVFDLE EIMREFNSYK QRVKYVEDKV VDPLPPYLKG LDDLMSGLGA
721  AGKAVGVAIG AVGGAVASVV EGVATFLKNP FGAFTIILVA IAVVIITYLI YTRQRRLCTQ
781  PLQNLFPYLV SADGTTVTSG STKDTSLQAP PSYEESVYNS GRKGPGPPSS DASTAAPPYT
841  NEQAYQMLLA LARLDAEQRA QQNGTDSLDG QTGTQDKGQK PNLLDRLRHR KNGYRHLKDS
```

(SEQ ID NO: 1)

B

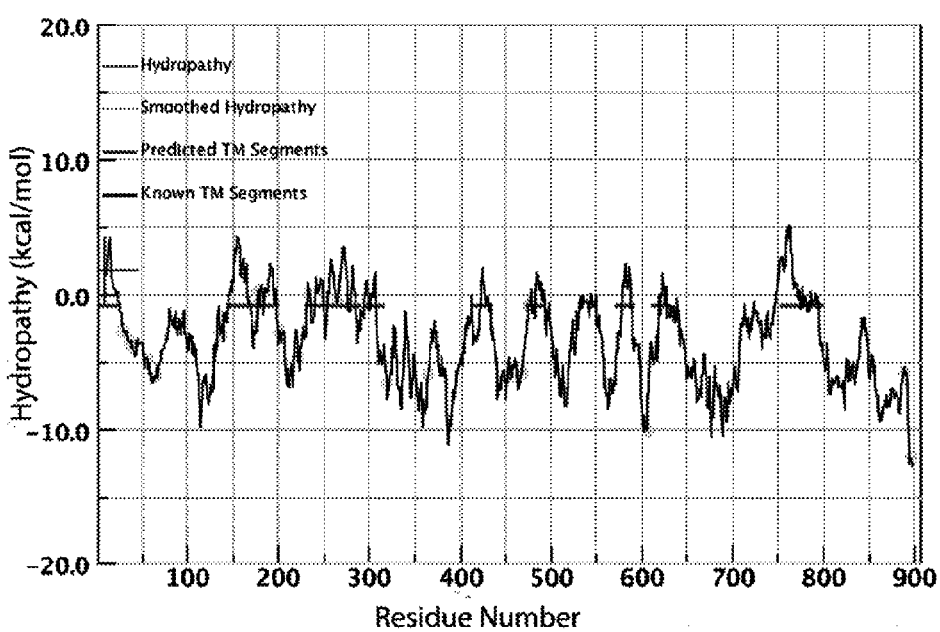

FIG. 1

```
1    MHQGAPSWGR RWFVVWALLG LTLGVLVASA APTSPGTPGV AAATQAANGG PATPAPPPLG
61   AAPTGDPKPK KNKKPKNPTP PRPAGDNATV AAGHATLREH LRDIKAENTD ANFYVCPPPT
121  GATVVQFEQP RRCPTRPEGQ NYTEGIAVVF KENIAPYKFK ATMYYKDVTV SQVWFGHRYS
181  QFMGIFEDRA PVPFEEVIDK INAKGVCRST AKYVRNNLET TAFHRDDHET DMELKPANAA
241  TRTSRGWHTT DLKYNPSRVE AFHRYGTTVN CIVEEVDARS VYPYDEFVLA TGDFVYMSPF
301  YGYREGSHTE HTTYAADRFK QVDGFYARDL TTKARATAPT TRNLLTTPKF TVAWDWVPKR
361  PSVCTMTKWQ EVDEMLRSEY GGSFRFSSDA ISTTFTTNLT EYPLSRVDLG DCIGKDARDA
421  MDRIFARRYN ATHIKVGQPQ YYQANGGFLI AYQPLLSNTL AELYVREHLR EQSRKPPNPT
481  PPPPGASANA SVERIKTTSS IEFARLQFTY NHIQRHVNDM LGRVAIAWCE LQNHELTLWN
541  EARKLNPNAI ASVTVGRRVS ARMLGDVMAV STCVPVAADN VIVQNSMRIS SRPGACYSRP
601  LVSFRYEDQG PLVEGQLGEN NELRLTRDAI EPCTVGHRRY FTFGGGYVYF EEYAYSHQLS
661  RADITTVSTF IDLNITMLED HEFVPLEVYT RHEIKDSGLL DYTEVQRRNQ LHDLRFADID
721  TVIHADANAA MFAGLGAFFE GMGDLGRAVG KVVMGIVGGV VSAVSGVSSF MSNPFGALAV
781  GLLVLAGLAA AFFAFRYVMR LQSNPMKALY PLTTKELKNP TNPDASGEGE EGGDFDEAKL
841  AEAREMIRYM ALVSAMERTE HKAKKKGTSA LLSAKVTDMV MRKRRNTNYT QVPNKDGDAD
901  EDDL
```

(SEQ ID NO: 8)

FIG. 7

| SEQ ID NO: | SEQUENCE |
|---|---|
| 2 | VLTFRRSYAYIYTTYLLGSNTEYVAPPM |
| 142 | WEIHHINKFAQCYSSYSRVIGGTVFVA |
| 12 | WEIHHINKFAQCYSSYSRVIGGTV |
| 13 | WEIHHINKFAQCYSSYSRVIG |
| 14 | WEIHHINKFAQCYSSYSR |
| 15 | WEIHHINKFAQCYSS |
| 16 | HHINKFAQCYSSYSRVIGGTV |
| 17 | NKFAQCYSSYSRVIG |
| 18 | QCYSSYSR |
| 19 | YLLGSNTEYVAPPMWEIHHINKFAQCYSSYSRVIGGTVFVAYHRDSYENKTMQLI |
| 20 | YLLGSNTEYVAPPMWEIHHINKFAQCYSSYSRVIGGTVFVAYHRDSYENKTM |
| 21 | YLLGSNTEYVAPPMWEIHHINKFAQCYSSYSRVIGGTVFVAYHRDSYEN |
| 22 | YLLGSNTEYVAPPMWEIHHINKFAQCYSSYSRVIGGTVFVAYHRDS |
| 23 | YLLGSNTEYVAPPMWEIHHINKFAQCYSSYSRVIGGTVFVAYH |
| 24 | YLLGSNTEYVAPPMWEIHHINKFAQCYSSYSRVIGGTVFV |
| 25 | YLLGSNTEYVAPPMWEIHHINKFAQCYSSYSRVIGGT |
| 26 | YLLGSNTEYVAPPMWEIHHINKFAQCYSSYSRVI |
| 27 | GSNTEYVAPPMWEIHHINKFAQCYSSYSRVIGGTVFVAYHRDSYENKTMQLI |
| 28 | TEYVAPPMWEIHHINKFAQCYSSYSRVIGGTVFVAYHRDSYENKTMQLI |
| 29 | HINKFAQCYSSYSRVIGGTVFVAYHRDSYENKTMQLI |
| 30 | KFAQCYSSYSRVIGGTVFVAYHRDSYENKTMQLI |
| 31 | QCYSSYSRVIGGTVFVAYHRDSYENKTMQLI |
| 32 | VAPPMWEIHHINKFAQCYSSYSRVIGGTVFVAYHRDSYENKTMQLI |
| 33 | PMWEIHHINKFAQCYSSYSRVIGGTVFVAYHRDSYENKTMQLI |
| 34 | EIHHINKFAQCYSSYSRVIGGTVFVAYHRDSYENKTMQLI |
| 35 | WEIHHINKFAQCYSSYSRVIGGTVFVA-human serum albumin |

FIG. 8

| SEQ ID NO: | SEQUENCE |
|---|---|
| 36 | WEIHHINKFAQCYSSYSRVIGGTVFVAGRKKRRQRRRP |
| 37 | WEIHHINKFAQCYSSYSRVIGGTVFVARRRRRRRRR |
| 38 | WEIHHINKFAQCYSSYSRVIGGTVFVAASKSKSKSK |
| 39 | WEIHHINKFAQCYSSYSRVIGGTVFVAP* |
| 40 | N-myristoyl-WEIHHINKFAQCYSSYSRVIGGTVFVA |
| 41 | WEIHHINKFAQCYSSYSRVIGGTVFVA-Cholesterol ester |
| 42 | WEIHHINKFAQCYSSYSRVIGGTVFVA-PEG |
| 43 | cyclo-(CWEIHHINKFAQAYSSYSRVIGGTVFVAC)** |
| 44 | WRIHHINKFAQAYSSYSRVIGGTVFVA |
| 45 | WEIDHINKFAQAYSSYSRVIGGTVFVA |
| 46 | WEIHEINKFAQAYSSYSRVIGGTVFVA |
| 47 | WEIHHINEFAQAYSSYSRVIGGTVFVA |
| 48 | WEIHHINKFAQAYSSYSDVIGGTVFVA |
| 49 | WHSRGSTWLYRETCNLNCMLTITTARSKYPY |
| 50 | SNTHSTRYVTVKDQWHSRGSTWLYRETCNLNCMLTITTARSKYPYHFFATSTGDVVYIS |
| 51 | SNTHSTRYVTVKDQWHSRGSTWLYRETCNLNCMLTITTARSKYPYHFFATSTGDVV |
| 52 | SNTHSTRYVTVKDQWHSRGSTWLYRETCNLNCMLTITTARSKYPYHFFATSTG |
| 53 | SNTHSTRYVTVKDQWHSRGSTWLYRETCNLNCMLTITTARSKYPYHFFAT |
| 54 | SNTHSTRYVTVKDQWHSRGSTWLYRETCNLNCMLTITTARSKYPYHF |
| 55 | SNTHSTRYVTVKDQWHSRGSTWLYRETCNLNCMLTITTARSKYP |
| 56 | SNTHSTRYVTVKDQWHSRGSTWLYRETCNLNCMLTITTARS |
| 57 | SNTHSTRYVTVKDQWHSRGSTWLYRETCNLNCMLTITT |
| 58 | HSTRYVTVKDQWHSRGSTWLYRETCNLNCMLTITTARSKYPYHFFATSTGDVVYIS |
| 59 | RYVTVKDQWHSRGSTWLYRETCNLNCMLTITTARSKYPYHFFATSTGDVVYIS |
| 60 | TVKDQWHSRGSTWLYRETCNLNCMLTITTARSKYPYHFFATSTGDVVYIS |
| 61 | DQWHSRGSTWLYRETCNLNCMLTITTARSKYPYHFFATSTGDVVYIS |
| 62 | HSRGSTWLYRETCNLNCMLTITTARSKYPYHFFATSTGDVVYIS |

FIG. 9

| SEQ ID NO: | SEQUENCE |
|---|---|
| 63 | GSTWLYRETCNLNCMLTITTARSKYPYHFFATSTGDVVYIS |
| 64 | WLYRETCNLNCMLTITTARSKYPYHFFATSTGDVVYIS |
| 65 | WLYRETCNLNCMLTITTARSKYPYHFFATSTGDVVYIS |
| 66 | WHSRGSTWLYRETANLNAMLTITTARSKYPY-human serum albumin |
| 67 | WHSRGSTWLYRETANLNAMLTITTARSKYPYGRKKRRQRRRP |
| 68 | WHSRGSTWLYRETANLNAMLTITTARSKYPYRRRRRRRRR |
| 69 | WHSRGSTWLYRETANLNAMLTITTARSKYPYASKSKSKSK |
| 70 | WHSRGSTWLYRETANLNAMLTITTARSKYPYP* |
| 71 | N-myristoyl-WHSRGSTWLYRETANLNAMLTITTARSKYPY |
| 72 | WHSRGSTWLYRETANLNAMLTITTARSKYPY-Cholesterol ester |
| 73 | WHSRGSTWLYRETANLNAMLTITTARSKYPY-PEG |
| 74 | cyclo-(CWHSRGSTWLYRETANLNAMLTITTARSKYPYC)** |
| 75 | WDSRGSTWLYRETANLNAMLTITTARSKYPY |
| 76 | WHSEGSTWLYRETANLNAMLTITTARSKYPY |
| 77 | WHSRGSTWLYEETANLNAMLTITTARSKYPY |
| 78 | WHSRGSTWLYRRTANLNAMLTITTARSKYPY |
| 79 | WHSRGSTWLYRETANLNAMLTITTADSKYPY |
| 80 | WHSRGSTWLYRETANLNAMLTITTARSEYPY |
| 5 | HFFATSTGDVVYISPFYNGTNRNASYFG |
| 81 | CMLTITTARSKYPYHFFATSTGDVVYISPFYNGTNRNASYFGENADKFFIFPNYTI |
| 82 | CMLTITTARSKYPYHFFATSTGDVVYISPFYNGTNRNASYFGENADKFFIFPN |
| 83 | CMLTITTARSKYPYHFFATSTGDVVYISPFYNGTNRNASYFGENADKFFI |
| 84 | CMLTITTARSKYPYHFFATSTGDVVYISPFYNGTNRNASYFGENADK |
| 85 | CMLTITTARSKYPYHFFATSTGDVVYISPFYNGTNRNASYFGEN |
| 86 | CMLTITTARSKYPYHFFATSTGDVVYISPFYNGTNRNASYF |
| 87 | CMLTITTARSKYPYHFFATSTGDVVYISPFYNGTNRNA |
| 88 | CMLTITTARSKYPYHFFATSTGDVVYISPFYNGTN |

FIG. 10

| SEQ ID NO: | SEQUENCE |
|---|---|
| 89 | TITTARSKYPYHFFATSTGDVVYISPFYNGTNRNASYFGENADKFFIFPNYTI |
| 90 | TARSKYPYHFFATSTGDVVYISPFYNGTNRNASYFGENADKFFIFPNYTI |
| 91 | SKYPYHFFATSTGDVVYISPFYNGTNRNASYFGENADKFFIFPNYTI |
| 92 | PYHFFATSTGDVVYISPFYNGTNRNASYFGENADKFFIFPNYTI |
| 93 | FFATSTGDVVYISPFYNGTNRNASYFGENADKFFIFPNYTI |
| 94 | TSTGDVVYISPFYNGTNRNASYFGENADKFFIFPNYTI |
| 95 | GDVVYISPFYNGTNRNASYFGENADKFFIFPNYTI |
| 96 | VYISPFYNGTNRNASYFGENADKFFIFPNYTI |
| 97 | HFFATSTGDVVYISPFYNGTNRNASYFG-human serum albumin |
| 98 | HFFATSTGDVVYISPFYNGTNRNASYFGGRKKRRQRRRP |
| 99 | HFFATSTGDVVYISPFYNGTNRNASYFGRRRRRRRRR |
| 100 | HFFATSTGDVVYISPFYNGTNRNASYFGASKSKSKSK |
| 101 | HFFATSTGDVVYISPFYNGTNRNASYFGP\* |
| 102 | N-myristoyl-HFFATSTGDVVYISPFYNGTNRNASYFG |
| 103 | HFFATSTGDVVYISPFYNGTNRNASYFG-Cholesterol ester |
| 104 | HFFATSTGDVVYISPFYNGTNRNASYFG-PEG |
| 105 | cyclo-(CHFFATSTGDVVYISPFYNGTNRNASYFGC)**\*\*** |
| 106 | DFFATSTGDVVYISPFYNGTNRNASYFG |
| 107 | HFFATSTGKVVYISPFYNGTNRNASYFG |
| 108 | HFFATSTGDVVYISPFYNGTNENASYFG |
| 6 | FFIFPNYTIVSDFGRPNAA |
| 109 | TNRNASYFGENADKFFIFPNYTIVSDFGRPNAAPETHRLVAFLERAD |
| 110 | TNRNASYFGENADKFFIFPNYTIVSDFGRPNAAPETHRLVAFLE |
| 111 | TNRNASYFGENADKFFIFPNYTIVSDFGRPNAAPETHRLVA |
| 112 | TNRNASYFGENADKFFIFPNYTIVSDFGRPNAAPETHR |
| 113 | TNRNASYFGENADKFFIFPNYTIVSDFGRPNAAPE |
| 114 | TNENASYFGENADKFFIFPNYTIVSDFGRPNAAPE |

FIG. 11

| SEQ ID NO: | SEQUENCE |
|---|---|
| 115 | TNRNASYFGENADKFFIFPNYTIVSDFGRPNA |
| 116 | TNENASYFGENADKFFIFPNYTIVSDFGRPNA |
| 117 | NASYFGENADKFFIFPNYTIVSDFGRPNAAPETHRLVAFLERAD |
| 118 | YFGENADKFFIFPNYTIVSDFGRPNAAPETHRLVAFLERAD |
| 119 | ENADKFFIFPNYTIVSDFGRPNAAPETHRLVAFLERAD |
| 120 | N-myristoyl-FFIFPNYTIVSDFGRPNAA |
| 121 | FFIFPNYTIVSDFGRPNAA-Cholesterol ester |
| 122 | FFIFPNYTIVSDFGRPNAA-PEG |
| 123 | cyclo-(C FFIFPNYTIVSDFGRPNAA C)** |
| 124 | FFIFPNYTIVSRFGRPNAA |
| 125 | FFIFPNYTIVSDFGEPNAA |
| 126 | FFIFPQYTIVSRFGRPNAA |
| 127 | FFIFPQYTIVSDFGEPNAA |
| 128 | FFIFPNWTIVSRFGRPNAA |
| 129 | FFIFPNYTIVSR |
| 130 | FFIFPNYTIV |
| 131 | FFIFPNYTI |
| 132 | DKFFIFPNYTIVSDFGRPNAAPETHRLVAFLERAD |
| 133 | FIFPNYTIVSDFGRPNAAPETHRLVAFLERAD |
| 134 | PNYTIVSDFGRPNAAPETHRLVAFLERAD |
| 135 | TIVSDFGRPNAAPETHRLVAFLERAD |
| 136 | SDFGRPNAAPETHRLVAFLERAD |
| 137 | FFIFPNYTIVSDFGRPNAA-human serum albumin |
| 138 | FFIFPNYTIVSDFGRPNAAGRKKRRQRRRP |
| 139 | FFIFPNYTIVSDFGRPNAARRRRRRRRR |
| 140 | FFIFPNYTIVSDFGRPNAAASKSKSKSK |
| 141 | FFIFPNYTIVSDFGRPNAAP* |

FIG. 12

SEQUENCE LISTING

```
<160> NUMBER OF SEQ ID NOS: 149

<210> SEQ ID NO 1
<211> LENGTH: 900
<212> TYPE: PRT
<213> ORGANISM: Artificial Sequence
<220> FEATURE:
<223> OTHER INFORMATION: human cytomegalovirus glycoprotein B

<400> SEQUENCE: 1

Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190
```

```
Ile Gly Gly Thr Val Phe Val Ala Tyr His Arg Asp Ser Tyr Glu Asn
            195                 200                 205
Lys Thr Met Gln Leu Ile Pro Asp Asp Tyr Ser Asn Thr His Ser Thr
210                 215                 220
Arg Tyr Val Thr Val Lys Asp Gln Trp His Ser Arg Gly Ser Thr Trp
225                 230                 235                 240
Leu Tyr Arg Glu Thr Cys Asn Leu Asn Cys Met Leu Thr Ile Thr Thr
                245                 250                 255
Ala Arg Ser Lys Tyr Pro Tyr His Phe Ala Thr Ser Thr Gly Asp
                260                 265                 270
Val Val Tyr Ile Ser Pro Phe Tyr Asn Gly Thr Asn Arg Asn Ala Ser
                275                 280                 285
Tyr Phe Gly Glu Asn Ala Asp Lys Phe Phe Ile Phe Pro Asn Tyr Thr
        290                 295                 300
Ile Val Ser Asp Phe Gly Arg Pro Asn Ala Ala Pro Glu Thr His Arg
305                 310                 315                 320
Leu Val Ala Phe Leu Glu Arg Ala Asp Ser Val Ile Ser Trp Asp Ile
                325                 330                 335
Gln Asp Glu Lys Asn Val Thr Cys Gln Leu Thr Phe Trp Glu Ala Ser
                340                 345                 350
Glu Arg Thr Ile Arg Ser Glu Ala Glu Asp Ser Tyr His Phe Ser Ser
        355                 360                 365
Ala Lys Met Thr Ala Thr Phe Leu Ser Lys Lys Gln Glu Val Asn Met
        370                 375                 380
Ser Asp Ser Ala Leu Asp Cys Val Arg Asp Glu Ala Ile Asn Lys Leu
385                 390                 395                 400
Gln Gln Ile Phe Asn Thr Ser Tyr Asn Gln Thr Tyr Glu Lys Tyr Gly
                405                 410                 415
Asn Val Ser Val Phe Glu Thr Ser Gly Gly Leu Val Val Phe Trp Gln
                420                 425                 430
Gly Ile Lys Gln Lys Ser Leu Val Glu Leu Glu Arg Leu Ala Asn Arg
        435                 440                 445
Ser Ser Leu Asn Ile Thr His Arg Thr Arg Arg Ser Thr Ser Asp Asn
450                 455                 460
Asn Thr Thr His Leu Ser Ser Met Glu Ser Val His Asn Leu Val Tyr
465                 470                 475                 480
Ala Gln Leu Gln Phe Thr Tyr Asp Thr Leu Arg Gly Tyr Ile Asn Arg
                485                 490                 495
Ala Leu Ala Gln Ile Ala Glu Ala Trp Cys Val Asp Gln Arg Arg Thr
                500                 505                 510
Leu Glu Val Phe Lys Glu Leu Ser Lys Ile Asn Pro Ser Ala Ile Leu
                515                 520                 525
Ser Ala Ile Tyr Asn Lys Pro Ile Ala Ala Arg Phe Met Gly Asp Val
530                 535                 540
Leu Gly Leu Ala Ser Cys Val Thr Ile Asn Gln Thr Ser Val Lys Val
545                 550                 555                 560
Leu Arg Asp Met Asn Val Lys Glu Ser Pro Gly Arg Cys Tyr Ser Arg
                565                 570                 575
Pro Val Val Ile Phe Asn Phe Ala Asn Ser Ser Tyr Val Gln Tyr Gly
                580                 585                 590
Gln Leu Gly Glu Asp Asn Glu Ile Leu Leu Gly Asn His Arg Thr Glu
                595                 600                 605
Glu Cys Gln Leu Pro Ser Leu Lys Ile Phe Ile Ala Gly Asn Ser Ala
```

```
            610                 615                 620
Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                    645                 650                 655

Asn Thr Asp Phe Arg Val Leu Glu Leu Tyr Ser Gln Lys Glu Leu Arg
                660                 665                 670

Ser Ser Asn Val Phe Asp Leu Glu Glu Ile Met Arg Glu Phe Asn Ser
            675                 680                 685

Tyr Lys Gln Arg Val Lys Tyr Val Glu Asp Lys Val Asp Pro Leu
        690                 695                 700

Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
                    725                 730                 735

Ala Ser Val Val Glu Gly Val Ala Thr Phe Leu Lys Asn Pro Phe Gly
                740                 745                 750

Ala Phe Thr Ile Ile Leu Val Ala Ile Ala Val Val Ile Ile Thr Tyr
            755                 760                 765

Leu Ile Tyr Thr Arg Gln Arg Arg Leu Cys Thr Gln Pro Leu Gln Asn
770                 775                 780

Leu Phe Pro Tyr Leu Val Ser Ala Asp Gly Thr Thr Val Thr Ser Gly
785                 790                 795                 800

Ser Thr Lys Asp Thr Ser Leu Gln Ala Pro Pro Ser Tyr Glu Glu Ser
                    805                 810                 815

Val Tyr Asn Ser Gly Arg Lys Gly Pro Gly Pro Pro Ser Ser Asp Ala
                820                 825                 830

Ser Thr Ala Ala Pro Pro Tyr Thr Asn Glu Gln Ala Tyr Gln Met Leu
            835                 840                 845

Leu Ala Leu Ala Arg Leu Asp Ala Glu Gln Arg Ala Gln Gln Asn Gly
850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                    885                 890                 895

Leu Lys Asp Ser
            900

<210> SEQ ID NO 2
<211> LENGTH: 28
<212> TYPE: PRT
<213> ORGANISM: Artificial Sequence
<220> FEATURE:
<223> OTHER INFORMATION: human cytomegalovirus glycoprotein B peptide

<400> SEQ

```
<400> SEQUENCE: 3

Trp Glu Ile His His Ile Asn Lys Phe Ala Gln Cys Tyr Ser Ser Tyr
 1               5                  10                  15

Ser Arg Val Ile Gly Gly Thr Val Phe Val Ala
            20                  25

<210> SEQ ID NO 4
<211> LENGTH: 31
<212> TYPE: PRT
<213> ORGANISM: Artificial Sequence
<220> FEATURE:
<223> OTHER INFORMATION: human cytomegalovirus glycoprotein B peptide

<400> SEQUENCE: 4

Trp His Ser Arg Gly Ser Thr Trp Leu Tyr Arg Glu Thr Cys Asn Leu
 1               5                  10                  15

Asn Cys Met Leu Thr Ile Thr Thr Ala Arg Ser Lys Tyr Pro Tyr
            20                  25                  30

<210> SEQ ID NO 5
<211> LENGTH: 28
<212> TYPE: PRT
<213> ORGANISM: Artificial Sequence
<220> FEATURE:
<223> OTHER INFORMATION: human cytomegalovirus glycoprotein B peptide

<400> SEQUENCE: 5

His Phe Phe Ala Thr Ser Thr Gly Asp Val Val Tyr Ile Ser Pro Phe
 1               5                  10                  15

Tyr Asn Gly Thr Asn Arg Asn Ala Ser Tyr Phe Gly
            20                  25

<210> SEQ ID NO 6
<211> LENGTH: 19
<212> TYPE: PRT
<213> ORGANISM: Artificial Sequence
<220> FEATURE:
<223> OTHER INFORMATION: human cytomegalovirus glycoprotein B peptide

<400> SEQUENCE: 6

Phe Phe Ile Phe Pro Asn Tyr Thr Ile Val Ser Asp Phe Gly Arg Pro
 1               5                  10                  15

Asn Ala Ala

<210> SEQ ID NO 7
<211> LENGTH: 19
<212> TYPE: PRT
<213> ORGANISM: Artificial Sequence
<220> FEATURE:
<223> OTHER INFORMATION: human cytomegalovirus glycoprotein B peptide

<400> SEQUENCE: 7

His Asn Leu Val Tyr Ala Gln Leu Gln Phe Thr Tyr Asp Thr Leu Arg
 1               5                  10                  15

Gly Tyr Ile

<210> SEQ ID NO 8
<211> LENGTH: 904
<212> TYPE: PRT
<213> ORGANISM: Artificial Sequence
<220> FEATURE:
<223> OTHER INFORMATION: HSV-1 glycoprotein B
```

```
<400> SEQUENCE: 8

Met His Gln Gly Ala Pro Ser Trp Gly Arg Arg Trp Phe Val Val Trp
 1               5                  10                  15

Ala Leu Leu Gly Leu Thr Leu Gly Val Leu Ala Ser Ala Ala Pro
             20                  25                  30

Thr Ser Pro Gly Thr Pro Gly Val Ala Ala Thr Gln Ala Ala Asn
         35                  40                  45

Gly Gly Pro Ala Thr Pro Ala Pro Pro Leu Gly Ala Ala Pro Thr
     50                  55                  60

Gly Asp Pro Lys Pro Lys Asn Lys Lys Pro Lys Asn Pro Thr Pro
 65                  70                  75                  80

Pro Arg Pro Ala Gly Asp Asn Ala Thr Val Ala Ala Gly His Ala Thr
                 85                  90                  95

Leu Arg Glu His Leu Arg Asp Ile Lys Ala Glu Asn Thr Asp Ala Asn
                100                 105                 110

Phe Tyr Val Cys Pro Pro Thr Gly Ala Thr Val Val Gln Phe Glu
            115                 120                 125

Gln Pro Arg Arg Cys Pro Thr Arg Pro Glu Gly Gln Asn Tyr Thr Glu
        130                 135                 140

Gly Ile Ala Val Val Phe Lys Glu Asn Ile Ala Pro Tyr Lys Phe Lys
145                 150                 155                 160

Ala Thr Met Tyr Tyr Lys Asp Val Thr Val Ser Gln Val Trp Phe Gly
                165                 170                 175

His Arg Tyr Ser Gln Phe Met Gly Ile Phe Glu Asp Arg Ala Pro Val
            180                 185                 190

Pro Phe Glu Glu Val Ile Asp Lys Ile Asn Ala Lys Gly Val Cys Arg
        195                 200                 205

Ser Thr Ala Lys Tyr Val Arg Asn Asn Leu Glu Thr Thr Ala Phe His
    210                 215                 220

Arg Asp Asp His Glu Thr Asp Met Glu Leu Lys Pro Ala Asn Ala Ala
225                 230                 235                 240

Thr Arg Thr Ser Arg Gly Trp His Thr Thr Asp Leu Lys Tyr Asn Pro
                245                 250                 255

Ser Arg Val Glu Ala Phe His Arg Tyr Gly Thr Thr Val Asn Cys Ile
            260                 265                 270

Val Glu Glu Val Asp Ala Arg Ser Val Tyr Pro Tyr Asp Glu Phe Val
        275                 280                 285

Leu Ala Thr Gly Asp Phe Val Tyr Met Ser Pro Phe Tyr Gly Tyr Arg
290                 295                 300

Glu Gly Ser His Thr Glu His Thr Thr Tyr Ala Ala Asp Arg Phe Lys
305                 310                 315                 320

Gln Val Asp Gly Phe Tyr Ala Arg Asp Leu Thr Lys Ala Arg Ala
            325                 330                 335

Thr Ala Pro Thr Thr Arg Asn Leu Leu Thr Thr Pro Lys Phe Thr Val
                340                 345                 350

Ala Trp Asp Trp Val Pro Lys Arg Pro Ser Val Cys Thr Met Thr Lys
            355                 360                 365

Trp Gln Glu Val Asp Glu Met Leu Arg Ser Glu Tyr Gly Gly Ser Phe
    370                 375                 380

Arg Phe Ser Ser Asp Ala Ile Ser Thr Thr Phe Thr Thr Asn Leu Thr
385                 390                 395                 400

Glu Tyr Pro Leu Ser Arg Val Asp Leu Gly Asp Cys Ile Gly Lys Asp
                405                 410                 415
```

```
Ala Arg Asp Ala Met Asp Arg Ile Phe Ala Arg Arg Tyr Asn Ala Thr
            420                 425                 430

His Ile Lys Val Gly Gln Pro Gln Tyr Tyr Gln Ala Asn Gly Gly Phe
            435                 440                 445

Leu Ile Ala Tyr Gln Pro Leu Leu Ser Asn Thr Leu Ala Glu Leu Tyr
            450                 455                 460

Val Arg Glu His Leu Arg Glu Gln Ser Arg Lys Pro Pro Asn Pro Thr
465                 470                 475                 480

Pro Pro Pro Gly Ala Ser Ala Asn Ala Ser Val Glu Arg Ile Lys
                485                 490                 495

Thr Thr Ser Ser Ile Glu Phe Ala Arg Leu Gln Phe Thr Tyr Asn His
            500                 505                 510

Ile Gln Arg His Val Asn Asp Met Leu Gly Arg Val Ala Ile Ala Trp
            515                 520                 525

Cys Glu Leu Gln Asn His Glu Leu Thr Leu Trp Asn Glu Ala Arg Lys
530                 535                 540

Leu Asn Pro Asn Ala Ile Ala Ser Val Thr Val Gly Arg Arg Val Ser
545                 550                 555                 560

Ala Arg Met Leu Gly Asp Val Met Ala Val Ser Thr Cys Val Pro Val
                565                 570                 575

Ala Ala Asp Asn Val Ile Val Gln Asn Ser Met Arg Ile Ser Ser Arg
                580                 585                 590

Pro Gly Ala Cys Tyr Ser Arg Pro Leu Val Ser Phe Arg Tyr Glu Asp
                595                 600                 605

Gln Gly Pro Leu Val Glu Gly Gln Leu Gly Glu Asn Asn Glu Leu Arg
                610                 615                 620

Leu Thr Arg Asp Ala Ile Glu Pro Cys Thr Val Gly His Arg Arg Tyr
625                 630                 635                 640

Phe Thr Phe Gly Gly Gly Tyr Val Tyr Phe Glu Glu Tyr Ala Tyr Ser
                645                 650                 655

His Gln Leu Ser Arg Ala Asp Ile Thr Thr Val Ser Thr Phe Ile Asp
                660                 665                 670

Leu Asn Ile Thr Met Leu Glu Asp His Glu Phe Val Pro Leu Glu Val
                675                 680                 685

Tyr Thr Arg His Glu Ile Lys Asp Ser Gly Leu Leu Asp Tyr Thr Glu
                690                 695                 700

Val Gln Arg Arg Asn Gln Leu His Asp Leu Arg Phe Ala Asp Ile Asp
705                 710                 715                 720

Thr Val Ile His Ala Asp Ala Asn Ala Ala Met Phe Ala Gly Leu Gly
                725                 730                 735

Ala Phe Phe Glu Gly Met Gly Asp Leu Gly Arg Ala Val Gly Lys Val
                740                 745                 750

Val Met Gly Ile Val Gly Gly Val Ser Ala Val Ser Gly Val Ser
                755                 760                 765

Ser Phe Met Ser Asn Pro Phe Gly Ala Leu Ala Val Gly Leu Leu Val
                770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
                805                 810                 815

Leu Lys Asn Pro Thr Asn Pro Asp Ala Ser Gly Glu Gly Glu Glu Gly
                820                 825                 830
```

```
Gly Asp Phe Asp Glu Ala Lys Leu Ala Glu Ala Arg Glu Met Ile Arg
            835                 840                 845

Tyr Met Ala Leu Val Ser Ala Met Glu Arg Thr Glu His Lys Ala Lys
    850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                885                 890                 895

Gly Asp Ala Asp Glu Asp Leu
            900

<210> SEQ ID NO 9
<211> LENGTH: 9
<212> TYPE: PRT
<213> ORGANISM: Artificial Sequence
<220> FEATURE:
<223> OTHER INFORMATION: cell penetration enhancing peptide

<400> SEQUENCE: 9

Arg Arg Arg Arg Arg Arg Arg Arg Arg
1               5

<210> SEQ ID NO 10
<211> LENGTH: 11
<212> TYPE: PRT
<213> ORGANISM: Artificial Sequence
<220> FEATURE:
<223> OTHER INFORMATION: cell penetration enhancing peptide

<400> SEQUENCE: 10

Gly Arg Lys Lys Arg Arg Gln Arg Arg Arg Pro
1               5                   10

<210> SEQ ID NO 11
<211> LENGTH: 9
<212> TYPE: PRT
<213> ORGANISM: Artificial Sequence
<220> FEATURE:
<223> OTHER INFORMATION: solubility enhancing peptide

<400> SEQUENCE: 11

Ala Ser Lys Ser Lys Ser Lys Ser Lys
1               5

<210> SEQ ID NO 12
<211> LENGTH: 24
<212> TYPE: PRT
<213> ORGANISM: Artificial Sequence
<220> FEATURE:
<223> OTHER INFORMATION: human cytomegalovirus glycoprotein B peptide

<400> SEQUENCE: 12

Trp Glu Ile His His Ile Asn Lys Phe Ala Gln Cys Tyr Ser Ser Tyr
1               5                   10                  15

Ser Arg Val Ile Gly Gly Thr Val
            20

<210> SEQ ID NO 13
<211> LENGTH: 21
<212> TYPE: PRT
<213> ORGANISM: Artificial Sequence
<220> FEATURE:
<223> OTHER INFORMATION: human cytomegalovirus glycoprotein B peptide

<400> SEQUENCE: 13
```

```
Trp Glu Ile His His Ile Asn Lys Phe Ala Gln Cys Tyr Ser Ser Tyr
1               5                   10                  15

Ser Arg Val Ile Gly
            20

<210> SEQ ID NO 14
<211> LENGTH: 18
<212> TYPE: PRT
<213> ORGANISM: Artificial Sequence
<220> FEATURE:
<223> OTHER INFORMATION: human cytomegalovirus glycoprotein B peptide

<400> SEQUENCE: 14

Trp Glu Ile His His Ile Asn Lys Phe Ala Gln Cys Tyr Ser Ser Tyr
1               5                   10                  15

Ser Arg

<210> SEQ ID NO 15
<211> LENGTH: 15
<212> TYPE: PRT
<213> ORGANISM: Artificial Sequence
<220> FEATURE:
<223> OTHER INFORMATION: human cytomegalovirus glycoprotein B peptide

<400> SEQUENCE: 15

Trp Glu Ile His His Ile Asn Lys Phe Ala Gln Cys Tyr Ser Ser
1               5                   10                  15

<210> SEQ ID NO 16
<211> LENGTH: 21
<212> TYPE: PRT
<213> ORGANISM: Artificial Sequence
<220> FEATURE:
<223> OTHER INFORMATION: human cytomegalovirus glycoprotein B peptide

<400> SEQUENCE: 16

His His Ile Asn Lys Phe Ala Gln Cys Tyr Ser Ser Tyr Ser Arg Val
1               5                   10                  15

Ile Gly Gly Thr Val
            20

<210> SEQ ID NO 17
<211> LENGTH: 15
<212> TYPE: PRT
<213> ORGANISM: Artificial Sequence
<220> FEATURE:
<223> OTHER INFORMATION: human cytomegalovirus glycoprotein B peptide

<400> SEQUENCE: 17

Asn Lys Phe Ala Gln Cys Tyr Ser Ser Tyr Ser Arg Val Ile Gly
1               5                   10                  15

<210> SEQ ID NO 18
<211> LENGTH: 8
<212> TYPE: PRT
<213> ORGANISM: Artificial Sequence
<220> FEATURE:
<223> OTHER INFORMATION: human cytomegalovirus glycoprotein B peptide

<400> SEQUENCE: 18

Gln Cys Tyr Ser Ser Tyr Ser Arg
1               5

<210> SEQ ID NO 19
```

<211> LENGTH: 55
<212> TYPE: PRT
<213> ORGANISM: Artificial Sequence
<220> FEATURE:
<223> OTHER INFORMATION: human cytomegalovirus glycoprotein B peptide

<400> SEQUENCE: 19

Tyr Leu Leu Gly Ser Asn Thr Glu Tyr Val Ala Pro Pro Met Trp Glu
1               5                   10                  15

Ile His His Ile Asn Lys Phe Ala Gln Cys Tyr Ser Ser Tyr Ser Arg
            20                  25                  30

Val Ile Gly Gly Thr Val Phe Val Ala Tyr His Arg Asp Ser Tyr Glu
        35                  40                  45

Asn Lys Thr Met Gln Leu Ile
    50                  55

<210> SEQ ID NO 20
<211> LENGTH: 52
<212> TYPE: PRT
<213> ORGANISM: Artificial Sequence
<220> FEATURE:
<223> OTHER INFORMATION: human cytomegalovirus glycoprotein B peptide

<400> SEQUENCE: 20

Tyr Leu Leu Gly Ser Asn Thr Glu Tyr Val Ala Pro Pro Met Trp Glu
1               5                   10                  15

Ile His His Ile Asn Lys Phe Ala Gln Cys Tyr Ser Ser Tyr Ser Arg
            20                  25                  30

Val Ile Gly Gly Thr Val Phe Val Ala Tyr His Arg Asp Ser Tyr Glu
        35                  40                  45

Asn Lys Thr Met
    50

<210> SEQ ID NO 21
<211> LENGTH: 49
<212> TYPE: PRT
<213> ORGANISM: Artificial Sequence
<220> FEATURE:
<223> OTHER INFORMATION: human cytomegalovirus glycoprotein B peptide

<400> SEQUENCE: 21

Tyr Leu Leu Gly Ser Asn Thr Glu Tyr Val Ala Pro Pro Met Trp Glu
1               5                   10                  15

Ile His His Ile Asn Lys Phe Ala Gln Cys Tyr Ser Ser Tyr Ser Arg
            20                  25                  30

Val Ile Gly Gly Thr Val Phe Val Ala Tyr His Arg Asp Ser Tyr Glu
        35                  40                  45

Asn

<210> SEQ ID NO 22
<211> LENGTH: 46
<212> TYPE: PRT
<213> ORGANISM: Artificial Sequence
<220> FEATURE:
<223> OTHER INFORMATION: human cytomegalovirus glycoprotein B peptide

<400> SEQUENCE: 22

Tyr Leu Leu Gly Ser Asn Thr Glu Tyr Val Ala Pro Pro Met Trp Glu
1               5                   10                  15

Ile His His Ile Asn Lys Phe Ala Gln Cys Tyr Ser Ser Tyr Ser Arg
            20                  25                  30

```
Val Ile Gly Gly Thr Val Phe Val Ala Tyr His Arg Asp Ser
        35                  40                  45

<210> SEQ ID NO 23
<211> LENGTH: 43
<212> TYPE: PRT
<213> ORGANISM: Artificial Sequence
<220> FEATURE:
<223> OTHER INFORMATION: human cytomegalovirus glycoprotein B peptide

<400> SEQUENCE: 23

Tyr Leu Leu Gly Ser Asn Thr Glu Tyr Val Ala Pro Pro Met Trp Glu
1               5                   10                  15

Ile His His Ile Asn Lys Phe Ala Gln Cys Tyr Ser Ser Tyr Ser Arg
            20                  25                  30

Val Ile Gly Gly Thr Val Phe Val Ala Tyr His
        35                  40

<210> SEQ ID NO 24
<211> LENGTH: 40
<212> TYPE: PRT
<213> ORGANISM: Artificial Sequence
<220> FEATURE:
<223> OTHER INFORMATION: human cytomegalovirus glycoprotein B peptide

<400> SEQUENCE: 24

Tyr Leu Leu Gly Ser Asn Thr Glu Tyr Val Ala Pro Pro Met Tr

-continued

<210> SEQ ID NO 27
<211> LENGTH: 52
<212> TYPE: PRT
<213> ORGANISM: Artificial Sequence
<220> FEATURE:
<223> OTHER INFORMATION: human cytomegalovirus glycoprotein B peptide

<400> SEQUENCE: 27

Gly Ser Asn Thr Glu Tyr Val Ala Pro Pro Met Trp Glu Ile His His
1               5                   10                  15

Ile Asn Lys Phe Ala Gln Cys Tyr Ser Ser Tyr Ser Arg Val Ile Gly
            20                  25                  30

Gly Thr Val Phe Val Ala Tyr His Arg Asp Ser Tyr Glu Asn Lys Thr
        35                  40                  45

Met Gln Leu Ile
    50

<210> SEQ ID NO 28
<211> LENGTH: 49
<212> TYPE: PRT
<213> ORGANISM: Artificial Sequence
<220> FEATURE:
<223> OTHER INFORMATION: human cytomegalovirus glycoprotein B peptide

<400> SEQUENCE: 28

Thr Glu Tyr Val Ala Pro Pro Met Trp Glu Ile His His Ile Asn Lys
1               5                   10                  15

Phe Ala Gln Cys Tyr Ser Ser Tyr Ser Arg Val Ile Gly Gly Thr Val
            20                  25                  30

Phe Val Ala Tyr His Arg Asp Ser Tyr Glu Asn Lys Thr Met Gln Leu
        35                  40                  45

Ile

<210> SEQ ID NO 29
<211> LENGTH: 37
<212> TYPE: PRT
<213> ORGANISM: Artificial Sequence
<220> FEATURE:
<223> OTHER INFORMATION: human cytomegalovirus glycoprotein B peptide

<400> SEQUENCE: 29

His Ile Asn Lys Phe Ala Gln Cys Tyr Ser Ser Tyr Ser Arg Val Ile
1               5                   10                  15

Gly Gly Thr Val Phe Val Ala Tyr His Arg Asp Ser Tyr Glu Asn Lys
            20                  25                  30

Thr Met Gln Leu Ile
        35

<210> SEQ ID NO 30
<211> LENGTH: 34
<212> TYPE: PRT
<213> ORGANISM: Artificial Sequence
<220> FEATURE:
<223> OTHER INFORMATION: human cytomegalovirus glycoprotein B peptide

<400> SEQUENCE: 30

Lys Phe Ala Gln Cys Tyr Ser Ser Tyr Ser Arg Val Ile Gly Gly Thr
1               5                   10                  15

Val Phe Val Ala Tyr His Arg Asp Ser Tyr Glu Asn Lys Thr Met Gln
            20                  25                  30

Leu Ile

```
<210> SEQ ID NO 31
<211> LENGTH: 31
<212> TYPE: PRT
<213> ORGANISM: Artificial Sequence
<220> FEATURE:
<223> OTHER INFORMATION: human cytomegalovirus glycoprotein B peptide

<400> SEQUENCE: 31

Gln Cys Tyr Ser Ser Tyr Ser Arg Val Ile Gly Gly Thr Val Phe Val
1               5                   10                  15

Ala Tyr His Arg Asp Ser Tyr Glu Asn Lys Thr Met Gln Leu Ile
            20                  25                  30

<210> SEQ ID NO 32
<211> LENGTH: 46
<212> TYPE: PRT
<213> ORGANISM: Artificial Sequence
<220> FEATURE:
<223> OTHER INFORMATION: human cytomegalovirus glycoprotein B peptide

<400> SEQUENCE: 32

Val Ala Pro Pro Met Trp Glu Ile His His Ile Asn Lys Phe Ala Gln
1               5                   10                  15

Cys Tyr Ser Ser Tyr Ser Arg Val Ile Gly Gly Thr Val Phe Val Ala
            20                  25                  30

Tyr His Arg Asp Ser Tyr Glu Asn Lys Thr Met Gln Leu Ile
        35                  40                  45

<210> SEQ ID NO 33
<211> LENGTH: 43
<212> TYPE: PRT
<213> ORGANISM: Artificial Sequence
<220> FEATURE:
<223> OTHER INFORMATION: human cytomegalovirus glycoprotein B peptide

<400> SEQUENCE: 33

Pro Met Trp Glu Ile His His Ile Asn Lys Phe Ala Gln Cys Tyr Ser
1               5                   10                  15

Ser Tyr Ser Arg Val Ile Gly Gly Thr Val Phe Val Ala Tyr His Arg
            20                  25                  30

Asp Ser Tyr Glu Asn Lys Thr Met Gln Leu Ile
        35                  40

<210> SEQ ID NO 34
<211> LENGTH: 40
<212> TYPE: PRT
<213> ORGANISM: Artificial Sequence
<220> FEATURE:
<223> OTHER INFORMATION: human cytomegalovirus glycoprotein B peptide

<400> SEQUENCE: 34

Glu Ile His His Ile Asn Lys Phe Ala Gln Cys Tyr Ser Ser Tyr Ser
1               5                   10                  15

Arg Val Ile Gly Gly Thr Val Phe Val Ala Tyr His Arg Asp Ser Tyr
            20                  25                  30

Glu Asn Lys Thr Met Gln Leu Ile
        35                  40

<210> SEQ ID NO 35
<211> LENGTH: 27
<212> TYPE: PRT
<213> ORGANISM: Artificial Sequence
<220> FEATURE:
```

<223> OTHER INFORMATION: human cytomegalovirus glycoprotein B peptide
<221> NAME/KEY: MOD_RES
<222> LOCATION: 27
<223> OTHER INFORMATION: Ala 27 fused to human serum albumin

<400> SEQUENCE: 35

Trp Glu Ile His His Ile Asn Lys Phe Ala Gln Cys Tyr Ser Ser Tyr
1               5                   10                  15

Ser Arg Val Ile Gly Gly Thr Val Phe Val Ala
            20                  25

<210> SEQ ID NO 36
<211> LENGTH: 38
<212> TYPE: PRT
<213> ORGANISM: Artificial Sequence
<220> FEATURE:
<223> OTHER INFORMATION: human cytomegalovirus glycoprotein B peptide

<400> SEQUENCE: 36

Trp Glu Ile His His Ile Asn Lys Phe Ala Gln Cys Tyr Ser Ser Tyr
1               5                   10                  15

Ser Arg Val Ile Gly Gly Thr Val Phe Val Ala Gly Arg Lys Lys Arg
            20                  25                  30

Arg Gln Arg Arg Arg Pro
        35

<210> SEQ ID NO 37
<211> LENGTH: 36
<212> TYPE: PRT
<213> ORGANISM: Artificial Sequence
<220> FEATURE:
<223> OTHER INFORMATION: human cytomegalovirus glycoprotein B peptide

<400> SEQUENCE: 37

Trp Glu Ile His His Ile Asn Lys Phe Ala Gln Cys Tyr Ser Ser Tyr
1               5                   10                  15

Ser Arg Val Ile Gly Gly Thr Val Phe Val Ala Arg Arg Arg Arg Arg
            20                  25                  30

Arg Arg Arg Arg
        35

<210> SEQ ID NO 38
<211> LENGTH: 36
<212> TYPE: PRT
<213> ORGANISM: Artificial Sequence
<220> FEATURE:
<223> OTHER INFORMATION: human cytomegalovirus glycoprotein B peptide

<400> SEQUENCE: 38

Trp Glu Ile His His Ile Asn Lys Phe Ala Gln Cys Tyr Ser Ser Tyr
1               5                   10                  15

Ser Arg Val Ile Gly Gly Thr Val Phe Val Ala Ala Ser Lys Ser Lys
            20                  25                  30

Ser Lys Ser Lys
        35

<210> SEQ ID NO 39
<211> LENGTH: 28
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 28

```
<223> OTHER INFORMATION: D-Pro

<400> SEQUENCE: 39

Trp Glu Ile His His Ile Asn Lys Phe Ala Gln Cys Tyr Ser Ser Tyr
 1               5                  10                  15

Ser Arg Val Ile Gly Gly Thr Val Phe Val Ala Pro
            20                  25

<210> SEQ ID NO 40
<211> LENGTH: 27
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 1
<223> OTHER INFORMATION: N-myristoyl

<400> SEQUENCE: 40

Trp Glu Ile His His Ile Asn Lys Phe Ala Gln Cys Tyr Ser Ser Tyr
 1               5                  10                  15

Ser Arg Val Ile Gly Gly Thr Val Phe Val Ala
            20                  25

<210> SEQ ID NO 41
<211> LENGTH: 27
<212> TYPE: PRT
<213> ORGANISM: Artificial Sequence
<220> FEATURE:
<223> OTHER INFORMATION: human cytomegalovirus glycoprotein B peptide
<221> NAME/KEY: LIPID
<222> LOCATION: 27
<223> OTHER INFORMATION: Cholesterol ester

<400> SEQUENCE: 41

Trp Glu Ile His His Ile Asn Lys Phe Ala Gln Cys Tyr Ser Ser Tyr
 1               5                  10                  15

Ser Arg Val Ile Gly Gly Thr Val Phe Val Ala
            20                  25

<210> SEQ ID NO 42
<211> LENGTH: 27
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 27
<223> OTHER INFORMATION: polyethylene glycol derivative

<400> SEQUENCE: 42

Trp Glu Ile His His Ile Asn Lys Phe Ala Gln Cys Tyr Ser Ser Tyr
 1               5                  10                  15

Ser Arg Val Ile Gly Gly Thr Val Phe Val Ala
            20                  25

<210> SEQ ID NO 43
<211> LENGTH: 29
<212> TYPE: PRT
<213> ORGANISM: Artificial Sequence
<220> FEATURE:
<223> OTHER INFORMATION: heterodetic cyclic human cytomegalovirus
      glycoprotein B peptide
<221> NAME/KEY: DISULFID
<222> LOCATION: 1, 29
<223> OTHER INFORMATION: Disulfide bridge between Cys1 and Cys29
```

```
<400> SEQUENCE: 43

Cys Trp Glu Ile His His Ile Asn Lys Phe Ala Gln Ala Tyr Ser Ser
 1               5                  10                  15

Tyr Ser Arg Val Ile Gly Gly Thr Val Phe Val Ala Cys
            20                  25

<210> SEQ ID NO 44
<211> LENGTH: 27
<212> TYPE: PRT
<213> ORGANISM: Artificial Sequence
<220> FEATURE:
<223> OTHER INFORMATION: human cytomegalovirus glycoprotein B peptide

<400> SEQUENCE: 44

Trp Arg Ile His His Ile Asn Lys Phe Ala Gln Ala Tyr Ser Ser Tyr
 1               5                  10                  15

Ser Arg Val Ile Gly Gly Thr Val Phe Val Ala
            20                  25

<210> SEQ ID NO 45
<211> LENGTH: 27
<212> TYPE: PRT
<213> ORGANISM: Artificial Sequence
<220> FEATURE:
<223> OTHER INFORMATION: human cytomegalovirus glycoprotein B peptide

<400> SEQUENCE: 45

Trp Glu Ile Asp His Ile Asn Lys Phe Ala Gln Ala Tyr Ser Ser Tyr
 1               5                  10                  15

Ser Arg Val Ile Gly Gly Thr Val Phe Val Ala
            20                  25

<210> SEQ ID NO 46
<211> LENGTH: 27
<212> TYPE: PRT
<213> ORGANISM: Artificial Sequence
<220> FEATURE:
<223> OTHER INFORMATION: human cytomegalovirus glycoprotein B peptide

<400> SEQUENCE: 46

Trp Glu Ile His Glu Ile Asn Lys Phe Ala Gln Ala Tyr Ser Ser Tyr
 1               5                  10                  15

Ser Arg Val Ile Gly Gly Thr Val Phe Val Ala
            20                  25

<210> SEQ ID NO 47
<211> LENGTH: 27
<212> TYPE: PRT
<213> ORGANISM: Artificial Sequence
<220> FEATURE:
<223> OTHER INFORMATION: human cytomegalovirus glycoprotein B peptide

<400> SEQUENCE: 47

Trp Glu Ile His His Ile Asn Glu Phe Ala Gln Ala Tyr Ser Ser Tyr
 1               5                  10                  15

Ser Arg Val Ile Gly Gly Thr Val Phe Val Ala
            20                  25

<210> SEQ ID NO 48
<211> LENGTH: 27
<212> TYPE: PRT
<213> ORGANISM: Artificial Sequence
<220> FEATURE:
<223> OTHER INFORMATION: human cytomegalovirus glycoprotein B peptide
```

```
<400> SEQUENCE: 48

Trp Glu Ile His His Ile Asn Lys Phe Ala Gln Ala Tyr Ser Ser Tyr
1               5                   10                  15

Ser Asp Val Ile Gly Gly Thr Val Phe Val Ala
            20                  25

<210> SEQ ID NO 49
<211> LENGTH: 31
<212> TYPE: PRT
<213> ORGANISM: Artificial Sequence
<220> FEATURE:
<223> OTHER INFORMATION: human cytomegalovirus glycoprotein B peptide

<400> SEQUENCE: 49

Trp His Ser Arg Gly Ser Thr Trp Leu Tyr Arg Glu Thr Cys Asn Leu
1               5                   10                  15

Asn Cys Met Leu Thr Ile Thr Thr Ala Arg Ser Lys Tyr Pro Tyr
            20                  25                  30

<210> SEQ ID NO 50
<211> LENGTH: 59
<212> TYPE: PRT
<213> ORGANISM: Artificial Sequence
<220> FEATURE:
<223> OTHER INFORMATION: human cytomegalovirus glycoprotein B peptide

<400> SEQUENCE: 50

Ser Asn Thr His Ser Thr Arg Tyr Val Thr Val Lys Asp Gln Trp His
1               5                   10                  15

Ser Arg Gly Ser Thr Trp Leu Tyr Arg Glu Thr Cys Asn Leu Asn Cys
            20                  25                  30

Met Leu Thr Ile Thr Thr Ala Arg Ser Lys Tyr Pro Tyr His Phe Phe
        35                  40                  45

Ala Thr Ser Thr Gly Asp Val Val Tyr Ile Ser
    50                  55

<210> SEQ ID NO 51
<211> LENGTH: 56
<212> TYPE: PRT
<213> ORGANISM: Artificial Sequence
<220> FEATURE:
<223> OTHER INFORMATION: human cytomegalovirus glycoprotein B peptide

<400> SEQUENCE: 51

Ser Asn Thr His Ser Thr Arg Tyr Val Thr Val Lys Asp Gln Trp His
1               5                   10                  15

Ser Arg Gly Ser Thr Trp Leu Tyr Arg Glu Thr Cys Asn Leu Asn Cys
            20                  25                  30

Met Leu Thr Ile Thr Thr Ala Arg Ser Lys Tyr Pro Tyr His Phe Phe
        35                  40                  45

Ala Thr Ser Thr Gly Asp Val Val
    50                  55

<210> SEQ ID NO 52
<211> LENGTH: 53
<212> TYPE: PRT
<213> ORGANISM: Artificial Sequence
<220> FEATURE:
<223> OTHER INFORMATION: human cytomegalovirus glycoprotein B peptide

<400> SEQUENCE: 52
```

-continued

Ser Asn Thr His Ser Thr Arg Tyr Val Thr Val Lys Asp Gln Trp His
1               5                   10                  15

Ser Arg Gly Ser Thr Trp Leu Tyr Arg Glu Thr Cys Asn Leu Asn Cys
            20                  25                  30

Met Leu Thr Ile Thr Thr Ala Arg Ser Lys Tyr Pro Tyr His Phe Phe
        35                  40                  45

Ala Thr Ser Thr Gly
        50

<210> SEQ ID NO 53
<211> LENGTH: 50
<212> TYPE: PRT
<213> ORGANISM: Artificial Sequence
<220> FEATURE:
<223> OTHER INFORMATION: human cytomegalovirus glycoprotein B peptide

<400> SEQUENCE: 53

Ser Asn Thr His Ser Thr Arg Tyr Val Thr Val Lys Asp Gln Trp His
1               5                   10                  15

Ser Arg Gly Ser Thr Trp Leu Tyr Arg Glu Thr Cys Asn Leu Asn Cys
            20                  25                  30

Met Leu Thr Ile Thr Thr Ala Arg Ser Lys Tyr Pro Tyr His Phe Phe
        35                  40                  45

Ala Thr
    50

<210> SEQ ID NO 54
<211> LENGTH: 47
<212> TYPE: PRT
<213> ORGANISM: Artificial Sequence
<220> FEATURE:
<223> OTHER INFORMATION: human cytomegalovirus glycoprotein B peptide

<400> SEQUENCE: 54

Ser Asn Thr His Ser Thr Arg Tyr Val Thr Val Lys Asp Gln Trp His
1               5                   10                  15

Ser Arg Gly Ser Thr Trp Leu Tyr Arg Glu Thr Cys Asn Leu Asn Cys
            20                  25                  30

Met Leu Thr Ile Thr Thr Ala Arg Ser Lys Tyr Pro Tyr His Phe
        35                  40                  45

<210> SEQ ID NO 55
<211> LENGTH: 44
<212> TYPE: PRT
<213> ORGANISM: Artificial Sequence
<220> FEATURE:
<223> OTHER INFORMATION: human cytomegalovirus glycoprotein B peptide

<400> SEQUENCE: 55

Ser Asn Thr His Ser Thr Arg Tyr Val Thr Val Lys Asp Gln Trp His
1               5                   10                  15

Ser Arg Gly Ser Thr Trp Leu Tyr Arg Glu Thr Cys Asn Leu Asn Cys
            20                  25                  30

Met Leu Thr Ile Thr Thr Ala Arg Ser Lys Tyr Pro
        35                  40

<210> SEQ ID NO 56
<211> LENGTH: 41
<212> TYPE: PRT
<213> ORGANISM: Artificial Sequence
<220> FEATURE:
<223> OTHER INFORMATION: human cytomegalovirus glycoprotein B peptide

```
<400> SEQUENCE: 56

Ser Asn Thr His Ser Thr Arg Tyr Val Thr Val Lys Asp Gln Trp His
1               5                   10                  15

Ser Arg Gly Ser Thr Trp Leu Tyr Arg Glu Thr Cys Asn Leu Asn Cys
            20                  25                  30

Met Leu Thr Ile Thr Thr Ala Arg Ser
        35                  40

<210> SEQ ID NO 57
<211> LENGTH: 38
<212> TYPE: PRT
<213> ORGANISM: Artificial Sequence
<220> FEATURE:
<223> OTHER INFORMATION: human cytomegalovirus glycoprotein B peptide

<400> SEQUENCE: 57

Ser Asn Thr His Ser Thr Arg Tyr Val Thr Val Lys Asp Gln Trp His
1               5                   10                  15

Ser Arg Gly Ser Thr Trp Leu Tyr Arg Glu Thr Cys Asn Leu Asn Cys
            20                  25                  30

Met Leu Thr Ile Thr Thr
        35

<210> SEQ ID NO 58
<211> LENGTH: 56
<212> TYPE: PRT
<213> ORGANISM: Artificial Sequence
<220> FEATURE:
<223> OTHER INFORMATION: human cytomegalovirus glycoprotein B peptide

<400> SEQUENCE: 58

His Ser Thr Arg Tyr Val Thr Val Lys Asp Gln Trp His Ser Arg Gly
1               5                   10                  15

Ser Thr Trp Leu Tyr Arg Glu Thr Cys Asn Leu Asn Cys Met Leu Thr
            20                  25                  30

Ile Thr Thr Ala Arg Ser Lys Tyr Pro Tyr His Phe Phe Ala Thr Ser
        35                  40                  45

Thr Gly Asp Val Val Tyr Ile Ser
    50                  55

<210> SEQ ID NO 59
<211> LENGTH: 53
<212> TYPE: PRT
<213> ORGANISM: Artificial Sequence
<220> FEATURE:
<223> OTHER INFORMATION: human cytomegalovirus glycoprotein B peptide

<400> SEQUENCE: 59

Arg Tyr Val Thr Val Lys Asp Gln Trp His Ser Arg Gly Ser Thr Trp
1               5                   10                  15

Leu Tyr Arg Glu Thr Cys Asn Leu Asn Cys Met Leu Thr Ile Thr Thr
            20                  25                  30

Ala Arg Ser Lys Tyr Pro Tyr His Phe Phe Ala Thr Ser Thr Gly Asp
        35                  40                  45

Val Val Tyr Ile Ser
    50

<210> SEQ ID NO 60
<211> LENGTH: 50
<212> TYPE: PRT
```

-continued

```
<213> ORGANISM: Artificial Sequence
<220> FEATURE:
<223> OTHER INFORMATION: human cytomegalovirus glycoprotein B peptide

<400> SEQUENCE: 60

Thr Val Lys Asp Gln Trp His Ser Arg Gly Ser Thr Trp Leu Tyr Arg
 1               5                  10                  15

Glu Thr Cys Asn Leu Asn Cys Met Leu Thr Ile Thr Thr Ala Arg Ser
                20                  25                  30

Lys Tyr Pro Tyr His Phe Phe Ala Thr Ser Thr Gly Asp Val Val Tyr
            35                  40                  45

Ile Ser
    50

<210> SEQ ID NO 61
<211> LENGTH: 47
<212> TYPE: PRT
<213> ORGANISM: Artificial Sequence
<220> FEATURE:
<223> OTHER INFORMATION: human cytomegalovirus glycoprotein B peptide

<400> SEQUENCE: 61

Asp Gln Trp His Ser Arg Gly Ser Thr Trp Leu Tyr Arg Glu Thr Cys
 1               5                  10                  15

Asn Leu Asn Cys Met Leu Thr Ile Thr Thr Ala Arg Ser Lys Tyr Pro
                20                  25                  30

Tyr His Phe Phe Ala Thr Ser Thr Gly Asp Val Val Tyr Ile Ser
            35                  40                  45

<210> SEQ ID NO 62
<211> LENGTH: 44
<212> TYPE: PRT
<213> ORGANISM: Artificial Sequence
<220> FEATURE:
<223> OTHER INFORMATION: human cytomegalovirus glycoprotein B peptide

<400> SEQUENCE: 62

His Ser Arg Gly Ser Thr Trp Leu Tyr Arg Glu Thr Cys Asn Leu Asn
 1               5                  10                  15

Cys Met Leu Thr Ile Thr Thr Ala Arg Ser Lys Tyr Pro Tyr His Phe
                20                  25                  30

Phe Ala Thr Ser Thr Gly Asp Val Val Tyr Ile Ser
            35                  40

<210> SEQ ID NO 63
<211> LENGTH: 41
<212> TYPE: PRT
<213> ORGANISM: Artificial Sequence
<220> FEATURE:
<223> OTHER INFORMATION: human cytomegalovirus glycoprotein B peptide

<400> SEQUENCE: 63

Gly Ser Thr Trp Leu Tyr Arg Glu Thr Cys Asn Leu Asn Cys Met Leu
 1               5                  10                  15

Thr Ile Thr Thr Ala Arg Ser Lys Tyr Pro Tyr His Phe Phe Ala Thr
                20                  25                  30

Ser Thr Gly Asp Val Val Tyr Ile Ser
            35                  40

<210> SEQ ID NO 64
<211> LENGTH: 38
<212> TYPE: PRT
```

<210> SEQ ID NO 65
<211> LENGTH: 38
<212> TYPE: PRT
<213> ORGANISM: Artificial Sequence
<220> FEATURE:
<223> OTHER INFORMATION: human cytomegalovirus glycoprotein B peptide

<400> SEQUENCE: 64

Trp Leu Tyr Arg Glu Thr Cys Asn Leu Asn Cys Met Leu Thr Ile Thr
1               5                   10                  15

Thr Ala Arg Ser Lys Tyr Pro Tyr His Phe Phe Ala Thr Ser Thr Gly
            20                  25                  30

Asp Val Val Tyr Ile Ser
        35

<210> SEQ ID NO 65
<211> LENGTH: 38
<212> TYPE: PRT
<213> ORGANISM: Artificial Sequence
<220> FEATURE:
<223> OTHER INFORMATION: human cytomegalovirus glycoprotein B peptide

<400> SEQUENCE: 65

Trp Leu Tyr Arg Glu Thr Cys Asn Leu Asn Cys Met Leu Thr Ile Thr
1               5                   10                  15

Thr Ala Arg Ser Lys Tyr Pro Tyr His Phe Phe Ala Thr Ser Thr Gly
            20                  25                  30

Asp Val Val Tyr Ile Ser
        35

<210> SEQ ID NO 66
<211> LENGTH: 31
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 31
<223> OTHER INFORMATION: Tyr 31 fused to human serum albumin

<400> SEQUENCE: 66

Trp His Ser Arg Gly Ser Thr Trp Leu Tyr Arg Glu Thr Ala Asn Leu
1               5                   10                  15

Asn Ala Met Leu Thr Ile Thr Thr Ala Arg Ser Lys Tyr Pro Tyr
            20                  25                  30

<210> SEQ ID NO 67
<211> LENGTH: 42
<212> TYPE: PRT
<213> ORGANISM: Artificial Sequence
<220> FEATURE:
<223> OTHER INFORMATION: human cytomegalovirus glycoprotein B peptide

<400> SEQUENCE: 67

Trp His Ser Arg Gly Ser Thr Trp Leu Tyr Arg Glu Thr Ala Asn Leu
1               5                   10                  15

Asn Ala Met Leu Thr Ile Thr Thr Ala Arg Ser Lys Tyr Pro Tyr Gly
            20                  25                  30

Arg Lys Lys Arg Arg Gln Arg Arg Pro
        35                  40

<210> SEQ ID NO 68
<211> LENGTH: 40
<212> TYPE: PRT
<213> ORGANISM: Artificial Sequence
<220> FEATURE:
<223> OTHER INFORMATION: human cytomegalovirus glycoprotein B peptide

<400> SEQUENCE: 68

Trp His Ser Arg Gly Ser Thr Trp Leu Tyr Arg Glu Thr Ala Asn Leu
1               5                   10                  15

Asn Ala Met Leu Thr Ile Thr Thr Ala Arg Ser Lys Tyr Pro Tyr Arg
            20                  25                  30

Arg Arg Arg Arg Arg Arg Arg Arg
        35                  40

<210> SEQ ID NO 69
<211> LENGTH: 40
<212> TYPE: PRT
<213> ORGANISM: Artificial Sequence
<220> FEATURE:
<223> OTHER INFORMATION: human cytomegalovirus glycoprotein B peptide

<400> SEQUENCE: 69

Trp His Ser Arg Gly Ser Thr Trp Leu Tyr Arg Glu Thr Ala Asn Leu
1               5                   10                  15

Asn Ala Met Leu Thr Ile Thr Thr Ala Arg Ser Lys Tyr Pro Tyr Ala
            20                  25                  30

Ser Lys Ser Lys Ser Lys Ser Lys
        35                  40

<210> SEQ ID NO 70
<211> LENGTH: 32
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 32
<223> OTHER INFORMATION: D-Pro

<400> SEQUENCE: 70

Trp His Ser Arg Gly Ser Thr Trp Leu Tyr Arg Glu Thr Ala Asn Leu
1               5                   10                  15

Asn Ala Met Leu Thr Ile Thr Thr Ala Arg Ser Lys Tyr Pro Tyr Pro
            20                  25                  30

<210> SEQ ID NO 71
<211> LENGTH: 31
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 1
<223> OTHER INFORMATION: N-myristoyl

<400> SEQUENCE: 71

Trp His Ser Arg Gly Ser Thr Trp Leu Tyr Arg Glu Thr Ala Asn Leu
1               5                   10                  15

Asn Ala Met Leu Thr Ile Thr Thr Ala Arg Ser Lys Tyr Pro Tyr
            20                  25                  30

<210> SEQ ID NO 72
<211> LENGTH: 31
<212> TYPE: PRT
<213> ORGANISM: Artificial Sequence
<220> FEATURE:
<223> OTHER INFORMATION: human cytomegalovirus glycoprotein B peptide
<221> NAME/KEY: LIPID
<222> LOCATION: 31
<223> OTHER INFORMATION: Cholesterol ester

```
<400> SEQUENCE: 72

Trp His Ser Arg Gly Ser Thr Trp Leu Tyr Arg Glu Thr Ala Asn Leu
1               5                   10                  15

Asn Ala Met Leu Thr Ile Thr Thr Ala Arg Ser Lys Tyr Pro Tyr
            20                  25                  30

<210> SEQ ID NO 73
<211> LENGTH: 31
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 31
<223> OTHER INFORMATION: polyethylene glycol derivative

<400> SEQUENCE: 73

Trp His Ser Arg Gly Ser Thr Trp Leu Tyr Arg Glu Thr Ala Asn Leu
1               5                   10                  15

Asn Ala Met Leu Thr Ile Thr Thr Ala Arg Ser Lys Tyr Pro Tyr
            20                  25                  30

<210> SEQ ID NO 74
<211> LENGTH: 33
<212> TYPE: PRT
<213> ORGANISM: Artificial Sequence
<220> FEATURE:
<223> OTHER INFORMATION: heterodetic cyclic human cytomegalovirus
      glycoprotein B peptide
<221> NAME/KEY: DISULFID
<222> LOCATION: 1, 33
<223> OTHER INFORMATION: disulfide bridge between Cys1 and Cys33

<400> SEQUENCE: 74

Cys Trp His Ser Arg Gly Ser Thr Trp Leu Tyr Arg Glu Thr Ala Asn
1               5                   10                  15

Leu Asn Ala Met Leu Thr Ile Thr Thr Ala Arg Ser Lys Tyr Pro Tyr
            20                  25                  30

Cys

<210> SEQ ID NO 75
<211> LENGTH: 31
<212> TYPE: PRT
<213> ORGANISM: Artificial Sequence
<220> FEATURE:
<223> OTHER INFORMATION: human cytomegalovirus glycoprotein B peptide

<400> SEQUENCE: 75

Trp Asp Ser Arg Gly Ser Thr Trp Leu Tyr Arg Glu Thr Ala Asn Leu
1               5                   10                  15

Asn Ala Met Leu Thr Ile Thr Thr Ala Arg Ser Lys Tyr Pro Tyr
            20                  25                  30

<210> SEQ ID NO 76
<211> LENGTH: 31
<212> TYPE: PRT
<213> ORGANISM: Artificial Sequence
<220> FEATURE:
<223> OTHER INFORMATION: human cytomegalovirus glycoprotein B peptide

<400> SEQUENCE: 76

Trp His Ser Glu Gly Ser Thr Trp Leu Tyr Arg Glu Thr Ala Asn Leu
1               5                   10                  15
```

Asn Ala Met Leu Thr Ile Thr Thr Ala Arg Ser Lys Tyr Pro Tyr
            20                  25                  30

<210> SEQ ID NO 77
<211> LENGTH: 31
<212> TYPE: PRT
<213> ORGANISM: Artificial Sequence
<220> FEATURE:
<223> OTHER INFORMATION: human cytomegalovirus glycoprotein B peptide

<400> SEQUENCE: 77

Trp His Ser Arg Gly Ser Thr Trp Leu Tyr Glu Glu Thr Ala Asn Leu
1               5                   10                  15

Asn Ala Met Leu Thr Ile Thr Thr Ala Arg Ser Lys Tyr Pro Tyr
            20                  25                  30

<210> SEQ ID NO 78
<211> LENGTH: 31
<212> TYPE: PRT
<213> ORGANISM: Artificial Sequence
<220> FEATURE:
<223> OTHER INFORMATION: human cytomegalovirus glycoprotein B peptide

<400> SEQUENCE: 78

Trp His Ser Arg Gly Ser Thr Trp Leu Tyr Arg Arg Thr Ala Asn Leu
1               5                   10                  15

Asn Ala Met Leu Thr Ile Thr Thr Ala Arg Ser Lys Tyr Pro Tyr
            20                  25                  30

<210> SEQ ID NO 79
<211> LENGTH: 31
<212> TYPE: PRT
<213> ORGANISM: Artificial Sequence
<220> FEATURE:
<223> OTHER INFORMATION: human cytomegalovirus glycoprotein B peptide

<400> SEQUENCE: 79

Trp His Ser Arg Gly Ser Thr Trp Leu Tyr Arg Glu Thr Ala Asn Leu
1               5                   10                  15

Asn Ala Met Leu Thr Ile Thr Thr Ala Asp Ser Lys Tyr Pro Tyr
            20                  25                  30

<210> SEQ ID NO 80
<211> LENGTH: 31
<212> TYPE: PRT
<213> ORGANISM: Artificial Sequence
<220> FEATURE:
<223> OTHER INFORMATION: human cytomegalovirus glycoprotein B peptide

<400> SEQUENCE: 80

Trp His Ser Arg Gly Ser Thr Trp Leu Tyr Arg Glu Thr Ala Asn Leu
1               5                   10                  15

Asn Ala Met Leu Thr Ile Thr Thr Ala Arg Ser Glu Tyr Pro Tyr
            20                  25                  30

<210> SEQ ID NO 81
<211> LENGTH: 56
<212> TYPE: PRT
<213> ORGANISM: Artificial Sequence
<220> FEATURE:
<223> OTHER INFORMATION: human cytomegalovirus glycoprotein B peptide

<400> SEQUENCE: 81

Cys Met Leu Thr Ile Thr Thr Ala Arg Ser Lys Tyr Pro Tyr His Phe
1               5                   10                  15

```
Phe Ala Thr Ser Thr Gly Asp Val Val Tyr Ile Ser Pro Phe Tyr Asn
            20                  25                  30

Gly Thr Asn Arg Asn Ala Ser Tyr Phe Gly Glu Asn Ala Asp Lys Phe
        35                  40                  45

Phe Ile Phe Pro Asn Tyr Thr Ile
    50                  55

<210> SEQ ID NO 82
<211> LENGTH: 53
<212> TYPE: PRT
<213> ORGANISM: Artificial Sequence
<220> FEATURE:
<223> OTHER INFORMATION: human cytomegalovirus glycoprotein B peptide

<400> SEQUENCE: 82

Cys Met Leu Thr Ile Thr Thr Ala Arg Ser Lys Tyr Pro Tyr His Phe
1               5                   10                  15

Phe Ala Thr Ser Thr Gly Asp Val Val Tyr Ile Ser Pro Phe Tyr Asn
            20                  25                  30

Gly Thr Asn Arg Asn Ala Ser Tyr Phe Gly Glu Asn Ala Asp Lys Phe
        35                  40                  45

Phe Ile Phe Pro Asn
    50

<210> SEQ ID NO 83
<211> LENGTH: 50
<212> TYPE: PRT
<213> ORGANISM: Artificial Sequence
<220> FEATURE:
<223> OTHER INFORMATION: human cytomegalovirus glycoprotein B peptide

<400> SEQUENCE: 83

Cys Met Leu Thr Ile Thr Thr Ala Arg Ser Lys Tyr Pro Tyr His Phe
1               5                   10                  15

Phe Ala Thr Ser Thr Gly Asp Val Val Tyr Ile Ser Pro Phe Tyr Asn
            20                  25                  30

Gly Thr Asn Arg Asn Ala Ser Tyr Phe Gly Glu Asn Ala Asp Lys Phe
        35                  40                  45

Phe Ile
    50

<210> SEQ ID NO 84
<211> LENGTH: 47
<212> TYPE: PRT
<213> ORGANISM: Artificial Sequence
<220> FEATURE:
<223> OTHER INFORMATION: human cytomegalovirus glycoprotein B peptide

<400> SEQUENCE: 84

Cys Met Leu Thr Ile Thr Thr Ala Arg Ser Lys Tyr Pro Tyr His Phe
1               5                   10                  15

Phe Ala Thr Ser Thr Gly Asp Val Val Tyr Ile Ser Pro Phe Tyr Asn
            20                  25                  30

Gly Thr Asn Arg Asn Ala Ser Tyr Phe Gly Glu Asn Ala Asp Lys
        35                  40                  45

<210> SEQ ID NO 85
<211> LENGTH: 44
<212> TYPE: PRT
<213> ORGANISM: Artificial Sequence
<220> FEATURE:
```

<223> OTHER INFORMATION: human cytomegalovirus glycoprotein B peptide

<400> SEQUENCE: 85

Cys Met Leu Thr Ile Thr Thr Ala Arg Ser Lys Tyr Pro Tyr His Phe
1               5                   10                  15

Phe Ala Thr Ser Thr Gly Asp Val Val Tyr Ile Ser Pro Phe Tyr Asn
            20                  25                  30

Gly Thr Asn Arg Asn Ala Ser Tyr Phe Gly Glu Asn
        35                  40

<210> SEQ ID NO 86
<211> LENGTH: 41
<212> TYPE: PRT
<213> ORGANISM: Artificial Sequence
<220> FEATURE:
<223> OTHER INFORMATION: human cytomegalovirus glycoprotein B peptide

<400> SEQUENCE: 86

Cys Met Leu Thr Ile Thr Thr Ala Arg Ser Lys Tyr Pro Tyr His Phe
1               5                   10                  15

Phe Ala Thr Ser Thr Gly Asp Val Val Tyr Ile Ser Pro Phe Tyr Asn
            20                  25                  30

Gly Thr Asn Arg Asn Ala Ser Tyr Phe
        35                  40

<210> SEQ ID NO 87
<211> LENGTH: 38
<212> TYPE: PRT
<213> ORGANISM: Artificial Sequence
<220> FEATURE:
<223> OTHER INFORMATION: human cytomegalovirus glycoprotein B peptide

<400> SEQUENCE: 87

Cys Met Leu Thr Ile Thr Thr Ala Arg Ser Lys Tyr Pro Tyr His Phe
1               5                   10                  15

Phe Ala Thr Ser Thr Gly Asp Val Val Tyr Ile Ser Pro Phe Tyr Asn
            20                  25                  30

Gly Thr Asn Arg Asn Ala
        35

<210> SEQ ID NO 88
<211> LENGTH: 35
<212> TYPE: PRT
<213> ORGANISM: Artificial Sequence
<220> FEATURE:
<223> OTHER INFORMATION: human cytomegalovirus glycoprotein B peptide

<400> SEQUENCE: 88

Cys Met Leu Thr Ile Thr Thr Ala Arg Ser Lys Tyr Pro Tyr His Phe
1               5                   10                  15

Phe Ala Thr Ser Thr Gly Asp Val Val Tyr Ile Ser Pro Phe Tyr Asn
            20                  25                  30

Gly Thr Asn
        35

<210> SEQ ID NO 89
<211> LENGTH: 53
<212> TYPE: PRT
<213> ORGANISM: Artificial Sequence
<220> FEATURE:
<223> OTHER INFORMATION: human cytomegalovirus glycoprotein B peptide

<400> SEQUENCE: 89

Thr Ile Thr Thr Ala Arg Ser Lys Tyr Pro Tyr His Phe Phe Ala Thr
1               5                   10                  15

Ser Thr Gly Asp Val Val Tyr Ile Ser Pro Phe Tyr Asn Gly Thr Asn
            20                  25                  30

Arg Asn Ala Ser Tyr Phe Gly Glu Asn Ala Asp Lys Phe Phe Ile Phe
        35                  40                  45

Pro Asn Tyr Thr Ile
        50

<210> SEQ ID NO 90
<211> LENGTH: 50
<212> TYPE: PRT
<213> ORGANISM: Artificial Sequence
<220> FEATURE:
<223> OTHER INFORMATION: human cytomegalovirus glycoprotein B peptide

<400> SEQUENCE: 90

Thr Ala Arg Ser Lys Tyr Pro Tyr His Phe Phe Ala Thr Ser Thr Gly
1               5                   10                  15

Asp Val Val Tyr Ile Ser Pro Phe Tyr Asn Gly Thr Asn Arg Asn Ala
            20                  25                  30

Ser Tyr Phe Gly Glu Asn Ala Asp Lys Phe Phe Ile Phe Pro Asn Tyr
        35                  40                  45

Thr Ile
    50

<210> SEQ ID NO 91
<211> LENGTH: 47
<212> TYPE: PRT
<213> ORGANISM: Artificial Sequence
<220> FEATURE:
<223> OTHER INFORMATION: human cytomegalovirus glycoprotein B peptide

<400> SEQUENCE: 91

Ser Lys Tyr Pro Tyr His Phe Phe Ala Thr Ser Thr Gly Asp Val Val
1               5                   10                  15

Tyr Ile Ser Pro Phe Tyr Asn Gly Thr Asn Arg Asn Ala Ser Tyr Phe
            20                  25                  30

Gly Glu Asn Ala Asp Lys Phe Phe Ile Phe Pro Asn Tyr Thr Ile
        35                  40                  45

<210> SEQ ID NO 92
<211> LENGTH: 44
<212> TYPE: PRT
<213> ORGANISM: Artificial Sequence
<220> FEATURE:
<223> OTHER INFORMATION: human cytomegalovirus glycoprotein B peptide

<400> SEQUENCE: 92

Pro Tyr His Phe Phe Ala Thr Ser Thr Gly Asp Val Val Tyr Ile Ser
1               5                   10                  15

Pro Phe Tyr Asn Gly Thr Asn Arg Asn Ala Ser Tyr Phe Gly Glu Asn
            20                  25                  30

Ala Asp Lys Phe Phe Ile Phe Pro Asn Tyr Thr Ile
        35                  40

<210> SEQ ID NO 93
<211> LENGTH: 41
<212> TYPE: PRT
<213> ORGANISM: Artificial Sequence
<220> FEATURE:

<223> OTHER INFORMATION: human cytomegalovirus glycoprotein B peptide

<400> SEQUENCE: 93

Phe Phe Ala Thr Ser Thr Gly Asp Val Val Tyr Ile Ser Pro Phe Tyr
1               5                   10                  15

Asn Gly Thr Asn Arg Asn Ala Ser Tyr Phe Gly Glu Asn Ala Asp Lys
            20                  25                  30

Phe Phe Ile Phe Pro Asn Tyr Thr Ile
        35                  40

<210> SEQ ID NO 94
<211> LENGTH: 38
<212> TYPE: PRT
<213> ORGANISM: Artificial Sequence
<220> FEATURE:
<223> OTHER INFORMATION: human cytomegalovirus glycoprotein B peptide

<400> SEQUENCE: 94

Thr Ser Thr Gly Asp Val Val Tyr Ile Ser Pro Phe Tyr Asn Gly Thr
1               5                   10                  15

Asn Arg Asn Ala Ser Tyr Phe Gly Glu Asn Ala Asp Lys Phe Phe Ile
            20                  25                  30

Phe Pro Asn Tyr Thr Ile
        35

<210> SEQ ID NO 95
<211> LENGTH: 35
<212> TYPE: PRT
<213> ORGANISM: Artificial Sequence
<220> FEATURE:
<223> OTHER INFORMATION: human cytomegalovirus glycoprotein B peptide

<400> SEQUENCE: 95

Gly Asp Val Val Tyr Ile Ser Pro Phe Tyr Asn Gly Thr Asn Arg Asn
1               5                   10                  15

Ala Ser Tyr Phe Gly Glu Asn Ala Asp Lys Phe Phe Ile Phe Pro Asn
            20                  25                  30

Tyr Thr Ile
        35

<210> SEQ ID NO 96
<211> LENGTH: 32
<212> TYPE: PRT
<213> ORGANISM: Artificial Sequence
<220> FEATURE:
<223> OTHER INFORMATION: human cytomegalovirus glycoprotein B peptide

<400> SEQUENCE: 96

Val Tyr Ile Ser Pro Phe Tyr Asn Gly Thr Asn Arg Asn Ala Ser Tyr
1               5                   10                  15

Phe Gly Glu Asn Ala Asp Lys Phe Phe Ile Phe Pro Asn Tyr Thr Ile
            20                  25                  30

<210> SEQ ID NO 97
<211> LENGTH: 28
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 28
<223> OTHER INFORMATION: Gly 28 fused to human serum albumin

<400> SEQUENCE: 97

```
His Phe Phe Ala Thr Ser Thr Gly Asp Val Val Tyr Ile Ser Pro Phe
 1               5                  10                  15

Tyr Asn Gly Thr Asn Arg Asn Ala Ser Tyr Phe Gly
             20                  25
```

<210> SEQ ID NO 98
<211> LENGTH: 39
<212> TYPE: PRT
<213> ORGANISM: Artificial Sequence
<220> FEATURE:
<223> OTHER INFORMATION: human cytomegalovirus glycoprotein B peptide

<400> SEQUENCE: 98

```
His Phe Phe Ala Thr Ser Thr Gly Asp Val Val Tyr Ile Ser Pro Phe
 1               5                  10                  15

Tyr Asn Gly Thr Asn Arg Asn Ala Ser Tyr Phe Gly Gly Arg Lys Lys
             20                  25                  30

Arg Arg Gln Arg Arg Pro
             35
```

<210> SEQ ID NO 99
<211> LENGTH: 37
<212> TYPE: PRT
<213> ORGANISM: Artificial Sequence
<220> FEATURE:
<223> OTHER INFORMATION: human cytomegalovirus glycoprotein B peptide

<400> SEQUENCE: 99

```
His Phe Phe Ala Thr Ser Thr Gly Asp Val Val Tyr Ile Ser Pro Phe
 1               5                  10                  15

Tyr Asn Gly Thr Asn Arg Asn Ala Ser Tyr Phe Gly Arg Arg Arg Arg
             20                  25                  30

Arg Arg Arg Arg Arg
             35
```

<210> SEQ ID NO 100
<211> LENGTH: 37
<212> TYPE: PRT
<213> ORGANISM: Artificial Sequence
<220> FEATURE:
<223> OTHER INFORMATION: human cytomegalovirus glycoprotein B peptide

<400> SEQUENCE: 100

```
His Phe Phe Ala Thr Ser Thr Gly Asp Val Val Tyr Ile Ser Pro Phe
 1               5                  10                  15

Tyr Asn Gly Thr Asn Arg Asn Ala Ser Tyr Phe Gly Ala Ser Lys Ser
             20                  25                  30

Lys Ser Lys Ser Lys
             35
```

<210> SEQ ID NO 101
<211> LENGTH: 29
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 29
<223> OTHER INFORMATION: D-Pro

<400> SEQUENCE: 101

```
His Phe Phe Ala Thr Ser Thr Gly Asp Val Val Tyr Ile Ser Pro Phe
 1               5                  10                  15
```

Tyr Asn Gly Thr Asn Arg Asn Ala Ser Tyr Phe Gly Pro
            20                  25

<210> SEQ ID NO 102
<211> LENGTH: 28
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 1
<223> OTHER INFORMATION: N-myristoyl

<400> SEQUENCE: 102

His Phe Phe Ala Thr Ser Thr Gly Asp Val Val Tyr Ile Ser Pro Phe
1               5                   10                  15

Tyr Asn Gly Thr Asn Arg Asn Ala Ser Tyr Phe Gly
            20                  25

<210> SEQ ID NO 103
<211> LENGTH: 28
<212> TYPE: PRT
<213> ORGANISM: Artificial Sequence
<220> FEATURE:
<223> OTHER INFORMATION: human cytomegalovirus glycoprotein B peptide
<221> NAME/KEY: LIPID
<222> LOCATION: 28
<223> OTHER INFORMATION: Cholesterol ester

<400> SEQUENCE: 103

His Phe Phe Ala Thr Ser Thr Gly Asp Val Val Tyr Ile Ser Pro Phe
1               5                   10                  15

Tyr Asn Gly Thr Asn Arg Asn Ala Ser Tyr Phe Gly
            20                  25

<210> SEQ ID NO 104
<211> LENGTH: 28
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 28
<223> OTHER INFORMATION: polyethylene glycol derivative

<400> SEQUENCE: 104

His Phe Phe Ala Thr Ser Thr Gly Asp Val Val Tyr Ile Ser Pro Phe
1               5                   10                  15

Tyr Asn Gly Thr Asn Arg Asn Ala Ser Tyr Phe Gly
            20                  25

<210> SEQ ID NO 105
<211> LENGTH: 30
<212> TYPE: PRT
<213> ORGANISM: Artificial Sequence
<220> FEATURE:
<223> OTHER INFORMATION: heterodetic cyclic human cytomegalovirus
      glycoprotein B peptide
<221> NAME/KEY: DISULFID
<222> LOCATION: 1, 30
<223> OTHER INFORMATION: disulfide bridge between Cys1 and Cys30

<400> SEQUENCE: 105

Cys His Phe Phe Ala Thr Ser Thr Gly Asp Val Val Tyr Ile Ser Pro
1               5                   10                  15

Phe Tyr Asn Gly Thr Asn Arg Asn Ala Ser Tyr Phe Gly Cys

```
<210> SEQ ID NO 106
<211> LENGTH: 28
<212> TYPE: PRT
<213> ORGANISM: Artificial Sequence
<220> FEATURE:
<223> OTHER INFORMATION: human cytomegalovirus glycoprotein B peptide

<400> SEQUENCE: 106

Asp Phe Phe Ala Thr Ser Thr Gly Asp Val Val Tyr Ile Ser Pro Phe
1               5                   10                  15

Tyr Asn Gly Thr Asn Arg Asn Ala Ser Tyr Phe Gly
            20                  25

<210> SEQ ID NO 107
<211> LENGTH: 28
<212> TYPE: PRT
<213> ORGANISM: Artificial Sequence
<220> FEATURE:
<223> OTHER INFORMATION: human cytomegalovirus glycoprotein B peptide

<400> SEQUENCE: 107

His Phe Phe Ala Thr Ser Thr Gly Lys Val Val Tyr Ile Ser Pro Phe
1               5                   10                  15

Tyr Asn Gly Thr Asn Arg Asn Ala Ser Tyr Phe Gly
            20                  25

<210> SEQ ID NO 108
<211> LENGTH: 28
<212> TYPE: PRT
<213> ORGANISM: Artificial Sequence
<220> FEATURE:
<223> OTHER INFORMATION: human cytomegalovirus glycoprotein B peptide

<400> SEQUENCE: 108

His Phe Phe Ala Thr Ser Thr Gly Asp Val Val Tyr Ile Ser Pro Phe
1               5                   10                  15

Tyr Asn Gly Thr Asn Glu Asn Ala Ser Tyr Phe Gly
            20                  25

<210> SEQ ID NO 109
<211> LENGTH: 47
<212> TYPE: PRT
<213> ORGANISM: Artificial Sequence
<220> FEATURE:
<223> OTHER INFORMATION: human cytomegalovirus glycoprotein B peptide

<400> SEQUENCE: 109

Thr Asn Arg Asn Ala Ser Tyr Phe Gly Glu Asn Ala Asp Lys Phe Phe
1               5                   10                  15

Ile Phe Pro Asn Tyr Thr Ile Val Ser Asp Phe Gly Arg Pro Asn Ala
            20                  25                  30

Ala Pro Glu Thr His Arg Leu Val Ala Phe Leu Glu Arg Ala Asp
        35                  40                  45

<210> SEQ ID NO 110
<211> LENGTH: 44
<212> TYPE: PRT
<213> ORGANISM: Artificial Sequence
<220> FEATURE:
<223> OTHER INFORMATION: human cytomegalovirus glycoprotein B peptide

<400> SEQUENCE: 110
```

Thr Asn Arg Asn Ala Ser Tyr Phe Gly Glu Asn Ala Asp Lys Phe
1               5                   10                  15

Ile Phe Pro Asn Tyr Thr Ile Val Ser Asp Phe Gly Arg Pro Asn Ala
            20                  25                  30

Ala Pro Glu Thr His Arg Leu Val Ala Phe Leu Glu
        35                  40

<210> SEQ ID NO 111
<211> LENGTH: 41
<212> TYPE: PRT
<213> ORGANISM: Artificial Sequence
<220> FEATURE:
<223> OTHER INFORMATION: human cytomegalovirus glycoprotein B peptide

<400> SEQUENCE: 111

Thr Asn Arg Asn Ala Ser Tyr Phe Gly Glu Asn Ala Asp Lys Phe
1               5                   10                  15

Ile Phe Pro Asn Tyr Thr Ile Val Ser Asp Phe Gly Arg Pro Asn Ala
            20                  25                  30

Ala Pro Glu Thr His Arg Leu Val Ala
        35                  40

<210> SEQ ID NO 112
<211> LENGTH: 38
<212> TYPE: PRT
<213> ORGANISM: Artificial Sequence
<220> FEATURE:
<223> OTHER INFORMATION: human cytomegalovirus glycoprotein B peptide

<400> SEQUENCE: 112

Thr Asn Arg Asn Ala Ser Tyr Phe Gly Glu Asn Ala Asp Lys Phe
1               5                   10                  15

Ile Phe Pro Asn Tyr Thr Ile Val Ser Asp Phe Gly Arg Pro Asn Ala
            20                  25                  30

Ala Pro Glu Thr His Arg
        35

<210> SEQ ID NO 113
<211> LENGTH: 35
<212> TYPE: PRT
<213> ORGANISM: Artificial Sequence
<220> FEATURE:
<223> OTHER INFORMATION: human cytomegalovirus glycoprotein B peptide

<400> SEQUENCE: 113

Thr Asn Arg Asn Ala Ser Tyr Phe Gly Glu Asn Ala Asp Lys Phe
1               5                   10                  15

Ile Phe Pro Asn Tyr Thr Ile Val Ser Asp Phe Gly Arg Pro Asn Ala
            20                  25                  30

Ala Pro Glu
        35

<210> SEQ ID NO 114
<211> LENGTH: 35
<212> TYPE: PRT
<213> ORGANISM: Artificial Sequence
<220> FEATURE:
<223> OTHER INFORMATION: human cytomegalovirus glycoprotein B peptide

<400> SEQUENCE: 114

Thr Asn Glu Asn Ala Ser Tyr Phe Gly Glu Asn Ala Asp Lys Phe Phe
1               5                   10                  15

```
Ile Phe Pro Asn Tyr Thr Ile Val Ser Asp Phe Gly Arg Pro Asn Ala
            20                  25                  30

Ala Pro Glu
        35

<210> SEQ ID NO 115
<211> LENGTH: 32
<212> TYPE: PRT
<213> ORGANISM: Artificial Sequence
<220> FEATURE:
<223> OTHER INFORMATION: human cytomegalovirus glycoprotein B peptide

<400> SEQUENCE: 115

Thr Asn Arg Asn Ala Ser Tyr Phe Gly Glu Asn Ala Asp Lys Phe Phe
1               5                   10                  15

Ile Phe Pro Asn Tyr Thr Ile Val Ser Asp Phe Gly Arg Pro Asn Ala
            20                  25                  30

<210> SEQ ID NO 116
<211> LENGTH: 32
<212> TYPE: PRT
<213> ORGANISM: Artificial Sequence
<220> FEATURE:
<223> OTHER INFORMATION: human cytomegalovirus glycoprotein B peptide

<400> SEQUENCE: 116

Thr Asn Glu Asn Ala Ser Tyr Phe Gly Glu Asn Ala Asp Lys Phe Phe
1               5                   10                  15

Ile Phe Pro Asn Tyr Thr Ile Val Ser Asp Phe Gly Arg Pro Asn Ala
            20                  25                  30

<210> SEQ ID NO 117
<211> LENGTH: 44
<212> TYPE: PRT
<213> ORGANISM: Artificial Sequence
<220> FEATURE:
<223> OTHER INFORMATION: human cytomegalovirus glycoprotein B peptide

<400> SEQUENCE: 117

Asn Ala Ser Tyr Phe Gly Glu Asn Ala Asp Lys Phe Phe Ile Phe Pro
1               5                   10                  15

Asn Tyr Thr Ile Val Ser Asp Phe Gly Arg Pro Asn Ala Ala Pro Glu
            20                  25                  30

Thr His Arg Leu Val Ala Phe Leu Glu Arg Ala Asp
        35                  40

<210> SEQ ID NO 118
<211> LENGTH: 41
<212> TYPE: PRT
<213> ORGANISM: Artificial Sequence
<220> FEATURE:
<223> OTHER INFORMATION: human cytomegalovirus glycoprotein B peptide

<400> SEQUENCE: 118

Tyr Phe Gly Glu Asn Ala Asp Lys Phe Phe Ile Phe Pro Asn Tyr Thr
1               5                   10                  15

Ile Val Ser Asp Phe Gly Arg Pro Asn Ala Ala Pro Glu Thr His Arg
            20                  25                  30

Leu Val Ala Phe Leu Glu Arg Ala Asp
        35                  40

<210> SEQ ID NO 119
<211> LENGTH: 38
```

```
<212> TYPE: PRT
<213> ORGANISM: Artificial Sequence
<220> FEATURE:
<223> OTHER INFORMATION: human cytomegalovirus glycoprotein B peptide

<400> SEQUENCE: 119

Glu Asn Ala Asp Lys Phe Phe Ile Phe Pro Asn Tyr Thr Ile Val Ser
1               5                   10                  15

Asp Phe Gly Arg Pro Asn Ala Ala Pro Glu Thr His Arg Leu Val Ala
            20                  25                  30

Phe Leu Glu Arg Ala Asp
        35

<210> SEQ ID NO 120
<211> LENGTH: 19
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 1
<223> OTHER INFORMATION: N-myristoyl

<400> SEQUENCE: 120

Phe Phe Ile Phe Pro Asn Tyr Thr Ile Val Ser Asp Phe Gly Arg Pro
1               5                   10                  15

Asn Ala Ala

<210> SEQ ID NO 121
<211> LENGTH: 19
<212> TYPE: PRT
<213> ORGANISM: Artificial Sequence
<220> FEATURE:
<223> OTHER INFORMATION: human cytomegalovirus glycoprotein B peptide
<221> NAME/KEY: LIPID
<222> LOCATION: 19
<223> OTHER INFORMATION: Cholesterol ester

<400> SEQUENCE: 121

Phe Phe Ile Phe Pro Asn Tyr Thr Ile Val Ser Asp Phe Gly Arg Pro
1               5                   10                  15

Asn Ala Ala

<210> SEQ ID NO 122
<211> LENGTH: 19
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 19
<223> OTHER INFORMATION: polyethylene glycol derivative

<400> SEQUENCE: 122

Phe Phe Ile Phe Pro Asn Tyr Thr Ile Val Ser Asp Phe Gly Arg Pro
1               5                   10                  15

Asn Ala Ala

<210> SEQ ID NO 123
<211> LENGTH: 21
<212> TYPE: PRT
<213> ORGANISM: Artificial Sequence
<220> FEATURE:
<223> OTHER INFORMATION: heterodetic cyclic human cytomegalovirus
      glycoprotein B peptide
<221> NAME/KEY: DISULFID
```

```
<222> LOCATION: 1, 21
<223> OTHER INFORMATION: disulfide bridge between Cys1 and Cys21

<400> SEQUENCE: 123

Cys Phe Phe Ile Phe Pro Asn Tyr Thr Ile Val Ser Asp Phe Gly Arg
1               5                   10                  15

Pro Asn Ala Ala Cys
            20

<210> SEQ ID NO 124
<211> LENGTH: 19
<212> TYPE: PRT
<213> ORGANISM: Artificial Sequence
<220> FEATURE:
<223> OTHER INFORMATION: human cytomegalovirus glycoprotein B peptide

<400> SEQUENCE: 124

Phe Phe Ile Phe Pro Asn Tyr Thr Ile Val Ser Arg Phe Gly Arg Pro
1               5                   10                  15

Asn Ala Ala

<210> SEQ ID NO 125
<211> LENGTH: 19
<212> TYPE: PRT
<213> ORGANISM: Artificial Sequence
<220> FEATURE:
<223> OTHER INFORMATION: human cytomegalovirus glycoprotein B peptide

<400> SEQUENCE: 125

Phe Phe Ile Phe Pro Asn Tyr Thr Ile Val Ser Asp Phe Gly Glu Pro
1               5                   10                  15

Asn Ala Ala

<210> SEQ ID NO 126
<211> LENGTH: 19
<212> TYPE: PRT
<213> ORGANISM: Artificial Sequence
<220> FEATURE:
<223> OTHER INFORMATION: human cytomegalovirus glycoprotein B peptide

<400> SEQUENCE: 126

Phe Phe Ile Phe Pro Gln Tyr Thr Ile Val Ser Arg Phe Gly Arg Pro
1               5                   10                  15

Asn Ala Ala

<210> SEQ ID NO 127
<211> LENGTH: 19
<212> TYPE: PRT
<213> ORGANISM: Artificial Sequence
<220> FEATURE:
<223> OTHER INFORMATION: human cytomegalovirus glycoprotein B peptide

<400> SEQUENCE: 127

Phe Phe Ile Phe Pro Gln Tyr Thr Ile Val Ser Asp Phe Gly Glu Pro
1               5                   10                  15

Asn Ala Ala

<210> SEQ ID NO 128
<211> LENGTH: 19
<212> TYPE: PRT
<213> ORGANISM: Artificial Sequence
<220> FEATURE:
<223> OTHER INFORMATION: human cytomegalovirus glycoprotein B peptide
```

<400> SEQUENCE: 128

Phe Phe Ile Phe Pro Asn Trp Thr Ile Val Ser Arg Phe Gly Arg Pro
1               5                   10                  15

Asn Ala Ala

<210> SEQ ID NO 129
<211> LENGTH: 12
<212> TYPE: PRT
<213> ORGANISM: Artificial Sequence
<220> FEATURE:
<223> OTHER INFORMATION: human cytomegalovirus glycoprotein B peptide

<400> SEQUENCE: 129

Phe Phe Ile Phe Pro Asn Tyr Thr Ile Val Ser Arg
1               5                   10

<210> SEQ ID NO 130
<211> LENGTH: 10
<212> TYPE: PRT
<213> ORGANISM: Artificial Sequence
<220> FEATURE:
<223> OTHER INFORMATION: human cytomegalovirus glycoprotein B peptide

<400> SEQUENCE: 130

Phe Phe Ile Phe Pro Asn Tyr Thr Ile Val
1               5                   10

<210> SEQ ID NO 131
<211> LENGTH: 9
<212> TYPE: PRT
<213> ORGANISM: Artificial Sequence
<220> FEATURE:
<223> OTHER INFORMATION: human cytomegalovirus glycoprotein B peptide

<400> SEQUENCE: 131

Phe Phe Ile Phe Pro Asn Tyr Thr Ile
1               5

<210> SEQ ID NO 132
<211> LENGTH: 35
<212> TYPE: PRT
<213> ORGANISM: Artificial Sequence
<220> FEATURE:
<223> OTHER INFORMATION: human cytomegalovirus glycoprotein B peptide

<400> SEQUENCE: 132

Asp Lys Phe Phe Ile Phe Pro Asn Tyr Thr Ile Val Ser Asp Phe Gly
1               5                   10                  15

Arg Pro Asn Ala Ala Pro Glu Thr His Arg Leu Val Ala Phe Leu Glu
            20                  25                  30

Arg Ala Asp
        35

<210> SEQ ID NO 133
<211> LENGTH: 32
<212> TYPE: PRT
<213> ORGANISM: Artificial Sequence
<220> FEATURE:
<223> OTHER INFORMATION: human cytomegalovirus glycoprotein B peptide

<400> SEQUENCE: 133

Phe Ile Phe Pro Asn Tyr Thr Ile Val Ser Asp Phe Gly Arg Pro Asn
1               5                   10                  15

Ala Ala Pro Glu Thr His Arg Leu Val Ala Phe Leu Glu Arg Ala Asp 20                  25                  30

<210> SEQ ID NO 134
<211> LENGTH: 29
<212> TYPE: PRT
<213> ORGANISM: Artificial Sequence
<220> FEATURE:
<223> OTHER INFORMATION: human cytomegalovirus glycoprotein B peptide

<400> SEQUENCE: 134

Pro Asn Tyr Thr Ile Val Ser Asp Phe Gly Arg Pro Asn Ala Ala Pro
 1               5                  10                  15

Glu Thr His Arg Leu Val Ala Phe Leu Glu Arg Ala Asp
            20                  25

<210> SEQ ID NO 135
<211> LENGTH: 26
<212> TYPE: PRT
<213> ORGANISM: Artificial Sequence
<220> FEATURE:
<223> OTHER INFORMATION: human cytomegalovirus glycoprotein B peptide

<400> SEQUENCE: 135

Thr Ile Val Ser Asp Phe Gly Arg Pro Asn Ala Ala Pro Glu Thr His
 1               5                  10                  15

Arg Leu Val Ala Phe Leu Glu Arg Ala Asp
            20                  25

<210> SEQ ID NO 136
<211> LENGTH: 23
<212> TYPE: PRT
<213> ORGANISM: Artificial Sequence
<220> FEATURE:
<223> OTHER INFORMATION: human cytomegalovirus glycoprotein B peptide

<400> SEQUENCE: 136

Ser Asp Phe Gly Arg Pro Asn Ala Ala Pro Glu Thr His Arg Leu Val
 1               5                  10                  15

Ala Phe Leu Glu Arg Ala Asp
            20

<210> SEQ ID NO 137
<211> LENGTH: 19
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 19
<223> OTHER INFORMATION: Ala 19 fused to human serum albumin

<400> SEQUENCE: 137

Phe Phe Ile Phe Pro Asn Tyr Thr Ile Val Ser Asp Phe Gly Arg Pro
 1               5                  10                  15

Asn Ala Ala

<210> SEQ ID NO 138
<211> LENGTH: 30
<212> TYPE: PRT
<213> ORGANISM: Artificial Sequence
<220> FEATURE:
<223> OTHER INFORMATION: human cytomegalovirus glycoprotein B peptide

<400> SEQUENCE: 138

Phe Phe Ile Phe Pro Asn Tyr Thr Ile Val Ser Asp Phe Gly Arg Pro

```
                1               5                  10                  15
Asn Ala Ala Gly Arg Lys Lys Arg Arg Gln Arg Arg Arg Pro
            20                  25                  30

<210> SEQ ID NO 139
<211> LENGTH: 28
<212> TYPE: PRT
<213> ORGANISM: Artificial Sequence
<220> FEATURE:
<223> OTHER INFORMATION: human cytomegalovirus glycoprotein B peptide

<400> SEQUENCE: 139

Phe Phe Ile Phe Pro Asn Tyr Thr Ile Val Ser Asp Phe Gly Arg Pro
 1               5                  10                  15

Asn Ala Ala Arg Arg Arg Arg Arg Arg Arg Arg
            20                  25

<210> SEQ ID NO 140
<211> LENGTH: 28
<212> TYPE: PRT
<213> ORGANISM: Artificial Sequence
<220> FEATURE:
<223> OTHER INFORMATION: human cytomegalovirus glycoprotein B peptide

<400> SEQUENCE: 140

Phe Phe Ile Phe Pro Asn Tyr Thr Ile Val Ser Asp Phe Gly Arg Pro
 1               5                  10                  15

Asn Ala Ala Ala Ser Lys Ser Lys Ser Lys Ser Lys
            20                  25

<210> SEQ ID NO 141
<211> LENGTH: 20
<212> TYPE: PRT
<213> ORGANISM: Artificial Sequence
<220> FEATURE:
<223> OTHER INFORMATION: human cytomegalovirus glycoprotein B peptide
<221> NAME/KEY: MOD_RES
<222> LOCATION: 20
<223> OTHER INFORMATION: D-Pro

<400> SEQUENCE: 141

Phe Phe Ile Phe Pro Asn Tyr Thr Ile Val Ser Asp Phe Gly Arg Pro
 1               5                  10                  15

Asn Ala Ala Pro
            20

<210> SEQ ID NO 142
<211> LENGTH: 27
<212> TYPE: PRT
<213> ORGANISM: Artificial Sequence
<220> FEATURE:
<223> OTHER INFORMATION: human cytomegalovirus glycoprotein B peptide

<400> SEQUENCE: 142

Trp Glu Ile His His Ile Asn Lys Phe Ala Gln Cys Tyr Ser Ser Tyr
 1               5                  10                  15

Ser Arg Val Ile Gly Gly Thr Val Phe Val Ala
            20                  25

<210> SEQ ID NO 143
<211> LENGTH: 34
<212> TYPE: PRT
<213> ORGANISM: Artificial Sequence
<220> FEATURE:
<223> OTHER INFORMATION: Modified HCMV gB peptide
```

<400> SEQUENCE: 143

Lys Asp Gln Trp His Ser Arg Gly Ser Thr Trp Leu Tyr Arg Glu Thr
1               5                   10                  15

Ala Asn Leu Asn Ala Met Leu Thr Ile Thr Ala Arg Ser Lys Tyr
            20                  25                  30

Pro Tyr

<210> SEQ ID NO 144
<211> LENGTH: 37
<212> TYPE: PRT
<213> ORGANISM: Artificial Sequence
<220> FEATURE:
<223> OTHER INFORMATION: Modified HCMV gB peptide

<400> SEQUENCE: 144

Val Thr Val Lys Asp Gln Trp His Ser Arg Gly Ser Thr Trp Leu Tyr
1               5                   10                  15

Arg Glu Thr Ala Asn Leu Asn Ala Met Leu Thr Ile Thr Ala Arg
            20                  25                  30

Ser Lys Tyr Pro Tyr
        35

<210> SEQ ID NO 145
<211> LENGTH: 34
<212> TYPE: PRT
<213> ORGANISM: Artificial Sequence
<220> FEATURE:
<223> OTHER INFORMATION: Modified HCMV gB peptide

<400> SEQUENCE: 145

Trp His Ser Arg Gly Ser Thr Trp Leu Tyr Arg Glu Thr Ala Asn Leu
1               5                   10                  15

Asn Ala Met Leu Thr Ile Thr Ala Arg Ser Lys Tyr Pro Tyr His
            20                  25                  30

Phe Phe

<210> SEQ ID NO 146
<211> LENGTH: 39
<212> TYPE: PRT
<213> ORGANISM: Artificial Sequence
<220> FEATURE:
<223> OTHER INFORMATION: Modified HCMV gB peptide

<400> SEQUENCE: 146

Lys Asp Gln Trp His Ser Arg Gly Ser Thr Trp Leu Tyr Arg Glu Thr
1               5                   10                  15

Ala Asn Leu Asn Ala Met Leu Thr Ile Thr Ala Arg Ser Lys Tyr
            20                  25                  30

Pro Tyr His Phe Phe Ala Thr
        35

<210> SEQ ID NO 147
<211> LENGTH: 32
<212> TYPE: PRT
<213> ORGANISM: Artificial Sequence
<220> FEATURE:
<223> OTHER INFORMATION: Modified HCMV gB peptide

<400> SEQUENCE: 147

Trp His Ser Arg Gly Ser Thr Trp Leu Tyr Arg Ala Glu Thr Ala Asn
1               5                   10                  15

```
Leu Asn Ala Met Leu Thr Ile Thr Thr Ala Arg Ser Lys Tyr Pro Tyr
            20                  25                  30

<210> SEQ ID NO 148
<211> LENGTH: 32
<212> TYPE: PRT
<213> ORGANISM: Artificial Sequence
<220> FEATURE:
<223> OTHER INFORMATION: Modified HCMV gB peptide

<400> SEQUENCE: 148

Trp His Ser Arg Gly Ser Thr Trp Leu Tyr Arg Glu Thr Ala Asn Leu
 1               5                  10                  15

Asn Ala Met Leu Thr Ile Thr Thr Ala Arg Ser Lys Tyr Pro Tyr Pro
            20                  25                  30

<210> SEQ ID NO 149
<211> LENGTH: 32
<212> TYPE: PRT
<213> ORGANISM: Artificial Sequence
<220> FEATURE:
<223> OTHER INFORMATION: Modified HCMV gB peptide

<400> SEQUENCE: 149

Trp His Ser Arg Gly Ser Thr Trp Leu Tyr Arg Glu Thr Ala Asn Leu
 1               5                  10                  15

Asn Ala Met Leu Thr Ile Thr Thr Ala Arg Ser Lys Tyr Pro Tyr Gly
            20                  25                  30
```

PEPTIDE COMPOSITIONS AND METHODS FOR INHIBITING HERPESVIRUS INFECTION

CROSS-REFERENCE TO RELATED APPLICATIONS

This application claims the benefit of U.S. Provisional Application Ser. No. 61/280,112, filed on Oct. 30, 2009, which is incorporated herein by reference in its entirety.

STATEMENT OF GOVERNMENT SUPPORT

This invention was made with government support under a U.S. Housing and Urban Development (HUD) Community Development Block Grant (CDBG) (PL 109-148) administered by the Office of Community Development on behalf of the State of Louisiana under Contract No. RCEEP-06 (2007-10). The United States government has certain rights in this invention.

FIELD OF THE INVENTION

This invention relates to peptide compositions and methods for treating, preventing, or inhibiting human herpesvirus (HHV) infection, such as a Human Cytomegalovirus (HCMV; HHV-5), Herpes Simplex Virus 1 (HSV-1; HHV-1), Herpes Simplex Virus 2 (HSV-2; HHV-2), Varicella Zoster Virus (VZV; HHV-3), Epstein-Barr Virus (EBV; HHV-4), Human Herpes Virus 6 (HHV-6), Human Herpes Virus 7 (HHV-7), or Kaposi's Sarcoma-Associated Herpesvirus (KSHV; HHV-8) infection.

BACKGROUND OF THE INVENTION

Human herpesviruses are a diverse family of enveloped viruses that infect their hosts for life by establishing latency until virus reactivation due to immunosuppression, stress, or other cues. Herpesviruses cause a number of diseases ranging from those that are non-threatening to quite serious conditions. Non-limiting examples of herpesviruses include, HCMV, HSV-1, HSV-2, EBV, VZV, HHV-6, HHV-7, and KSHV. HCMV is a ubiquitous opportunistic pathogen that belongs to Betaherpesviridae. The virulence of this pathogen is directly linked to the immune status of its host. Primary HCMV infection is generally asymptomatic in immunocompetent individuals. After primary HCMV infection, the virus establishes lifelong latency within the host and periodically reactivates with little pathological consequences. In contrast, HCMV infection in immunocompromised patients, such as AIDS patients, and solid organ and allogeneic stem cell transplantation recipients causes serious disease (1). HCMV is also the leading cause of congenital viral infection most often resulting from a primary infection of the mother during or right before pregnancy that leads to spontaneous abortion, premature delivery, intrauterine growth restriction (IUGR), or pre-eclampsia. The risk of primary infection in a seronegative mother is 1 to 4%, which carries a 30 to 40% risk of congenital infection (2, 3). The majority of congenitally infected babies are asymptomatic at birth; however, 10 to 17% will subsequently develop hearing defects or neurodevelopmental sequelae (4).

HCMV has a double-stranded DNA genome of about 235 kb encoding about 165 genes (5). It has a very broad cellular tropism resulting in the potential infection of nearly every organ system. The ability of HCMV to enter a wide range of cell types necessitates a very complex interaction between viral envelope glycoproteins and several host cell surface receptors. The entry of herpesviruses into host cells is complex and still poorly understood. The HCMV virion envelope contains at least 20 virus-encoded glycoproteins that are involved in cell attachment and penetration (6). Of these, glycoprotein B (gB) is the most abundant glycoprotein of the HCMV envelope (7) and is highly conserved among the herpesvirus family (8). Glycoprotein B plays a critical role in the HCMV entry process where, initially, gB along with gM/gN (a complex of glycoproteins M and N), is involved in tethering of virions to heparin sulfate proteoglycans (HSPGs) on the surface of host cells. The short interactions of HCMV virions with HSPGs are followed by more stable interactions with one or more viral cellular receptors, namely EGFR (9), PDGFR (10), and TLR-2 (11). gB also interacts with integrin $\alpha_v\beta_3$, a coreceptor that enhances HCMV entry (12). Integrins are known to synergize with EGFR as well as with other receptors to activate signal transduction pathways (13-15). To complete the entry process, both viral and cellular membranes fuse, which allows the release of virion-encoded tegument and capsid proteins into the cytoplasm. This final step of viral entry into host cells requires gB and the glycoprotein H/glycoprotein L complex (16-19).

HCMV infection is highly prevalent in the population due to the ability of the virus to efficiently transmit between hosts that harbor and periodically shed the virus. HCMV is transmitted through the direct exposure to infected body secretions, including saliva, urine and milk. Following infection, HCMV enters the bloodstream and spreads to various organs including kidney, liver, spleen, heart, brain, retina, esophagus, inner ear, lungs, colon, and salivary glands (20). The ability of HCMV to infect this wide variety of cell types is not due to the presence of a high level of extracellular virus in the plasma, but it is mainly the result of cell-cell transmission between a mononuclear phagocytes, possibly a macrophage or dendritic cell precursor, and uninfected tissues (21).

Antibodies to HCMV gB have been shown to not only block penetration of virions into cells, but also to limit cell to cell infection, implying that gB plays a role in virion penetration into cells, virus transmission from cell to cell, as well as fusion of infected cells (18, 22). Recently, Isaacson and coworkers used genetic complementation to confirm that gB is required for the fusion of viral and cellular membranes, virus entry, and cell-to-cell spread of HCMV (23).

Since HCMV and other herpesviruses establish a lifelong latency in humans, antiviral therapy that inhibits viral entry may serve as an alternative to the already existing therapeutic agents. Here, we report the design and development characterization of peptides that specifically inhibit the fusion of HCMV to the host cell membrane to inhibit viral infection and/or replication as a novel approach to prevent HCMV infection.

SUMMARY OF THE INVENTION

This application contains biological sequence information. The Sequence Listing for this application is provided in an ASCII compliant text file (named "TU389-US-SEQ.txt"), which was created on Aug. 20, 2012, and which has a file size of 77,542 bytes. This ASCII compliant text file is hereby incorporated herein by reference.

The present invention provides peptides that include a sequence having a high degree of sequence similarity to a portion of human cytomegalovirus (HCMV) glycoprotein B (gB) that is involved in fusion of the virion to cell membranes.

HCMV gB has the amino acid sequence of SEQ ID NO: 1 (FIG. 1A). These peptides inhibit virion:cell membrane fusion. Because virion:cell membrane fusion is required for infection of a non-infected cell, the peptides of the present invention are useful for inhibiting infection at the cellular level, regardless of whether the virus comes from an exogenous source or from an outbreak of a preexisting dormant infection. Consequently, the peptides of this invention are useful for treating existing herpesvirus infections and outbreaks by preventing spread of the virus to non-infected cells, as well as preventing new herpesvirus infections and preventing outbreaks of dormant infections, if the peptide is administered prophylactically. In one embodiment, the invention provides an isolated peptide having an amino acid residue sequence that comprises at least one Wimley White Interfacial Hydrophobicity Scale (WWIHS)-positive human cytomegalovirus glycoprotein B (HCMV-gB) sequence segment. Each WWIHS-positive HCMV-gB sequence segment of the peptide consists of at least 8 and not more than 60 consecutive amino acid residues from residues 146 to 315 of SEQ ID NO: 1 (which comprises the fusion domain region of gB), or from a variant sequence that has at least 70% sequence identity to residues 146 to 315 of SEQ ID NO: 1. In addition to the WWIHS-positive segment(s), the peptide can include additional amino acid residues at the N-terminal and/or C-terminal end of each WWIHS-positive segment, if desired.

In a preferred embodiment, the amino acid residue sequence of the peptide includes a HCMV-gB sequence segment that consists of (a) consecutive residues from residues 146 to 315 of SEQ ID NO: 1, or from a sequence variant of residues 146 to 315 of SEQ ID NO: 1 that has at least 70% sequence identity thereto; (b) consecutive residues from residues 174 to 200 of SEQ ID NO: 1, or from a sequence variant of residues 174 to 200 of SEQ ID NO: 1 that has at least 70% sequence identity thereto; (c) consecutive residues from residues 233 to 263 of SEQ ID NO: 1, or from a sequence variant of residues 233 to 263 of SEQ ID NO: 1 that has at least 70% sequence identity thereto; (d) consecutive residues from residues 264 to 291 of SEQ ID NO: 1, or from a sequence variant of residues 264 to 291 of SEQ ID NO: 1 that has at least 70% sequence identity thereto; (e) consecutive residues from residues 297 to 315 of SEQ ID NO: 1, or from a sequence variant of residues 297 to 315 of SEQ ID NO: 1 that has at least 70% sequence identity thereto; and (f) consecutive residues from residues 476 to 494 of SEQ ID NO: 1, or from a sequence variant of residues 476 to 494 of SEQ ID NO: 1 that has at least 70% sequence identity thereto. Preferably, the HCMV-gB sequence segment consists of at least 15 consecutive residues of the enumerated residues of SEQ ID NO: 1 or variant thereof. The amino acid residue sequences of the peptide variants preferably comprise only conservative substitution in the enumerated residues of SEQ ID NO: 1.

In some preferred embodiments, the peptide includes a HCMV-gB sequence segment having an amino acid residue sequence selected from the group consisting of SEQ ID NO: 3, SEQ ID NO: 4, SEQ ID NO: 5, SEQ ID NO: 6, SEQ Id NO: 7, and a sequence variant having at least 70% sequence identity (preferably at least 90% sequence identity) to SEQ ID NO: 3, SEQ ID NO: 4, SEQ ID NO: 5, SEQ ID NO: 6, or SEQ ID NO: 7, and which preferably differs therefrom by only conservative substitutions.

In other aspects, the present invention provides methods for treating, preventing or otherwise inhibiting herpesvirus infections by administering a therapeutically effective amount of a peptide of the invention to a subject that has been exposed to a herpesvirus. The methods of the present invention can be used to treat any herpesvirus infection, including, without limitation, an HCMV, HSV-1, HSV-2, EBV, VZV, HHV-6, HHV-7, or KSHV infection, and the like. It is to be understood that some peptides will be more effective for a particular herpesvirus infection than other peptides. The peptides of the present invention that include portions of residues 146 to 315 of SEQ ID NO: 1 or a sequence variant of residues 146 to 315 of SEQ ID NO: 1 that has at least 70% sequence identity thereto are particularly useful for treating, preventing, or inhibiting HCMV infections, especially in immuno-compromised subjects. Similarly, peptides of the invention that include portions of residues 476 to 494 of SEQ ID NO: 1 or a sequence variant of residues 476 to 494 of SEQ ID NO: 1 that has at least 70% sequence identity thereto are particularly useful for treating an HSV-1 infections. The peptides can be administered alone or in combination with one or more other therapeutic agent, such as another antiviral agent. The peptides preferably are administered in a pharmaceutically acceptable carrier, vehicle or diluent (e.g., a buffer at physiological pH).

The present invention also provides pharmaceutical compositions comprising a peptide of the present invention in combination with a pharmaceutically acceptable carrier, vehicle or diluent. The pharmaceutical composition can also include excipients, preservatives, and other pharmaceutically useful materials, e.g., to provide storage stability, or to impart desirable physical properties to the composition. The pharmaceutical compositions of the present invention can be formulated with other therapeutic agents, such as antiviral agents, if desired.

This invention also provides uses of the peptides for treating, preventing, or inhibiting herpesvirus infections (particularly HCMV infections), as well as uses of the peptides for preparing pharmaceutical compositions for inhibiting herpesvirus infections.

The peptides, pharmaceutical compositions, and methods of the present invention can beneficially be used to treat any patient suffering from or at risk of developing a herpesvirus infection or outbreak thereof. The peptides, pharmaceutical compositions, and methods of this invention are particularly useful for immuno-compromised patients (retinitis patients, transplant patients, allogeneic stem cell transplantation recipients), as well as to reduce viral load in pregnant women, thereby reducing spread of a herpesvirus (e.g., HCMV and the like) to the placenta and subsequently to the fetus. Additionally, these peptides, pharmaceutical compositions, and methods also can be used for treating CMV-infected neonates to reduce the risk of development of sensorineural hearing loss.

The dosage level for administering the peptide to a subject in the methods of the present invention will be an amount sufficient to provide a therapeutically useful outcome (e.g., suppression of a herpesvirus outbreak, prevention of an active infection after known exposure to a herpesvirus, and the like). The determination of a therapeutically effective amount of a peptide of the invention is also within the level of ordinary skill of medical and pharmaceutical professionals.

BRIEF DESCRIPTION OF THE DRAWING FIGURES

FIG. 1, Panel A, provides the amino acid residue sequence of HCMV gB; Panel B illustrates a WWIHS plot of HCMV gB; the underlined portions represent peptide regions within gB that display a high propensity to interact with the lipid surface of cell membranes (i.e., having positive hydrophobicity scores).

FIGS. 2A, 2B, 2C, and 2D illustrate the ability of HCMV gB peptides to inhibit viral infection. In each Figure, Panel I shows graphs of the number of Green Fluorescent Protein (GFP) positive cells observed after exposure of human foreskin fibroblast (HFF) cells to HCMV (Towne GFP strain) preincubated in the presence of the indicated peptide (i.e., 2A—Peptide 174-200 of HCMV gB (SEQ ID NO: 3); 2B—Peptide 233-263 of HCMV gB (SEQ ID NO: 4); 2C—Peptide 264-291 of HCMV gB (SEQ ID NO: 5); and 2D—Peptide 297-315 of HCMV gB (SEQ ID NO: 6)); while Panels II and III show a ribbon structure for HCMV gB trimer with the approximate location of the peptide segment indicated by arrows. Each Panel II shows a view from the end of the trimer that contacts the cell membrane; while each Panel III shows a side view of the trimer with the end that contacts the cell membrane on the right.

Figure 3A:
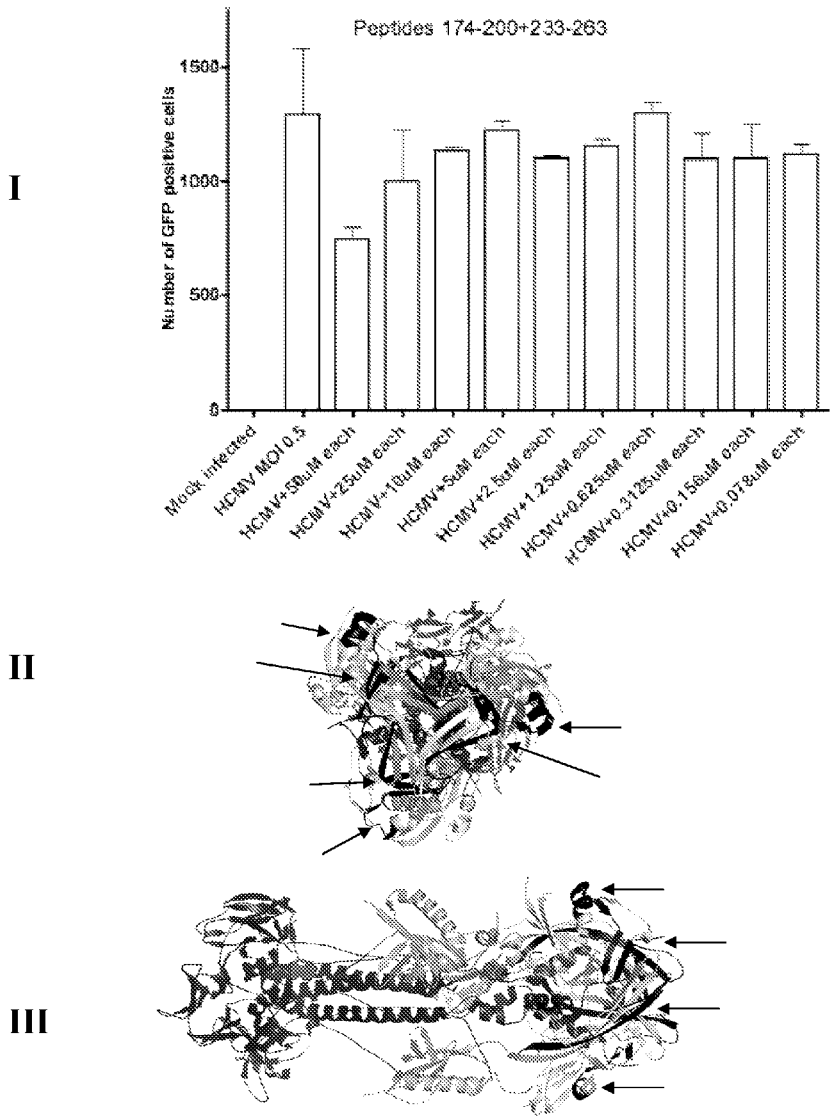
Figure 3B:
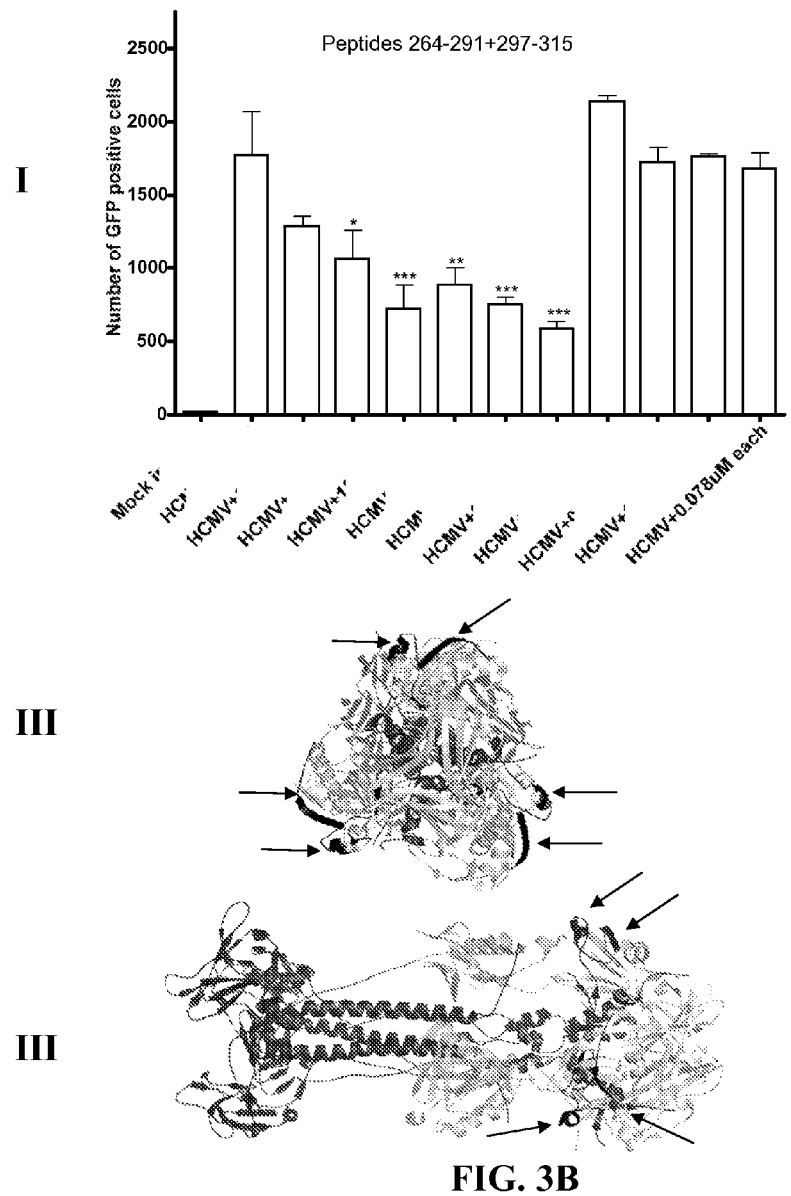

FIGS. 3A and 3B illustrate the additive effect of HCMV gB peptides on viral infection. In each Figure, Panel I shows graphs of the number of Green Fluorescent Protein (GFP) positive cells observed after exposure of human foreskin fibroblast (HFF) cells to HCMV (Towne GFP strain) preincubated in the presence of the indicated combination of peptides (i.e., 3A—Peptide 174-200 (SEQ ID NO: 3) combined with Peptide 233-263 (SEQ ID NO: 4); 3B—Peptide 264-291 (SEQ ID NO: 5) combined with Peptide 297-315 (SEQ ID NO: 6)); while Panels II and III show ribbon structures for HCMV gB trimer with the approximate location of the peptide segments indicated by arrows. Each Panel II shows a view from the end of the trimer that contacts the cell membrane; while each Panel III shows a side view of the trimer with the end that contacts the cell membrane on the right.

Figure 4:
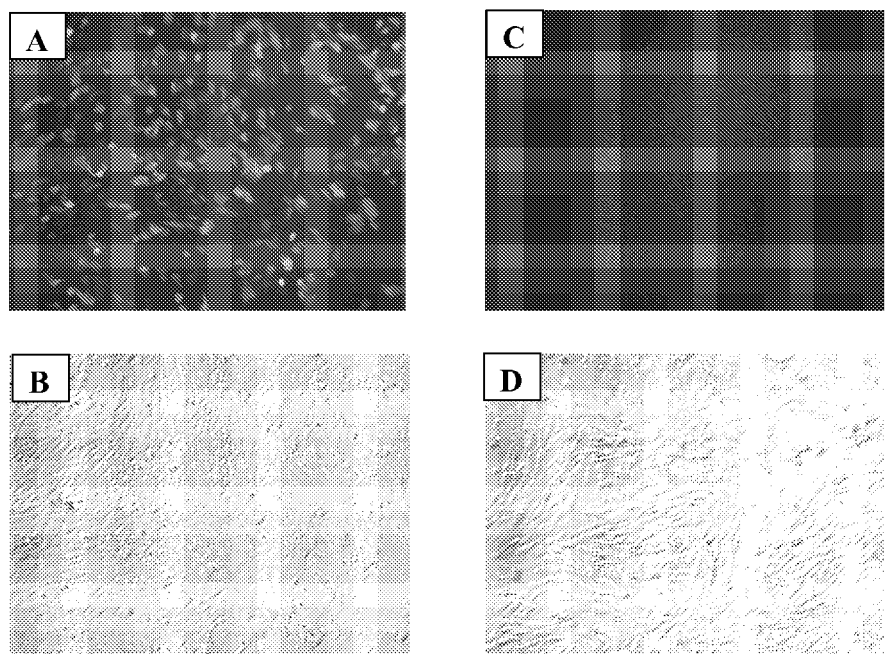

FIG. 4 illustrates the ability of HCMV gB Peptide 233-263 (SEQ ID NO: 4) to inhibit viral infection. Panels A-B show representative fluorescent and bright light microscopic images, respectively, of HFF cells infected with Towne GFP strain of HCMV at the MOI of 0.5; Panels C-D show representative fluorescent and bright light images of HFF cells infected with Towne strain of HCMV at the MOI of 0.5 preincubated with Peptide 233-263 (SEQ ID NO: 4) at the concentration of 100 µM.

Figure 5:
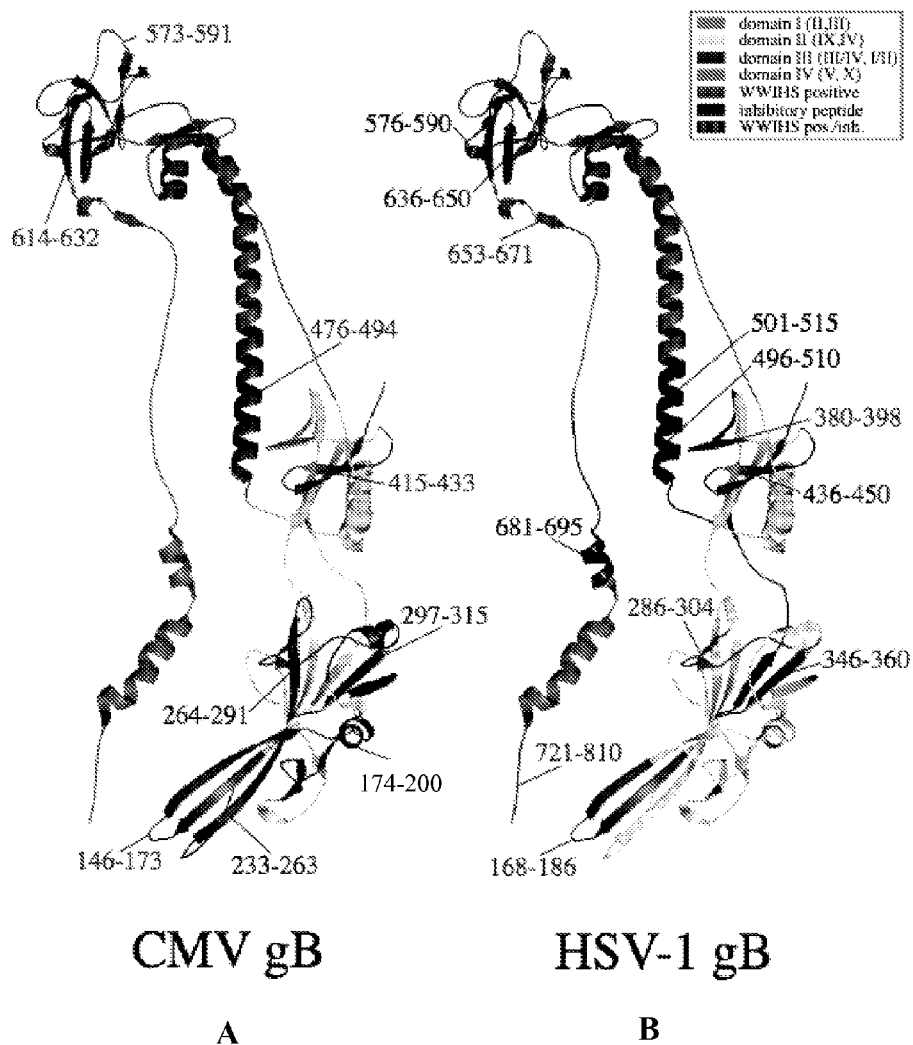

FIG. 5 provides a comparison of HSV-1 gB inhibitory peptides (Akkarawongsa et al.) and HCMV gB inhibitory peptides, shown in position on the ribbon structures of the two proteins.

Figure 6:
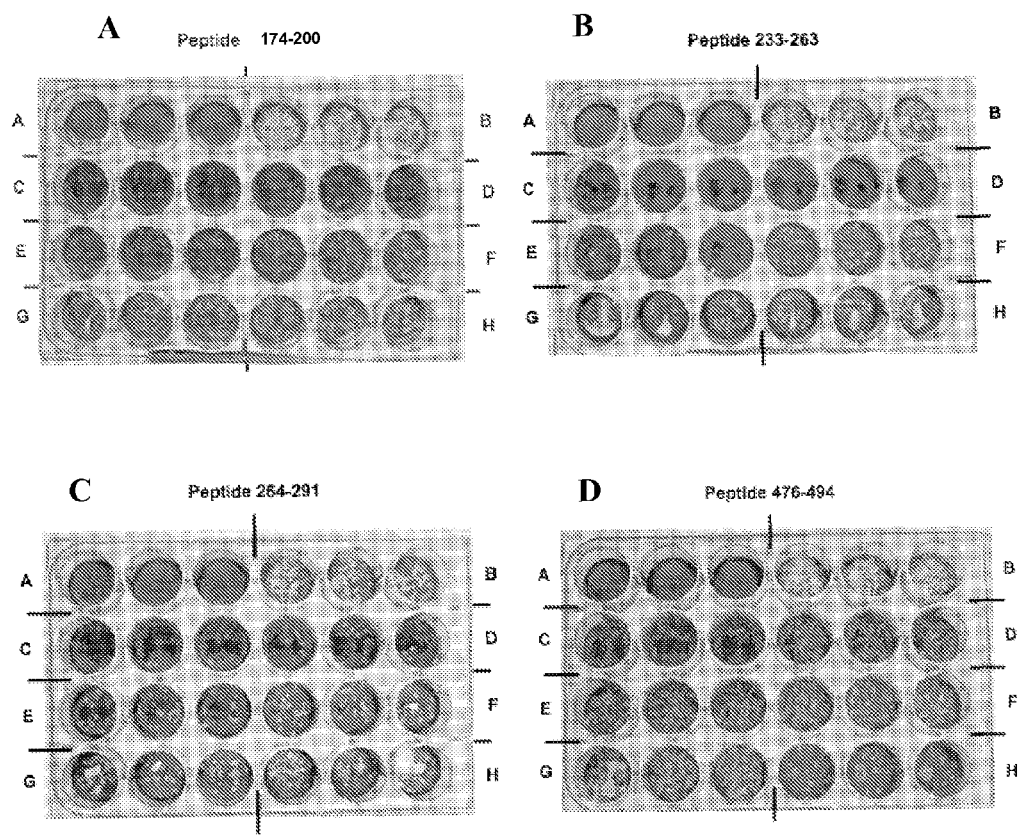

FIG. 6 illustrates inhibition of HSV-1 infection by HCMV gB peptides. To evaluate the ability of newly designed HCMV gB-specific peptide to inhibit HSV-1 infection, Vero cells were infected for about 90 minutes at room temperature with HSV-1 (McIntyre strain; MOI=0.001) that was preincubated with a range of concentrations of four different synthetic peptides at about 37° C. for about 90 minutes. Images of the plates for each treatment are shown in the figure. Each treatment was done in triplicate, where A=media, B=HSV-1 MOI of 0.001, C=100 µM peptide and virus, D=50 µM peptide and virus, E=25 µM peptide and virus, F=10 µM peptide and virus, G=5 µM peptide and virus, H=2.5 µM peptide and virus. HCMV gB peptides (Peptide 174-200 (SEQ ID NO: 3), Peptide 233-263 (SEQ ID NO: 4), and Peptide 264-291 (SEQ ID NO: 5)) that are within domain II were inhibitory against HSV-1 infection. Peptide 476-494 (SEQ ID NO: 7) corresponds to trimerization domain of HCMV gB that contains extended α-helices important in the formation of HCMV gB homotrimer during fusion of HCMV virion and lipid membrane of the host cell. Overlapping inhibitory HSV-1 peptides span regions 496-510 and 501-515 of HSV-1 gB (SEQ ID NO: 8) and are analogous to HCMV gB Peptide 476-494 (SEQ ID NO: 7).

FIG. 7 provides the amino acid residue sequence of human herpesvirus 1 gB.

FIG. 8 provides examples of peptides of the present invention.

FIG. 9 provides examples of peptides of the present invention.

FIG. 10 provides examples of peptides of the present invention.

FIG. 11 provides examples of peptides of the present invention.

FIG. 12 provides examples of peptides of the present invention.

Figure 13:
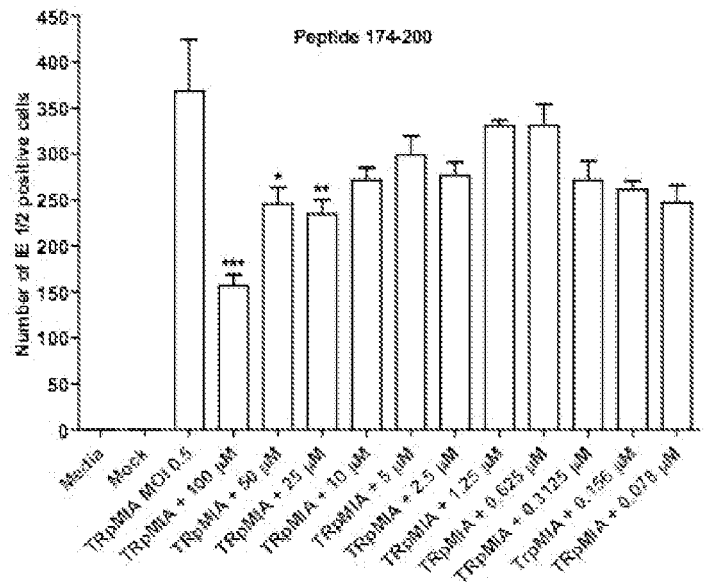

FIG. 13 provides inhibition data for Peptide 174-200 against HCMV TRpMIA.

Figure 14:
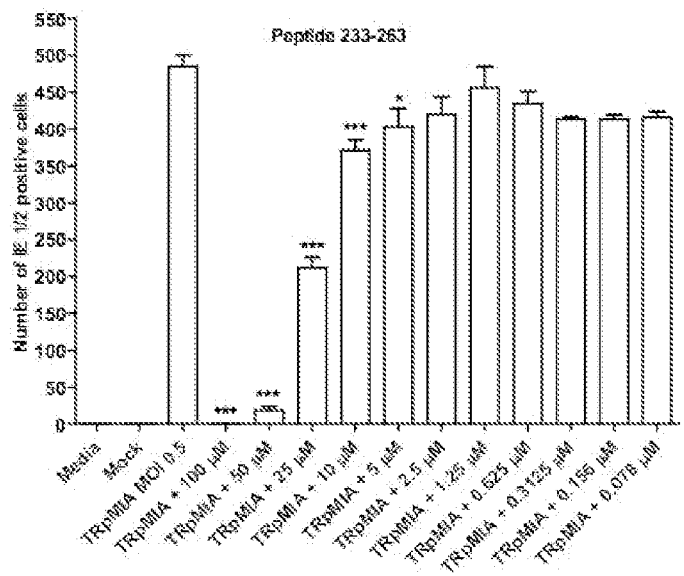

FIG. 14 provides inhibition data for Peptide 233-263 against HCMV TRpMIA.

Figure 15:
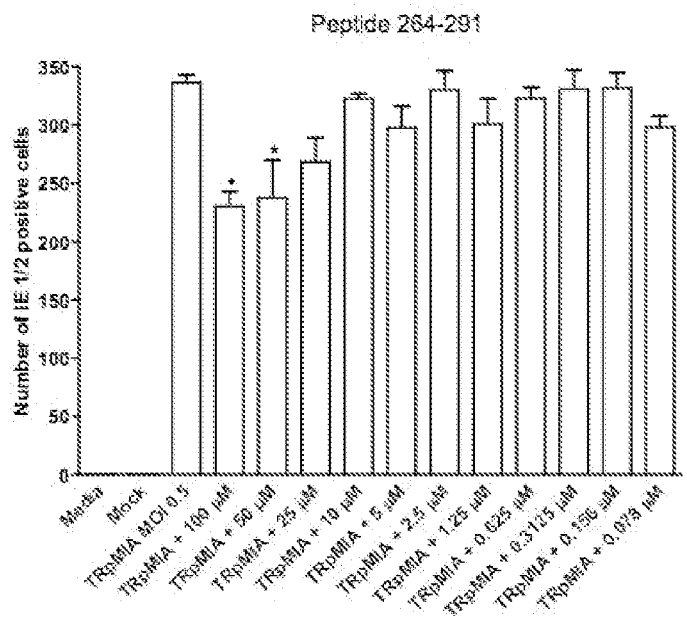

FIG. 15 provides inhibition data for Peptide 264-291 against HCMV TRpMIA.

Figure 16:
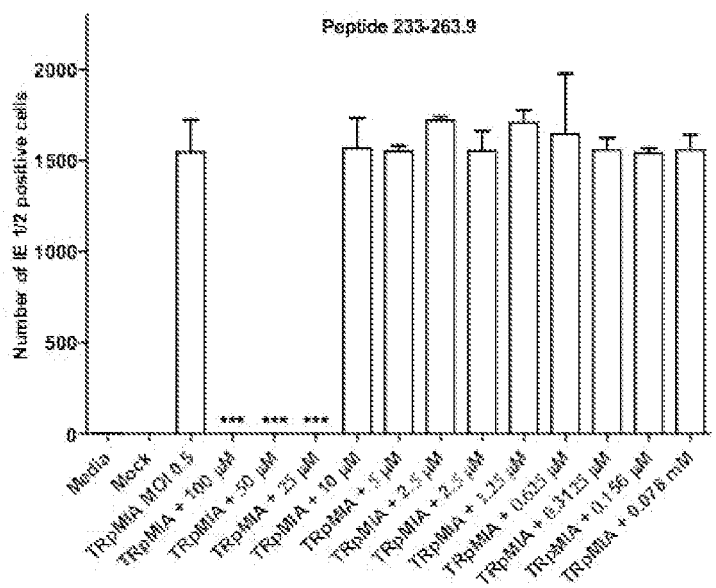

FIG. 16 provides inhibition data for Peptide 233-263.9 against HCMV TRpMIA.

DETAILED DESCRIPTION OF PREFERRED EMBODIMENTS

The present invention provides peptides that comprise an amino acid residue sequence having a high degree of sequence similarity to a portion of human cytomegalovirus (HCMV) glycoprotein B (gB) that is involved in fusion of the virion to cell membranes. HCMV gB has the amino acid sequence of SEQ ID NO: 1 (National Center for Biotechnology Information Database EMBL Accession No. DAA00160). In one preferred embodiment, the isolated peptides have an amino acid residue sequence that comprises at least one Wimley White Interfacial Hydrophobicity Scale (WWIHS)-positive human cytomegalovirus glycoprotein B (HCMV-gB) sequence segment. Each WWIHS-positive HCMV-gB sequence segment consists of at least 8 (e.g., at least 8, 10, or 15) and not more than 60 (e.g., not more than 60, 50, 45, 40, or 35) consecutive amino acid residues from residues 146 to 315 of SEQ ID NO: 1, or from a sequence variant of residues 146 to 315 of SEQ ID NO: 1 that has at least 70% (e.g., at least 75%, 80%, 85% 90%, 95%, or 98%) sequence identity thereto. In some embodiments, the variant differs from the corresponding portion of SEQ ID NO: 1 only by one or more conservative substitutions. Preferably, the WWIHS-positive HCMV-gB sequence segment consists of at least 15 consecutive residues of the enumerated residues of SEQ ID NO: 1 or variant thereof.

In another preferred embodiment, the present invention provides a peptide that includes at least one HCMV-gB sequence segment, and each HCMV-gB sequence segment in the peptide consists of at least 8 (preferably at least 15) and preferably not more than 60 consecutive residues from residues 174 to 200 of SEQ ID NO: 1, residues 233 to 263 of SEQ ID NO: 1, residues 264 to 291 of SEQ ID NO: 1, residues 297 to 315 of SEQ ID NO: 1, residues 476 to 494 of SEQ ID NO: 1, or a variant sequence thereof having at least about 70, 75, 80, 85, 90, 95, or 98% sequence identity, preferably at least 90% sequence identity to the specified portion of SEQ ID NO: 1.

In another embodiment, the peptide includes at least a consecutive portion of residues 146-200 of SEQ ID NO: 1 (e.g., 8 to 54 consecutive residues), a sequence variant thereof having at least 70% sequence identity thereto.

As used herein, the term "WWIHS-positive" refers to an amino acid residue sequence that has a calculated WWIHS score with a positive free energy (ΔG) value (preferably a ΔG value of greater than 1, 2, 3, or 4 kcal/mol), e.g., as determined by any of the methods and computer programs described or referred to herein, such as the MPEx program. Preferably, the WWIHS-positive HCMV-gB sequence segment comprises at least 10 or at least 15 consecutive amino acid residues from the enumerated residues of SEQ ID NO: 1 or variant thereof, and preferably not more than 45, 40, 35, 30, or 20 consecutive amino acid residues thereof.

The peptides of this invention can include an amino acid residue sequence that is identical to one of the specified HCMV-gB sequence segment of SEQ ID NO: 1 described herein, or that is a variant that differs from the HCMV-gB sequence segment by one or more substitutions, preferably conservative substitutions. Preferably, the only substitutions in the HCMV-gB sequence segment are conservative substitutions. Substitutions of one or more L-amino acid with one or more D-amino acid, and/or substitution of one or more cysteine residues with one or more alanine residues are also suitable substitutions and are to be considered as conservative substitutions in the context of the present invention and the appended claims.

The peptides of the present invention can include other amino acid sequences flanking the portion or portions comprising the HCMV-gB sequence segment (e.g., at the amino and/or carboxyl terminus thereof). Such additional sequences, as well as substitutions in the segment of SEQ ID NO: 1, can be used to modify or optimize the physical, physiological, or chemical characteristics of the peptide for use in a pharmaceutical composition for inhibiting herpesvirus infections. For example, the additional sequences or substitutions can stabilize the peptide under physiological conditions, or can be used to enhance compatibility of the peptide with a preferred delivery vehicle or carrier.

The peptides of the present invention are useful for inhibiting virion:cell membrane fusion, and thus inhibiting or preventing infection by a herpesvirus, as is described in more detail herein.

As used herein, the term "conservative substitution" and grammatical variations thereof, refers to the presence of an amino acid residue in the sequence of the peptide that is different from, but is in the same class of amino acid as the wild-type residue of HCMV gB. In this regard, conservative substitutions include a nonpolar (hydrophobic) amino acid residue replacing a nonpolar amino acid residue, an aromatic amino acid residue replacing an aromatic amino acid residue, or a polar (hydrophilic) amino acid residue replacing a polar amino acid residue (e.g., a polar uncharged residue replacing a polar uncharged residue, a charged residue replacing a charged residue, a polar uncharged residue (e.g., Asn or Gln) replacing a charged residue (e.g., Asp or Glu), or a charged residue replacing a polar uncharged residue). In addition, conservative substitutions encompass peptides in which a native amino acid residue is replaced by a residue having an interfacial hydropathy value of the same sign and generally of similar magnitude as the corresponding native (wild-type) residue that it replaces. Replacement of a cysteine residue by an alanine or methionine residue, e.g., to prevent undesired cyclization or other side reactions of the cysteine residues, is also to be considered a conservative substitution in the context of the peptides of the present invention.

As used herein, the term "nonpolar amino acid residue" (also sometimes referred to as a hydrophobic residue) refers to alanine, valine, leucine, isoleucine, proline, and aromatic residues; the term "aromatic amino acid residue" refers to phenylalanine, tyrosine, and tryptophan; the term "polar amino acid residue" (also sometimes referred to as a hydrophilic residue) refers to polar uncharged residues such as serine, threonine, cysteine, methionine, asparagine and glutamine as well as charged residues, such as the negatively charged (acidic) amino acid residues (aspartic acid and glutamic acid), and the positively charged (basic) amino acid residues (lysine, arginine, and histidine). Glycine is can be included as either a polar or a nonpolar amino acid residue with respect to conservative substitutions. Peptide variants in which one or more lysine residue is substituted into the HCMV gB segment also fall within the scope of the present invention. Such lysine-substituted variants can be useful, for example, for increasing the viral inhibitory activity of the peptides.

Table 1 provides a non-limiting list of some illustrative substitutions in the HCMV-gB sequence segments of the peptides of the present invention. These substitutions provide variants of the HCMV-gB sequence segments that maintain a desired level of herpesvirus infectivity inhibiting activity in the peptides. All substitutions are shown in reference to the corresponding residue numbers of SEQ ID NO: 1. As discussed herein, other substitutions, preferably conservative substitutions, can be made in the HCMV-gB sequence segments, in addition to those shown in Table. 1 (e.g., D-amino acid isomers, lysine substitutions, and the like). Preferably, variants of HCMV-gB sequence segments comprising residues 174-200, 233-263, 264-291, and 297-315 of SEQ ID NO: 1, comprise substitutions that maintain or increase the positive WWIHS score of the segment.

Table 2 shows the Wimley-White Interfacial Hydrophobicity Scale for proteins at membrane interfaces as described by Wimley and White in 1996. This hydrophobicity or hydropathy scale is based on the free energy change required to transfer a peptide residue from a hydrophobic membrane bilayer interface to an aqueous phase. In the scale shown in Table 2, a positive residue free energy ($\Delta G^{residue}$), in kilocalories per mole, indicates a hydrophobic residue (i.e., energy must be added to transfer a hydrophobic residue from a hydrophobic membrane into water). Similarly, a negative free energy indicates a hydrophilic residue.

TABLE 1

Selected Peptide Residue Substitutions.

| Residue Number(s) based on SEQ ID NO: 1 | Substitutions |
|---|---|
| 174-200 | |
| E175 | K, R, H |
| H177 | D, E |
| H178 | D, E |
| K181 | D, E |
| C185 | A, M |
| R191 | D, E |
| 233-263 | |
| H234 | D, E |
| R236 | D, E |
| R243 | D, E |
| E244 | K, R, H |
| C245 | A, M |
| C250 | A, M |
| R258 | D, E |
| K260 | D, E |
| 264-291 | |
| H264 | D, E |
| D272 | K, R, H |
| R285 | D, E |

TABLE 1-continued

Selected Peptide Residue Substitutions.

| Residue Number(s) based on SEQ ID NO: 1 | Substitutions |
|---|---|
| 297-315 | |
| D308 | K, R, H |
| R311 | D, E |
| 476-494 | |
| H476 | D, E |
| Q482 | N |
| Q484 | N |
| D488 | E |

TABLE 2

Free energies of transfer of AcWL-X-LL peptides from bilayer interface to water

| X-residue | pH | $\Delta G_{WLXLL}$ (kcal mol$^{-1}$) | $\Delta G^{residue}$ (kcal mol$^{-1}$) |
|---|---|---|---|
| Ala | 8 | 4.08 ± 0.03 | −0.17 ± 0.06 |
| Ala | 2 | 6.94 ± 0.02 | |
| Arg | 8 | 3.91 ± 0.02 | |
| Arg | 2 | 6.12 ± 0.02 | −0.81 ± 0.11 |
| Asn | 8 | 3.83 ± 0.04 | −0.42 ± 0.06 |
| Asp | 8 | 3.02 ± 0.04 | −1.23 ± 0.07 |
| Asp | 2 | 7.00 ± 0.03 | 0.07 ± 0.11 |
| Cys | 8 | 4.49 ± 0.04 | 0.24 ± 0.06 |
| Gln | 8 | 3.67 ± 0.06 | −0.58 ± 0.08 |
| Glu | 8 | 2.23 ± 0.10 | −2.02 ± 0.11 |
| Glu | 2 | 6.94 ± 0.02 | 0.01 ± 0.15 |
| Gly | 8 | 4.24 ± 0.02 | −0.01 ± 0.05 |
| Gly | 2 | 6.70 ± 0.02 | |
| His | 8 | 4.08 ± 0.02 | −0.17 ±0.06 |
| His | 2 | 5.97 ± 0.12 | −0.96 ± 0.12 |
| Ile | 8 | 4.52 ± 0.03 | 0.31 ± 0.06 |
| Leu | 8 | 4.81 ± 0.02 | 0.56 ± 0.04 |
| Lys | 8 | 3.77 ± 0.11 | |
| Lys | 2 | 5.94 ± 0.11 | −0.99 ± 0.11 |
| Met | 8 | 4.48 ± 0.04 | 0.23 ± 0.06 |
| Phe | 8 | 5.38 ± 0.02 | 1.13 ± 0.05 |
| Pro | 8 | 3.80 ± 0.11 | −0.45 ± 0.12 |
| Ser | 8 | 4.12 ± 0.07 | −0.13 ± 0.08 |
| Ser | 2 | 6.94 ± 0.02 | |
| Thr | 8 | 4.11 ± 0.03 | −0.14 ± 0.06 |
| Thr | 2 | 6.67 ± 0.03 | |
| Trp | 8 | 6.10 ± 0.02 | 1.85 ± 0.06 |
| Tyr | 8 | 5.19 ± 0.04 | 0.94 ± 0.06 |
| Val | 8 | 4.81 ± 0.02 | −0.07 ± 0.05 |

The peptides of the present invention can be derivatized at the N-terminus, the C-terminus, or both. For example, the amino group of the N-terminus can be bonded to an acetyl group, a hydrophobic group (e.g., a lipid such as a $C_3$ to $C_{22}$ carboxyl group such as myristic acid, a $C_3$ to $C_{22}$ alkyl group, a $C_3$ to $C_{22}$ alkylaryl group, an arylalkyl group, a cholesterol group, or an aryl group), a carbobenzoxyl group, a dansyl group, a t-butyloxycarbonyl group, or a macromolecular group (e.g., a poly(ethylene glycol) group, or a carbohydrate group such as a glycosyl group), and/or wherein the carboxyl group at the C-terminus is bonded to an amine (e.g., forming an amido group), a hydrophobic group (e.g., a $C_3$ to $C_{22}$ alkoxy group, a $C_3$ to $C_{22}$ alkylaryloxy group, an arylalkyloxy group, or an aryloxy group), or a macromolecular group. In addition, the peptides of the invention optionally can include one or more non-peptide bonds linking adjacent amino acid residues (e.g., in particularly preferred aspects of this embodiment the non-peptide bond is an imido, ester, hydrazine, semicarbazoide or azo bond) and/or one or more amino acid residue is in the D-isomer configuration.

The peptides of the present invention can include additional amino acid residue sequences (preferably functional sequences) at the N-terminus and/or the C-terminus of the HCMV-gB sequence segment or the variant thereof. For example, the peptides can include a sequence to aid in transport of the peptide across a cell membrane (e.g., a cell penetrating peptide), a sequence to increase in vivo half-life of the peptide, a sequence to aid in isolation of the peptide during manufacture, and/or a sequence to impart any other desirable property to the peptide. Examples of such functional peptide sequences include an arginine-rich sequence such as a polyarginine (e.g., RRRRRRRRR SEQ ID NO: 9) or HIV-tat peptide (e.g., GRKKRRQRRRP, SEQ ID NO: 10) e.g. to enhance cell penetration; a histidine-rich peptide sequence such as a His$_6$-tag peptide e.g. to facilitate peptide isolation; human serum albumin (HSA) e.g. to improve peptide serum stability; a C-terminal alternating Ser-Lys peptide (e.g., ASKSKSKSK, SEQ ID NO: 11) e.g. to enhance solubility; one or more modified amino acid residues such as hydroxyproline; and the like. The peptides of the invention also can include two or more HCMV-gB sequence segments as described herein attached to each other by a linking peptide sequence that differs from a native HCMV gB sequence.

Additionally or alternatively, the peptide, the HCMV-gB sequence segment thereof can be in a cyclic form (e.g., the peptide can be cyclized via a disulfide bond formed between two non-adjacent Cys residues, or the peptide can be cyclized by a peptide bond in a homodetic manner, i.e., an N-terminal-to-C-terminal peptide bond, or in a heterodetic manner, i.e., a C-terminal- or N-terminal-to-internal amino acid side-chain amide bond (e.g., a C-terminal carboxyl-to-Lys side-chain amide bond; an N-terminal amino-to-Asp or Glu side-chain amide bond; a Lys side-chain-to-Asp or Gly side-chain amide bond; and the like).

FIGS. 8, 9, 10, 11 and 12 provide a number of specific, non-limiting examples of peptides of the present invention from the region of residues 146 to 315 of SEQ ID NO: 1, including some peptides that include substitutions (e.g., conservative substitutions) indicated by isolated amino acid residues shown in bold face. Also included are derivatives, with non-gB-derived groups (shown in boldface type), such as N-myristoyl (myristic acid) derivatives, human serum albumin fusion proteins, hydroxyproline derivatives (labeled "P*"), fusion proteins with various transport proteins (the non-gB residues being shown in boldface type), cholesterol ester derivatives, heterodetic cyclic peptide derivatives (labeled "**") which are cyclized by a disulfide bond between the thiol side-chains of two cysteine residues, and poly(ethylene glycol) ester (PEG) derivatives. Homodetic cyclic peptide derivatives (e.g., cyclic versions having a peptide bond between the first and last residue of the sequences shown in FIGS. 8, 9, 10, 11 and 12) are also within the scope of the viral inhibiting peptides of the present invention.

The present invention also provides pharmaceutical compositions useful for treating a herpesvirus infection or outbreak comprising at least one peptide of the invention in combination with a pharmaceutically acceptable carrier, vehicle, or diluent, such as an aqueous buffer at a physiologically acceptable pH (e.g., pH 7 to 8.5), a polymer-based nanoparticle vehicle, a liposome, and the like. The pharmaceutical compositions can be delivered in any suitable dosage form, such as a liquid, gel, solid, cream, or paste dosage form. In one embodiment, the compositions can be adapted to give sustained release of the peptide.

In some embodiments, the pharmaceutical compositions include, but are not limited to, those forms suitable for oral, rectal, nasal, topical, (including buccal and sublingual), transdermal, vaginal, or parenteral (including intramuscular, subcutaneous, and intravenous) administration, in a form suitable for administration by inhalation or insufflation, or injection into amniotic fluid. The compositions can, where appropriate, be conveniently provided in discrete dosage units. The pharmaceutical compositions of the invention can be prepared by any of the methods well known in the pharmaceutical arts. Some preferred modes of administration include intravenous (iv), topical, subcutaneous, and injection into amniotic fluid.

Pharmaceutical formulations suitable for oral administration include capsules, cachets, or tablets, each containing a predetermined amount of one or more of the peptides, as a powder or granules. In another embodiment, the oral composition is a solution, a suspension, or an emulsion. Alternatively, the peptides can be provided as a bolus, electuary, or paste. Tablets and capsules for oral administration can contain conventional excipients such as binding agents, fillers, lubricants, disintegrants, colorants, flavoring agents, preservatives, or wetting agents. The tablets can be coated according to methods well known in the art, if desired. Oral liquid preparations include, for example, aqueous or oily suspensions, solutions, emulsions, syrups, or elixirs. Alternatively, the compositions can be provided as a dry product for constitution with water or another suitable vehicle before use. Such liquid preparations can contain conventional additives such as suspending agents, emulsifying agents, non-aqueous vehicles (which may include edible oils), preservatives, and the like. The additives, excipients, and the like typically will be included in the compositions for oral administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

Pharmaceutical compositions for parenteral administration (e.g. by bolus injection or continuous infusion) or injection into amniotic fluid can be provided in unit dose form in ampoules, pre-filled syringes, small volume infusion, or in multi-dose containers, and preferably include an added preservative. The compositions for parenteral administration can be suspensions, solutions, or emulsions, and can contain excipients such as suspending agents, stabilizing agent, and dispersing agents. Alternatively, the peptides can be provided in powder form, obtained by aseptic isolation of sterile solid or by lyophilization from solution, for constitution with a suitable vehicle, e.g. sterile, pyrogen-free water, before use. The additives, excipients, and the like typically will be included in the compositions for parenteral administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 100 millimolar, preferably at least about 1 nanomolar to about 10 millimolar.

Pharmaceutical compositions for topical administration of the peptides to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like. Such gels can be used, for example, in a personal lubricant composition containing the peptide and optionally including one or more other antiviral agents, for preventing or inhibiting sexual transmission of a herpesvirus infection. In addition, lotions, creams and gels including a peptide of the present invention can be utilized for topical application to a lesion from a herpesvirus outbreak. The additives, excipients, and the like typically will be included in the compositions for topical administration to the epidermis within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

Pharmaceutical compositions suitable for topical administration in the mouth (e.g., buccal or sublingual administration) include lozenges comprising the peptide in a flavored base, such as sucrose, acacia, or tragacanth; pastilles comprising the peptide in an inert base such as gelatin and glycerin or sucrose and acacia; and mouthwashes comprising the active ingredient in a suitable liquid carrier. The pharmaceutical compositions for topical administration in the mouth can include penetration enhancing agents, if desired. The additives, excipients, and the like typically will be included in the compositions of topical oral administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

A pharmaceutical composition suitable for rectal administration comprises a peptide of the present invention in combination with a solid or semisolid (e.g., cream or paste) carrier or vehicle. For example, such rectal compositions can be provided as unit dose suppositories. Suitable carriers or vehicles include cocoa butter and other materials commonly used in the art. The additives, excipients, and the like typically will be included in the compositions of rectal administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

According to one embodiment, pharmaceutical compositions of the present invention suitable for vaginal administration are provided as pessaries, tampons, creams, gels, pastes, foams, or sprays containing a peptide of the invention in combination with a carriers as are known in the art. Alternatively, compositions suitable for vaginal administration can be delivered in a liquid or solid dosage form. The additives, excipients, and the like typically will be included in the compositions of vaginal administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

Pharmaceutical compositions suitable for intra-nasal administration are also encompassed by the present invention. Such intra-nasal compositions comprise a peptide of the invention in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising the peptide. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of the peptide. Alternatively, pharmaceutical compositions for administration by inhalation or insufflation can be provided in the form of a dry powder composition, for example, a powder mix of the peptide and a suitable powder base such as lactose or starch. Such powder composition can be provided in unit dosage form, for example, in capsules, cartridges, gelatin packs, or blister packs, from which the powder can be administered with the aid of an inhalator or insufflator. The additives, excipients, and the like typically will be included in the compositions of intra-nasal administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

Optionally, the pharmaceutical compositions of the present invention can include one or more other therapeutic agent, e.g., as a combination therapy. For example, the composition can include one or more other anti-infective agents in addition to the peptide of the invention, such as, for example, an antiviral protease enzyme inhibitor (PI), a virus DNA or RNA or reverse transcriptase (RT) polymerase inhibitor, another virus/cell fusion inhibitor, a virus integrase enzyme inhibitor, a virus/cell binding inhibitor, a virus or cell helicase enzyme inhibitor, a bacterial cell wall biosynthesis inhibitor, a virus or bacterial attachment inhibitor, an HIV-1 RT inhibitor (such as tenofovir, epivir, zidovudine, or stavudine, and the like), an HIV-1 protease inhibitor (such as saquinavir, ritonavir, nelfinavir, indinavir, amprenavir, lopinavir, atazanavir, tipranavir, fosamprenavir, and the like), an HIV-1 fusion inhibitor (such as enfuvirtide (T20), PRO-542, SCH-C, and the like), a polybiguanide (PBG), a herpes virus DNA polymerase inhibitor (such as acyclovir, ganciclovir, cidofovir, and the like), a herpes virus protease inhibitor, a herpes virus fusion inhibitor, a herpes virus binding inhibitor, a ribonucleotide reductase inhibitor, and the like. The additional therapeutic agent will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with a peptide of the present invention.

In one embodiment, the present invention provides a peptide as described herein for inhibiting herpesvirus infectivity or treating a herpesvirus infection, e.g., an HSV-1, HSV-2, VZV, EBV, or HCMV infection.

In another aspect, the present invention also provides a method for treating, preventing or inhibiting a herpesvirus infection by administering a therapeutically effective amount of at least one peptide of the invention to a subject that has been exposed to a herpesvirus, e.g., an HCMV, HSV-1, HSV-2, EBV, VZV, HHV-6, HHV-7, and KSHV infection. While not being limited thereto, the methods of the present invention can be particularly effective for treating immuno-compromised subjects, e.g., for HCMV infections. In the methods of the present invention, the peptides preferably are administered in the form of a pharmaceutical composition, as described above. The peptides of the present invention will be administered to a subject at a therapeutically useful and effective dosage range, as determined by routine methods that are well known in the medical and pharmaceutical arts. For example, a typical unit dosage will deliver an amount of the peptide in the range of at least about 1 milligram to about 1000 mg, preferably at least about 10 milligrams to about 100 milligrams. The peptide can be administered in a single unit dose, or in multiple unit doses delivered, for example on a per hour, per day, per week, or per month, schedule for a fixed or indefinite period of time. The particular dosage and administration protocol will vary depending on the dosage form, the particular peptide, the type of infection, the severity of the infection, the physical condition of the subject, and other factors that are well known in the medical and pharmaceutical arts.

In one embodiment, the method comprises administering one or more additional therapeutic agent in addition to the peptide of the invention, e.g., as a combination therapy. For example, the peptide of the invention can be administered in combination with one or more other anti-infective agents, such as, for example, an antiviral protease enzyme inhibitor (PI), a virus DNA or RNA or reverse transcriptase (RT) polymerase inhibitor (e.g., foscarnet), another virus/cell fusion inhibitor, a virus integrase enzyme inhibitor, a virus/cell binding inhibitor, a virus or cell helicase enzyme inhibitor, a bacterial cell wall biosynthesis inhibitor, a virus or bacterial attachment inhibitor, an HIV-1 RT inhibitor (such as tenofovir, epivir, zidovudine, or stavudine, and the like), an HIV-1 protease inhibitor (such as saquinavir, ritonavir, nelfinavir, indinavir, amprenavir, lopinavir, atazanavir, tipranavir, fosamprenavir, and the like), an HIV-1 fusion inhibitor (such as enfuvirtide (T20), PRO-542, SCH-C, and the like), a polybiguanide (PBG), a herpes virus DNA polymerase inhibitor (such as acyclovir, ganciclovir, valganciclovir (a prodrug of ganciclovir), cidofovir, and the like), a herpes virus protease inhibitor, a herpes virus fusion inhibitor, a herpes virus binding inhibitor, a ribonucleotide reductase inhibitor, and the like. Some preferred drugs for use in combination therapies with the peptides, pharmaceutical compositions, and methods of the present invention include, without limitation, ganciclovir, valganciclovir, cidofovir, and foscarnet. The dosages for administering the peptides and other therapeutic agents will be determined by factors such as the specific activity of peptide or therapeutic agent, the age and physical condition of the subject to be treated, the type of dosage form, the severity of the herpesvirus infection, the type of herpesvirus infection (e.g., HCMV, HSV-1, HSV-2, EBV, VZV, HHV-6, HHV-7, or KSHV infection), and the like, as is well within the level of ordinary skill of a medical professional. The dosage of the other therapeutic agent can be in the same range as is typical for use of that agent as a monotherapy, or the dosage may be lower than a typical monotherapy dosage if there is a synergy when administered in combination with a peptide of the present invention.

The following Examples are provided to illustrate certain aspects and features of the isolated peptides, pharmaceutical compositions, and methods of the present invention.

EXAMPLE 1

Design and Synthesis of Peptides

Viruses and Cells.

The Towne strain of HCMV containing the Green Fluorescent Protein (GFP) expression cassette was obtained from Dr. Dan Streblow at the Oregon Health Science University and was propagated in human foreskin fibroblast (HFF) cells. Viral supernatants were collected, centrifuged to clear cell debris, and filtered through a 0.45 μm filter. HFF cells were grown in Dulbecco's modified Eagle medium (DMEM) supplemented with 10% fetal bovine serum (FBS), penicillin G (100 U/mL), streptomycin (100 mg/mL), and GLUTAMAX™ L-glutamine supplement (2 mM) from Invitrogen.

As described above, the Wimley White Interfacial Hydrophobicity Scale (WWIHS) identifies segments of proteins that prefer a transbilayer helix conformation to an unfolded interfacial location. WWIHS is an experimentally determined algorithm that can be used to estimate the propensity of amino acid sequence to interact with lipid membrane interface (55). Version 3.0 of the Interface Scale of the MEMBRANE PROTEIN EXPLORER ("MPEx", which is available at the url: blanco(.)biomol(.)uci(.)edu/mpex) computer program was used to identify these particular segments of HCMV gB. The Interface Scale is based on a residue's free energy of transfer within an unfolded polypeptide chain from water to a phosphocholine bilayer. Nine segments of HCMV gB that display high propensity to interact with the lipid surface of cell membrane were identified using the MPEx program. Peptides ranging from 19 to 31 amino acids in length were then designed and prepared to evaluate the ability of such WWIHS-positive sequence to inhibit HCMV infectivity. The synthesized peptides are analogous to the identified WWIHS-positive regions of gB, but with Cys residues replaced by Ala residues to prevent unwanted dimerization (e.g., Cys185, Cys246 and Cys250 were replaced by Ala; numbering based on SEQ ID NO: 1).

The HCMV gB synthetic peptides were synthesized by solid phase conventional N-a-9-flurenylmethyloxycarbonyl (fmoc) chemistry by Genemed Synthesis Inc. (San Francisco, Calif.), and were purified by reverse-phase high performance liquid chromatography. Sequences were confirmed by amino acid analysis and electrospray mass spectrometry. Peptide stock solutions were prepared in 10% dimethyl sulfoxide (DMSO, spectroscopy grade): 90% (v/v) $H_2O$. Peptide concentrations were determined by absorbance of aromatic side chains at 280 nm (SMARTSPEC ™ 3000, from BioRad, Hercules, Calif.).

EXAMPLE 2

Peptide Inhibition of Viral Infection

Human foreskin fibroblasts were seeded at the density of about $3.5 \times 10^5$ cells in each well of a 24-well plate about 24 hours prior to infection. The HFF cells were washed with 1× DPBS, and mock or virus infected for about 90 minutes at room temperature (RT) with the Towne GFP strain of HCMV at about 0.5 multiplicity of infection (MOI), preincubated with a range of concentrations of inhibitory peptides at about 37° C. for about 90 minutes. After the infection, virus mixture was removed and 10% FBS complete DMEM was added to each well and cells were incubated at about 37° C. for about 48 hours. GFP positive cells were visualized about 48 hours post infection by fluorescence microscopy and then quantified using flow cytometry. Results are shown in FIGS. 2A-2D, 3A, and 3B (Panel I of each figure), where significant reductions in the number of GFP positive cells compared to HCMV infected cells are denoted by a *($p<0.05$),  ($p<0.01$), and *($p<0.001$), based on one-way ANOVA and Tukey's post test. Panels II and III of each figure also show ribbon structures of HSV-1 gB in the post-fusion configuration generated using the MACPYMOL (62) and FREEHAND (Macromedia) programs. The HCMV gB trimer is illustrated in the Panels II and III. Peptides targeting different domains of HSV-1 gB that correspond to HCMV gB domains are shown in black and are indicated with arrows in Panels II and III of each figure. HFF cells were trypsinized, centrifuged, and resuspended in 1% FBS-Dulbecco's phosphate buffered saline (DPBS). GFP positive cells were quantified using flow cytometry (CYTOMICS FC 500 from Beckman Coulter, Fullerton, Calif.).

WWIHS was also used to evaluate the sequences of a representative class II viral fusion protein (Dengue virus E) and of class III viral fusion proteins to identify sequences within the proteins that have high potential to interface with lipid membranes (particularly positive hydrophobicity scores) using the MPEx program. The Dengue virus E stem domain sequence has a positive WWIHS scale score and corresponds to a previously determined inhibitor of Dengue virus and West Nile virus (41). A class III domain nomenclature is used herein to refer to both class II and class III viral fusion proteins: i.e., four domains are identified: domain I, domain II, domain III, and domain IV (stem domain). This unified nomenclature assigns domain II [which is known as IV in the VSV G nomenclature of Roche et al. (24), and as I in the HSV-1 gB nomenclature of Heldwein et al. (25) and in Kadlec et al. baculovirus nomenclature (26)] as the class III fusion domain, for consistency with class II viral fusion proteins. In addition to minor adjustments in the ends of domains, the current class III viral fusion protein numbering also combines two interacting domains into domain III (i.e., I+II in Roche's VSV G nomenclature, III+IV in Heldwein's HSV-1 gB nomenclature and Kadlec's baculovirus nomenclature).

In addition to similarities in overall structure, there are also similarities in the distribution of WWIHS-positive sequences. The similarities include at least one extended "fusion loop" in the fusion domain (domain II), and one or more WWIHS score positive sequences in domain III. With the exception of ACNPV gp64, class II and class III fusion proteins contain another WWIHS positive domain II sequence near the "hinge" region adjacent to domain II. Herpesvirus gB proteins have an additional WWIHS-positive sequence in domain I.

Previous studies have shown that gB of various members of the herpesvirus family play important roles in viral entry (30-36). The gB protein is the most highly conserved envelope protein in the herpesvirus family (23, 29), and therefore gB of HCMV is likely to share structural features with gB of other members of the Herpesviridae. The gB of herpesviruses (23, 30, 32), the glycoprotein G of the rhabdoviruses (24), and GP of baculoviruses (37) comprise the third class of viral fusion proteins of enveloped viruses, class III viral fusion proteins or penetrenes (38). Class III viral fusion proteins share certain characteristics found in class I or class II viral fusion proteins. The class III viral fusion proteins contain an extended α-helix that trimerizes in the post-fusion forms of the proteins (39, 40, 24), as has been well-documented for the post-fusion forms of the class I viral fusion proteins of orthomyxoviruses, retroviruses, paramyxoviruses, arenaviruses, and coronaviruses (38). Similarly, the class II viral fusion proteins of flaviviruses and alphaviruses contains a fusion domain comprised principally of β-sheets and "fusion loops." Class III viral fusion proteins also possess a fusion domain, as well as several other features of class II viral fusion proteins, suggested that these two classes of proteins may share a common progenitor.

WWIHS provides a convenient quantitative description of protein partitioning and folding into membrane interfaces. WWIHS score-positive peptide segments may also interact with hydrophobic surfaces within proteins, and are often sequestered within in the pre-fusion forms of viral fusion proteins. In the case of class II and III viral fusion proteins, the fusion loops in the fusion domain often contain sequences with positive WWIHS scores. Previous studies have suggested that synthetic peptides corresponding to or overlapping with sequences in viral fusion proteins that have positive WWIHS scores can sometimes serve as viral entry inhibitors (41-54). For example, enfuvirtide (FUZEON® viral inhibitor from Roche) is a 36 amino acid peptide that overlaps with a WWIHS-positive sequence in the transmembrane protein (TM) of HIV-1. Enfuvirtide is a 36 amino acid peptide that reportedly works by inhibiting the structural rearrangement of HIV-1 gp41 to block the fusion of HIV-1 virion with the target cell membrane. A study done by Brennan-Benson et al., showed that this drug prevents vertical transmission of HIV-1 in pregnancy, but does not cross the placenta (61).

The MPEx computer program was employed to identify regions of the amino acid sequence HCMV gB (SEQ ID NO: 1) that exhibited a positive WWIHS score and thus have a high propensity to interact with the lipid bilayer of cell membranes and potentially may serve as HCMV entry inhibitors. FIG. 1 provides a WWIHS hydropathy plot for HCMV gB generated by the MPEx program. Nine peptides with significant positive WWIHS scores were identified (see the underlined portions of the hydropathy plot shown in FIG. 1). As expected, several of these WWIHS sequences corresponded to the predicted fusion domain of HCMV gB, including the predicted fusion loops.

Peptides corresponding to the sequences with significant positive WWIHS scores were synthesized and examined for their ability to inhibit HCMV infection of HFF cells with herpesvirus (e.g., HCMV). In segments that included one or more Cys residues, the Cys residues were replaced by Ala residues in the synthetic peptides, in order to prevent undesirable dimerization of the peptides. The synthetic peptides are identified herein as "Peptide xxx-yyy" herein, wherein "xxx-yyy" represents the corresponding residues of HCMV gB (with Ala replacing Cys where appropriate, unless otherwise noted).

The first WWIHS score positive sequence identified in HCMV gB was the segment consisting of amino acid residues 146 to 200 of SEQ ID NO: 1 (ΔG score of 4.33 Kcal/mol). For purposes of peptide evaluation, this amino acid segment was split into two smaller portions, i.e., Peptide 146-173 (SEQ ID NO: 2) and Peptide 174-200 (SEQ ID NO: 3). A second large segment within the fusion domain of HCMB gB received a ΔG score of 3.39, and was also split into smaller peptides (i.e., Peptide 233-263 (SEQ ID NO: 4) and Peptide 264-291 (SEQ ID NO: 5)). An additional peptide (Peptide 297-315 (SEQ ID NO: 6)) that corresponds to another fusion domain sequence was also synthesized, along with 4 additional peptides corresponding to other domains of HCMV gB. The regions of SEQ ID NO: 1 identified as having positive WWIHS scores were: residues 146-173, 174-200, 233-263, 264-291, 297-315, each in the fusion domain, as well as residues 415-433, 476-494, 573-591, and 614-632 in other domains of the gB protein. Table 3 provides the amino acid residue sequences (single letter format) for synthetic peptides encompassing the WWIHS-positive segments of the fusion domain of HCMV gB, as well as one peptide from outside domain II (Peptide 476-494, SEQ ID NO: 7), which were prepared for in vitro evaluation against herpesviruses.

TABLE 3

Selected Synthetic Peptides

| Region of SEQ ID NO: 1 | Sequence | SEQ ID NO: |
|---|---|---|
| 146-173 | VLTFRRSYAYIYTTYLLGSNTEYVAPPM | SEQ ID NO: 2 |
| 174-200 | WEIHHINKFAQAYSSYSRVIGGTVFVA | SEQ ID NO: 3 |
| 233-263 | WHSRGSTWLYRETANLNAMLTITTARSKYPY | SEQ ID NO: 4 |
| 264-291 | HFFATSTGDVVYISPFYNGTNRNASYFG | SEQ ID NO: 5 |
| 297-315 | FFIFPNYTIVSDFGRPNAA | SEQ ID NO: 6 |
| 476-494 | HNLVYAQLQFTYDTLRGYI | SEQ ID NO: 7 |

In the sequences shown in Table 3, alanine (A) residues shown in bold-typeface represent substitutions of Ala (A) for a Cys (C) in the native HCMV gB sequence. FIGS. 2A, 2B, 2C and 2D illustrate viral infectivity inhibition data for the peptides of SEQ ID NO: 2, 3, 4 and 5. Panels II and III of each figure show a ribbon structure for HCMV gB trimer with the approximate location of the peptide segment (in black) indicated by arrows. Each Panel II shows a view from the end of the trimer that contacts the cell membrane; while each Panel III shows a side view of the trimer with the end that contacts the cell membrane on the right.

Figure 2B:
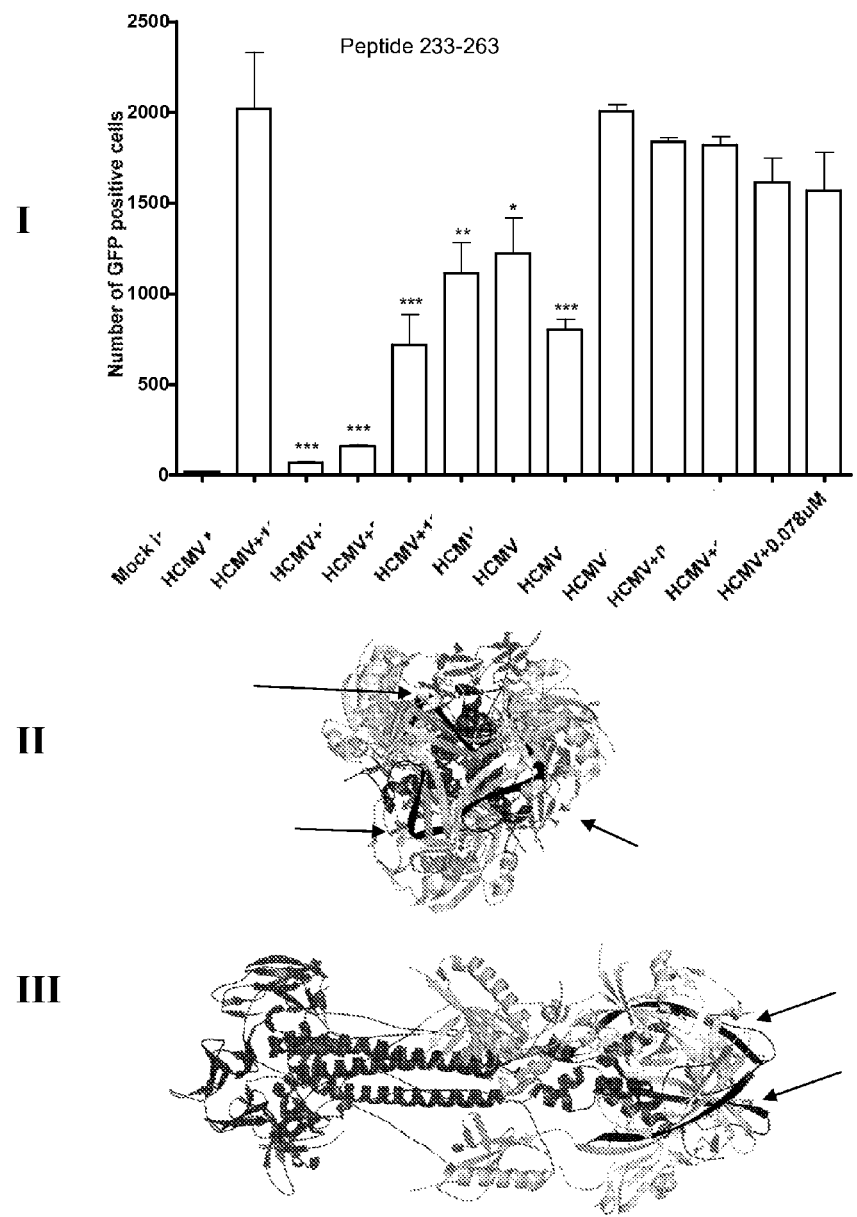
Figure 2C:
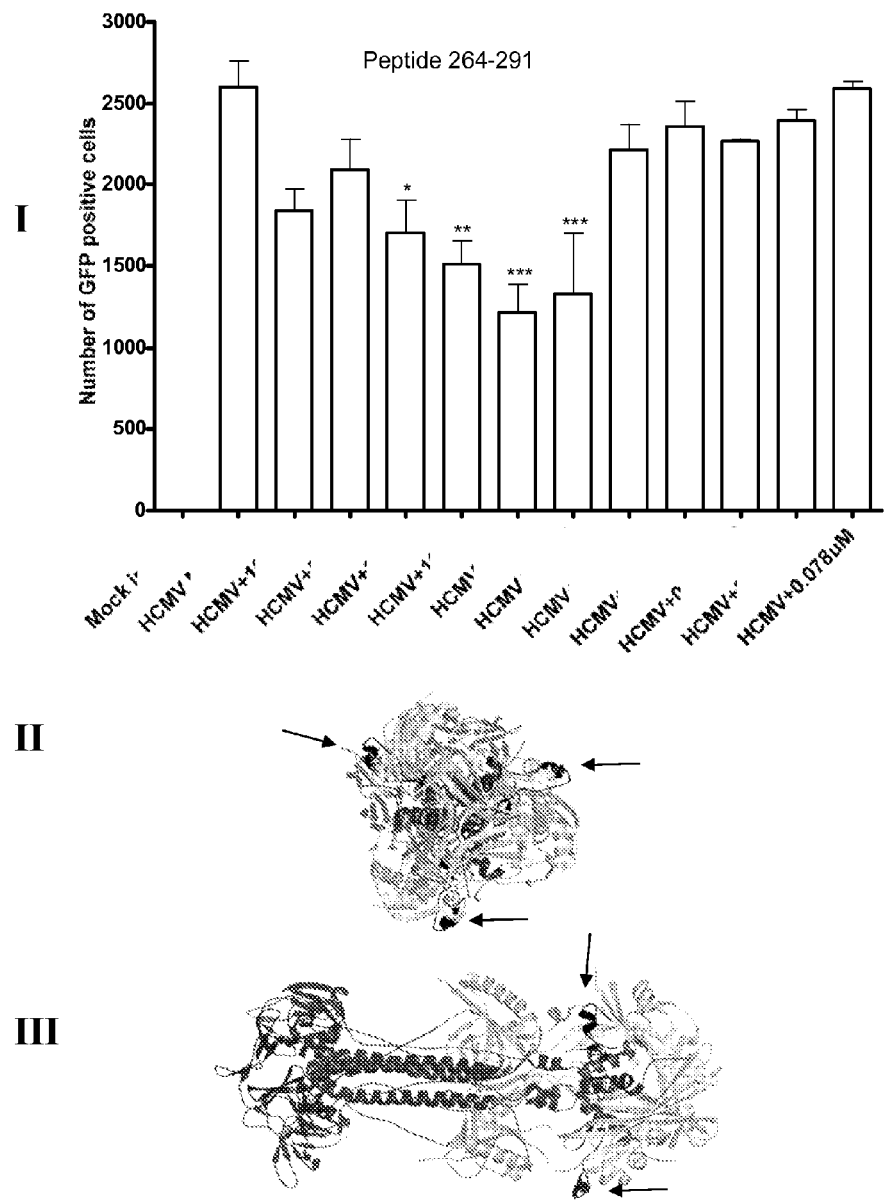
Figure 2D:
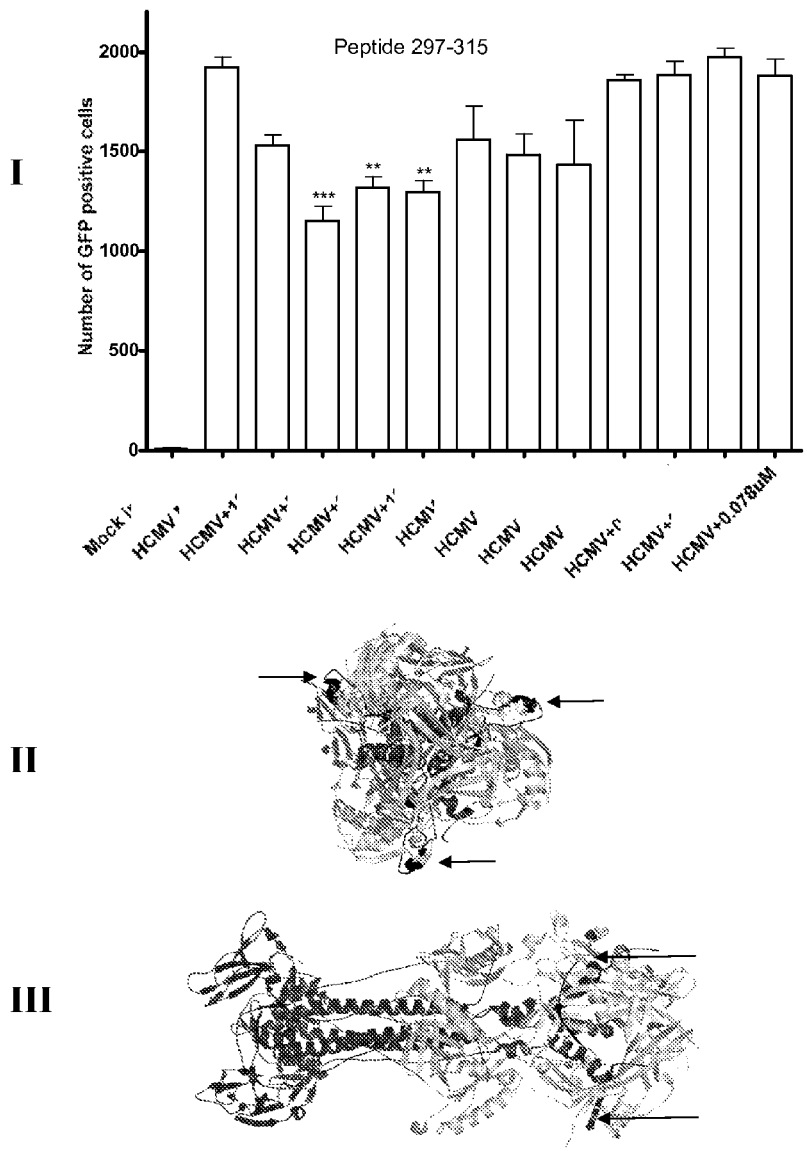

All of the synthetic peptides were tested at the following concentrations: about 100 µM, 50 µM, 25 µM, 10 µM, 5 µM, 2.5 µM, 1.25 µM, 0.625 µM, 0.3125 µM, 0.156 µM, and 0.078 µM. Peptide 174-200 (SEQ ID NO: 3), for instance, exhibited about 80% inhibition of viral infection at the concentration of 100 µM, and about 51% and 62% inhibition at the concentrations of 5 µM and 2.5 µM respectively (FIG. 2A). Peptide 233-263 (SEQ ID NO: 4) displayed about 97% and about 92% inhibitory effect at the concentrations 100 µM and 50 µM, respectively, and about 60% inhibition at the concentration of 2.5 µM (FIG. 2B). Representative fluorescent and bright light images of HFF cells infected with Towne strain of HCMV at the MOI of about 0.5, preincubated with Peptide 233-263 (SEQ ID NO: 4) at the concentration of 100 µM, were taken about 48 hours post-infection (FIG. 4). Panels A-B of FIG. 4 show representative fluorescent and bright light microscopic images, respectively, of the HFF cells infected with Towne GFP strain of HCMV with no peptide present. Panels C-D show representative fluorescent and bright light images of HFF cells infected with Towne strain of HCMV at the MOI of 0.5 preincubated with Peptide 233-263 (SEQ ID NO: 4) at the concentration of 100 µM. The images in FIG. 4 visually demonstrate that the peptide effectively inhibited infection of the cells. While Peptide 264-291 (SEQ ID NO: 5) alone showed inhibition of about 19% to about 70.5%, the latter at the concentration of 5 µM (FIG. 2C), Peptide 297-315 (SEQ ID NO: 6) tested alone showed about 40% inhibition at the concentration of 50 µM (FIG. 2D). None of the remaining WWIHS-positive peptides showed significant inhibition of HCMV infection at any of the concentrations tested (data not shown).

The inhibitory effects of the peptides described above tested alone are not dose-dependent. The success of the inhibition of fusion greatly depends not only on biophysical properties of synthesized peptides and their concentrations, but also on the size and shape of the binding pocket of HCMV gB.

After testing all the synthetic peptides alone, two pairs of peptides were evaluated in combination. FIGS. 3A and 3B illustrate viral infectivity inhibition data for two peptide combinations. Panels II and III of each figure show a ribbon structure for HCMV gB trimer with the approximate location of the peptide segment (in black) indicated by arrows. Each Panel II shows a view from the end of the trimer that contacts the cell membrane; while each Panel III shows a side view of the trimer with the end that contacts the cell membrane on the right. Peptide 174-200 (SEQ ID NO: 3) and Peptide 233-263 (SEQ ID NO: 4), when tested together, provided about 42% inhibition at the concentration of 50 µM each (FIG. 3A), and did not work in a synergistic fashion. This result may be due to peptide-peptide interactions that are not able to interfere with gB trimer formation and necessary conformational changes of the virion that are required for the successful fusion event that involves multiple steps. Peptide concentration is one factor that may affect the ability of two peptides to work in synergy. When the concentration of one or both peptides is too high, the peptides may self-associate and loose their ability to interfere with the putative fusion loops of HCMV gB and inhibit fusion of the HCMV virion with the lipid membrane. In contrast, when the concentrations are too low, the interaction of peptides needed to inhibit infectivity (e.g., the tethering of gB to HSPGs, binding to cellular host cell surface receptors, binding to the lipid interface of the cell membrane, trimerization of gB, or its association with other envelope glycoproteins) may not be achieved, thus resulting in infection.

Surprisingly, synergistic inhibition of infectivity by two peptides was observed in one combination of peptides. As shown in FIG. 3B, the combination of Peptide 264-291 (SEQ ID NO: 5) and Peptide 297-315 (SEQ ID NO: 6) displayed a maximum of about 53% and about 40% inhibition at the concentrations of 5 µM and 50 µM, respectively, while this combination exhibited about 67% inhibition at the concentration of 125 nM each. It is possible that these two peptides block HCMV entry at distinct steps in the fusion process. It is believed that the peptides inhibit virion:cell membrane fusion by interacting with a binding pocket of HCMV gB.

Several drugs, including ganciclovir, its oral prodrug valganciclovir, foscarnet, cidofovir, and fomivirsen have been approved for the treatment of HCMV-associated disease. All of these drugs, with the exception of fomivirsen, have a common target, the viral DNA polymerase (27). The above listed anti-HCMV drugs provoke not only drug-specific side effects, which include leukopenia, thrombocytopenia, anemia, bone marrow hypoplasia, diarrhea, and renal toxicity, but also the emergence of clinically relevant drug-resistant HCMV (28). The peptides of the present invention provide a valuable alternative to these approved drugs. In addition, the peptides of the present invention can be used in combination with these drugs.

The inhibitory peptides of the present invention provide a novel therapeutic against herpesvirus infection, particularly HCMV infection. These antiviral agents can be used as an antiviral treatment to reduce the viral load in pregnant women and neonates. It is not clear how the virus infects the fetus during pregnancy, but some studies demonstrate that placental infection with HCMV occurs before the transmission of the virus to the fetus and suggest the role of placenta in vertical transmission of HCMV from mother to the fetus. Also, placental viral infection was implicated in spontaneous abortion during early pregnancy that occurs in fifteen percent of women with primary HCMV infection (57, 58). Placental pathology resulting from HCMV infection during pregnancy may also cause premature delivery, intrauterine growth restriction (IUGR), or pre-eclampsia (57, 59, 60).

The peptides of the present invention can be used alone or in combination with other already approved therapeutic agents that are used as antiviral regimens in mother-to-child transmission prevention, as well as for the treatment of neonates infected with HCMV. Antiviral agents based on the peptides of the present invention will not require activation by virally encoded proteins, further phosphorylation by cellular enzymes, or incorporation into the growing viral DNA by viral DNA polymerase. Hence, theoretically, they should not provoke drug-specific resistance, which is a significant problem with the existing FDA approved therapeutics to treat HCMV infection, since they employ a different mechanism of action. Additionally, the results of cell viability assays that were performed to test peptide toxicity do not show any statistically significant toxicity due to the treatment of cells with peptides at the highest concentration tested in our studies. Consequently, adverse effects or toxicity due to the treatments using these synthetic peptides are unlikely.

Peptides having amino acid residue sequences spanning amino acid residues 168-186 and 346-360 of human herpesvirus 1 gB (HSV-1 gB, SEQ ID NO: 8), developed by Akkarawongsa and coworkers (56, 73), reportedly inhibit HSV-1 infection. HCMV gB segment 297-315 is analogous to segment 346 to 360 of HSV-1 gB, as illustrated by the ribbon structures for HSV-1 and HCMV shown in FIG. 5. Due to this similarity, peptides of the present invention, particularly a peptide comprising all or a portion of residues 297-315 of SEQ ID NO: 1 or a variant thereof, is expected to have activity to inhibit HSV-1. It is also expected that HCMV gB Peptide 476-494 (SEQ ID NO: 7), which corresponds to the region of overlapping inhibitory peptides in gB94 (residues 496 to 510 of gB94) and gB95 (residues 501-515 of gB95) will inhibit infection by HSV-1. In confirmation, it was observed that even though these peptides were not WWIHS-positive, they were inhibitory against HSV-1. The HCMV gB segment spanning residues 476-494 of HCMV gB (SEQ ID NO: 1), which corresponds to the trimerization domain that contains extended α-helices) does not have a positive WWIHS score. A peptide corresponding to this segment (Peptide 476-494; SEQ ID NO: 7) was tested against HCMV strain Towne-GFP. This peptide did not show any inhibitory activity at high concentrations tested; however, the number of HCMV infected cells decreased as the concentration of this peptide decreased. Since this peptide corresponds to the trimerization domain of HCMV gB, it is possible that, at high concentrations, this particular peptide self-aggregates and is not able to inhibit fusion.

To evaluate the ability of HCMV gB peptides to inhibit infection by HSV-1, Vero cells were plated at a density of about 1.5×10$^5$ cells in each well of a 24 well-plate 24 hours prior to infection. The cells were washed and mock- or virus-infected for about 90 minutes at room temperature with HSV-1 McIntyre strain (ATCC) of about 0.001 MOI preincubated with a range of concentrations of four different synthetic peptides at about 37° C. for about 90 minutes. After exposure to the virus, the virus mixture was removed and the cells were overlayed with 2% FBS MEM containing 1% methylcellulose. Cells were incubated for about 48 hours at about 37° C. After about 48 hours, the cells were fixed, stained with Crystal Violet, and air dried. FIG. 6 shows images of the stained cells.

In FIG. 6, each treatment was done in triplicate, where A=media, B=HSV-1 MOI of 0.001, C=100 µM peptide and virus, D=50 µM peptide and virus, E=25 µM peptide and virus, F=10 µM peptide and virus, G=5 µM peptide and virus, H=2.5 µM peptide and virus. HCMV gB Peptide 174-200 (SEQ ID NO: 3), Peptide 233-263 (SEQ ID NO: 4), and Peptide 264-291 (SEQ ID NO: 5), which correspond to portions of domain II of HCMV gB, each inhibited HSV-1 infection. Peptide 476-494 (SEQ ID NO: 7) corresponds to the trimerization domain of HCMV gB, which contains extended α-helices important in the formation of HCMV gB homotrimer during fusion of HCMV virion and lipid membrane of the host cell. Overlapping inhibitory HSV-1 peptides that span regions 496-510 and 501-515 of the HSV-1 gB protein (SEQ ID NO: 8) are analogous to HCMV gB peptide 476-494 (SEQ ID NO: 7). As predicted, HCMV Peptide 476-494 (SEQ ID NO: 7) worked best at the concentration of about 2.5 µM.

EXAMPLE 3

Inhibition of HCMV Strain TRpMIA

In order to assess the ability of the peptides of the present invention to inhibit a clinically significant HCMV (HCMV TRpMIA), Peptide 174-200 (SEQ ID NO:3), Peptide 233-263 (SEQ ID NO: 4), and Peptide 264-291 (SEQ ID NO: 5), were tested for inhibition of HCMV TRpMIA infection of HFF cells under the assay conditions similar to these described in Example 2 for the Towne strain of HCMV, above. In particular, HFF cells were plated in 96-well plates at a density of about 10,000 cells-per-well about 24 hours post infection. Individual inhibitory peptides were evaluated against 0.5 MOI HCMV TRpMIA preincubated with various concentrations in the range of about 0.078 micromolar to about 100 micromolar. The results obtained from these assays are shown in FIG. 13, FIG. 14, and FIG. 15 for Peptide 174-200, Peptide 233-263, and Peptide 264-291, respectively. The degree of HCMV infection was determined by evaluating the number of cells expressing immediate-early 1 (IE-1) or IE-2 HCMV proteins 24 hours post-infection. Treatments resulting in significant reductions in the number of cells that were positive for IE 1, IE-2, or both, compared to non-treated control HCMV infected cells, are denoted by a *(p<0.05),  (p<0.01), and *(p<0.001, one-way ANOVA and Tukey's post test). Variants and derivatives of Peptide 233-263 (SEQ ID NO: 4) also were prepared and tested in the same assay. The sequences of the tested variants and derivatives are shown in Table 4, with additions or modifications from SEQ ID NO: 4 shown in boldface type.

TABLE 4

Variants and Derivatives of Peptide 233-263

| Peptide No. | Sequence | SEQ ID NO: |
|---|---|---|
| 233-263.1 | KDQWHSRGSTWLYRETANLNAMLTITTARSKYPY | SEQ ID NO: 143 |
| 233-263.2 | VTVKDQWHSRGSTWLYRETANLNAMLTITTARSKYPY | SEQ ID NO: 144 |
| 233-263.3 | WHSRGSTWLYRETANLNAMLTITTARSKYPYHFF | SEQ ID NO: 145 |
| 233-263.4 | KDQWHSRGSTWLYRETANLNAMLTITTARSKYPYHFFATS | SEQ ID NO: 146 |
| 233-263.5 | WHSRGSTWLYRAETANLNAMLTITTARSKYPY | SEQ ID NO: 147 |
| 233-263.6 | WHSRGSTWLYRETANLNAMLTITTARSKYPYP | SEQ ID NO: 148 |
| 233-263.7 | WHSRGSTWLYRETANLNAMLTITTARSKYPYG | SEQ ID NO: 149 |
| 233-263.8 | WHSRGSTWLYRETANLNAMLTITTARSKYPYGRKKRRQRRRP | SEQ ID NO: 67 |
| 233-263.9 | WHSRGSTWLYRETANLNAMLTITTARSKYPYRRRRRRRRR | SEQ ID NO: 68 |

As is evident in Table 4, Peptide 233-263.1 comprises SEQ ID NO: 4 with residues 230-232 of SEQ ID NO: 1 added at the N-terminus; Peptide 233-263.2 comprises SEQ ID NO: 4 with residues 227-232 of SEQ ID NO: 1 added at the N-terminus; Peptide 233-263.3 comprises SEQ ID NO: 4 with residues 264-266 of SEQ ID NO: 1 added at the C-terminus; Peptide 233-263.4 comprises SEQ ID NO: 4 with residues 230-232 of SEQ ID NO: 1 added at the N-terminus and residues 264-269 of SEQ ID NO: 1 added at the C-terminus; Peptide 233-263.5 comprises SEQ ID NO: 4 with residue Glu12 replaced by Ala; Peptide 233-263.6 comprises SEQ ID NO: 4 with a Pro residue added at the C-terminus; Peptide 233-263.7 comprises SEQ ID NO: 4 with a Gly residue added at the C-terminus; Peptide 233-263.8 comprises SEQ ID NO: 4 with the sequence GRKKRRQRRRP (SEQ ID NO: 10) added at the C-terminus; and Peptide 233-263.9 comprises SEQ ID NO: 4 with the sequence RRRRRRRRR (SEQ ID NO: 9) added at the C-terminus.

The data in FIG. 13 demonstrate that Peptide 174-200 exhibited significant inhibition of infection at concentrations of 25 micromolar (**, $p<0.01$ confidence level), 50 micromolar (*, $p<0.05$ confidence level), and 100 micromolar (***, $p<0.001$ confidence level).

The data in FIG. 14 demonstrate that Peptide 233-263 exhibited significant inhibition of infection at concentrations of 5 micromolar (*, $p<0.05$ confidence level), 10 micromolar (*, $p<0.001$ confidence level), 25 micromolar (*, $p<0.001$ confidence level), 50 micromolar (*, $p<0.001$ confidence level), and 100 micromolar (*, $p<0.001$ confidence level), with almost complete inhibition at 50 to 100 micromolar.

The data in FIG. 15 demonstrate that Peptide 264-291 exhibited significant inhibition of infection at concentrations of 50 micromolar (*, $p<0.05$ confidence level), and 100 micromolar (*, $p<0.05$ confidence level).

The data in FIG. 16, obtained with Peptide 233-263.9 demonstrate that this modified version of Peptide 233-263 surprisingly exhibited highly significant, and almost complete inhibition of infection at concentrations of 25 micromolar to 100 micromolar (***, $p<0.001$ confidence level), which is a significant improvement over the results obtained with Peptide 233-263, shown in FIG. 14.

Peptides 233-263.1, 233-263.2, 233-263.3, 233-263.4, 233-263.5, 233-263.6, 233-263.1.8, each were less effective at inhibiting infection by HCMV TRpMIA compared to Peptide 233-263, although each peptide did exhibit some level of inhibition relative to the controls.

Toxicity assays run on solutions of the peptides in DMSO indicated that the DMSO solvent may have had some negative effect on the viability of the HFF cells during the 24 hour preincubation period.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

References Incorporated Herein

1. Crough T, Khanna R: Immunobiology of Human Cytomegalovirus: from Bench to Bedside. *Clinical Microbiology Reviews* 2009, 76-98.
2. Kenneson A, Cannon M J: Review and meta-analysis of the epidemiology of congenital cytomegalovirus (CMV) infection. *Rev. Med. Virol.* 2007, 17:253-276.
3. Stagno S, Pass R F, Cloud G, Britt W J, Henderson R E, Walton P D, Veren D A, Page F, Alford C A: Primary cytomegalovirus infection in pregnancy. Incidence, transmission to fetus, and clinical outcome. *JAMA* 1986, 256:1904-1908.
4. Gandhi M K, Khanna R: Human cytomegalovirus: clinical aspects, immune regulation, and emerging treatments. *Lancet Infect. Dis.* 2004, 4:725-738.
5. Davison A J, Dolan A, Akter P, Addison C, Dargan D J, Alcendor D J, McGeoch D J, Hayward G S: The human cytomegalovirus genome revisited: comparison with the chimpanzee cytomegalovirus genome. *Anal. Biochem.* 1987, 162:156-159.
6. Mocarski E S Jr, Shank T, Pass R F: Cytomegaloviruses. In: *Fields Virology*. Edited by Knipe D M, Howley P M, Griffin D E, Lamb R A, Martin M A, Roizman B, Straus S E 2007, 2: 2701-2772.
7. Varnum S M, Streblow D N, Monroe M E, Smith P, Auberry K J, Pasa-Tolic L, Wang D, Camp D G, 2nd, Rodland K, Wiley S, Britt W, Shenk T, Smith R D, Nelson J A: Identification of proteins in human cytomegalovirus (HCMV) particles: the HCMV proteome. *J. Virol.* 2004, 78:10960-10966.
8. Lopper M, Compton T: Disulfide bond configuration of human cytomegalovirus glycoprotein B. *J. Virol.* 2002, 76:6073-6082.
9. Wang X, Huong S-M, Chin M L, Raab-Traub N, Huang E S: Epidermal growth factor receptor is a cellular receptor for human cytomegalovirus. *Nature* 2003, 424:456-461.
10. Soroceanu L, Akhavan A, Cobbs C: Platelet-derived growth factor-α receptor activation is required for human cytomegalovirus infection. *Nature* 2008, 455:391-396.
11. Compton T, Kurt-Jones E A, Boehme K W, Belko J, Latz E, Golenbock D T, Finberg R W: Human cytomegalovirus activates inflammatory cytokine responses via CD14 and Toll-like receptor 2. *J. Virol.* 2003, 77:4588-4596.
12. Wang X, Huang D Y, Huong S M, Huang E S: Integrin αvβ3 is a coreceptor for human cytomegalovirus. *Nature Medicine* 2005, 11:515-521.
13. Li J, Lin M L, Wiepz G J, Guadarrama A G, Bertics P J: Integrin-mediated migration of murine B82L fibroblasts is dependent on the expression of an intact epidermal growth factor receptor. *J. Biol. Chem.* 1999, 274:11209 11219.
14. Miyamoto S, Teramoto H, Gutkind J S, Yamada K M: Integrins can collaborate with growth factors for phosphorylation of receptor tyrosine kinases and MAP kinase activation: roles of integrin aggregation and occupancy of receptors. *J. Cell. Biol.* 1996, 135:1633-1642.
15. Schneller M, Vuori K, Ruoslahti E: Alphavbeta3 integrin associated with activated insulin and PDGFbeta receptors and potentiates the biological activity of PDGF. *EMBO* 1997, 16:5600-5607.
16. Bold S, Ohkin M, Garten W, Radsak K: Structural domains involved in human cytomegalovirus glycoprotein B-mediated cell-cell fusion. *J. Gen. Virol.* 1996, 77 (Pt 9): 2297-2302.

17. Keay S, Baldwin B: Anti-idiotype antibodies that mimic gp86 of human cytomegalovirus inhibit viral fusion but not attachment. *J. Virol.* 1991, 65: 5124-5128.
18. Navarro D, Paz P, Tugizov S, Topp K, La Vail J, Pereira L: Glycoprotein B of human cytomegalovirus promotes virion penetration into cells, transmission of infection from cell to cell, and fusion of infected cells. *Virology* 1993, 197: 143-158.
19. Tugizov S, Wang Y, Qadri I, Navarro D, Maidji E, Pereira L: Mutated forms of human cytomegalovirus glycoprotein B are impaired in inducing syncytium formation. *Virology* 1995, 209: 580-591.
20. Sinzger C, Jahn G: Human cytomegalovirus cell tropism and pathogenesis. *Intervirology* 1996, 39: 302-319.
21. Stoddart C A, Cardin R D, Boname J M, Manning W C, Abenes G B, Mocarski E S: Peripheral blood mononuclear phagocytes mediate dissemination of murine cytomegalovirus. *J. Virol.* 1994, 68: 6243-6253.
22. Gicklhorn D, Eickmann M, Meyer G, Ohlin M, Radsak K: Differential effects of glycoprotein B epitope-specific antibodies on human cytomegalovirus-induced cell-cell fusion. *J. Gen. Virol.* 2003, 84: 1859-1862.
23. Isaacson M K, Compton T: Human cytomegalovirus glycoprotein B is required for virus entry and cell-to-cell spread, but not for virion attachment, assembly, or egress. *J. Virol.* 2009, 83: 3891-3903.
24. Roche S, Bressanelli S., Rey F. A., Gaudin Y: Crystal structure of the low-pH form of the vesicular stomatitis virus glycoprotein G. *Science* 2006, 313 (5784): 187-191.
25. Heldwein E E, Lou H, Bender F C, Cohen G H, Eisenberg R J, Harrison S C: Crystal structure of glycoprotein B from herpes simplex virus I. *Science* 2006, 313 (5784): 217-220.
26. Kandlec J, Loureiro S, Abrescia N G A, Stuart D I, Jones I: The postfusion structure of baculovirus gp64 supports a unified view of viral fusion machines. *Nat. Struct. Mol. Biol.* 2008, 15:1024-1030.
27. Andrei G, De Clercq E, Snoeck R: Novel inhibitors of human CMV. *Current Opinion in Investigational Drugs* 2008, 9: 132-145.
28. Michel D, Mertens T: Antiviral intervention, resistance and perspectives. In: *Cytomegaloviruses Molecular biology and immunology*. Edited by Reddehase M, Caister Academic Press 2006, 573-590.
29. Cranage M P, Kousarides T, Bankier A T, Satchwell S, Weston K, Tomlinson P, Barrel B, Nart H, Bell S E, Minson A C, Smith G L: Identification of the human cytomegalovirus glycoprotein B gene and induction of neutralizing antibodies via its expression in recombinant vaccinia virus. *EMBO* 1986, 5: 3057-3063.
30. Cheshenko N, Herold B C: Glycoprotein B plays a predominant role in mediating herpes simplex virus type 2 attachment and is required for entry and cell-cell spread. *J. Gen. Virol.* 2002, 83: 2247-2255.
31. Dunn W, Chou C, Li H, Hai R, Patterson D, Stolc V, Zhu H, Liu F: Functional profiling of a human cytomegalovirus genome. *Proc. Natl. Acad. Sci. USA* 2003, 100: 14223-14228.
32. Herrold R E, Marchini A, Fruehling S, Longnecker R: Glycoprotein 110, the Epstein-Barr virus homolog of herpes simplex virus glycoprotein B are involved in Epstein-Barr virus replication in vivo. *J. Virol.* 1996, 70: 2049-2054.
33. Hobom U, Brune W, Messerle M, Hahn G, Koszinowski U H: Fast screening procedures for random transposon libraries of cloned herpesvirus genomes: mutational analysis of human cytomegalovirus envelope glycoprotein genes. *J. Virol.* 2000, 74: 7720-7729.
34. Krishnan H H, Sharma-Walia N, Zeng L, Gao S J, Chandran B: Envelope glycoprotein gB of Kaposi's sarcoma-associated herpesvirus is essential for egress from infected cells. *J. Virol.* 2005, 79: 10952-10967.
35. Schaffer P A, Aron G M, Biswal N, Benyesh-Melnick M: Temperature-sensitive mutants of herpes simplex virus type 1: isolation, complementation and partial characterization. *Virology* 1973, 52: 57-71.
36. Schaffer P A, Carter V C, Timbury M C: Collaborative complementation study of temperature-sensitive mutants of herpes simplex virus types 1 and 2. *J. Virol.* 1978, 27: 490-504.
37. Blissard G W, Wenz J R: Baculovirus gp64 envelope glycoprotein is sufficient to mediate pH-dependent membrane fusion. *J. Virol.* 1992, 66 (11): 6829-6835.
38. Garry E G, Garry R F: Proteomics computational analyses suggest that baculovirus GP64 superfamily proteins are class III penetrenes. *Virol. J.* 2008, 5: 28.
39. Heldwein E E, Lou H, Bender F C, Cohen G H, Eisenberg R J, Harrison S C: Crystal structure of glycoprotein B from herpes simplex virus I. *Science* 2006, 313 (5784): 217-220.
40. Roche S, Rey F A, Gaudin Y, Bressanelli S: Structure of the prefusion form of the vesicular stomatitis virus glycoprotein G. *Science* 2007, 315 (5813): 843-848.
41. Hrobowski Y M, Garry R F, Michael S F: Peptide inhibitors of dengue virus and west Nile virus infectivity. *Virol. J.* 2006, 2: 49-59.
42. Sainz Jr. B, Mossel E C, Gallaher W R, Wimley W C, Peters C J, Wilson R B, Garry R F: Inhibition of severe acute respiratory syndrome-associated coronavirus (SARS-CoV) infectivity by peptides analogous to the viral spike protein. *Virus Research* 2006, 120: 146-155.
43. FDA notifications. FDA approves Fuzeon, the first fusion inhibitor. *AIDS Alert* 2003, 18 (6): 78-79.
44. Gallaher W R, Garry R F: Model of the pre-insertion region of the spike (S2) fusion glycoprotein of the human SARS coronavirus: implications for antiviral therapeutics. web publication at url www.virology.net/Articles/sars/s2model.html, May 1, 2003.
45. Gallaher W R, Segrest J P, Hunter, E: Are fusion peptides really "sided" insertional helices? *Cell* 1992, 70(4): 531-532.
46. Lambert D M, Barney S, Lambert A L, Guthrie K, Medinas R, Davis D E, Bucy T, Erickson J, Merutka G, Petteway Jr. S R: Peptides from conserved regions of paramyxovirus fusion (F) proteins are potent inhibitors of viral fusion. *Proc. Natl. Acad. Sci. USA* 1996, 93 (5): 2186-2191.
47. Owens R J, Tanner C C, Mulligan M J, Srinivas R V, Compans R W: Oligopeptide inhibitors of HIV-induced syncytium formation. *AIDS Res. Hum. Retroviruses* 1990, 6 (11): 1289-1296.
48. Qureshi N M, Coy D H, Garry R F, Henderson L A: Characterization of a putative cellular receptor for HIV-1 transmembrane glycoprotein using synthetic peptides. *AIDS* 1990, 4(6): 553-558.
49. Richardson C D, Scheid A, Choppin P W: Specific inhibition of paramyxovirus and myxovirus replication by oligopeptides with amino acid sequences similar to those at the N-terminal of the F1 or HA1 viral polypeptides. *Virology* 1980, 105 (1): 205-222.
50. Silburn K A, McPhee D A, Maerz A L, Poumbourios P, Whittaker R G, Kirkpatrick A, Reilly W G, Manthey M K, Curtain C C: Efficacy of fusion peptide homologs in blocking cell lysis and HIV-induced fusion. *AIDS Res. Hum. Retroviruses* 1998, 14 (5): 385-392.

51. Watanabe S, Takada A, Watanabe T, Ito H, Kida H, Kawaoka Y: Functional importance of the coiled-coil of the Ebola virus glycoprotein. *J. Virol.* 2000, 74 (21): 10194-10201.
52. Wild C, Greenwell T, Matthews T: A synthetic peptide from HIV-1 gp31 is a potent inhibitor of virus-mediated cell-cell fusion. *AIDS Res. Hum. Retroviruses* 1993, 9 (11): 1051-1053.
53. Wild C, Oas T, McDanal C, Bolognesi D, Matthews T: A synthetic peptide inhibitor of human immunodeficiency virus replication: correlation between solution structure and viral inhibition. *Proc. Nat. Acad. Sci. USA* 1992, 89 (21): 10537-10541.
54. Young J K, Li D, Abramowitz M C, Morrison T G: Interaction of peptides with sequences from the Newcastle disease virus fusion protein heptad repeat regions. *J. Virol.* 1999, 73 (7): 5945-5956.
55. Wimley W C, White S H: Experimentally determined hydrophobicity scale for proteins at membrane interfaces. *Nat. Struct. Biol.* 1996, 3 (10): 842-848.
56. Akkarawongsa R, Pocaro N E, Case G, Kolb A W, Brandt C R: Multiple peptides homologous to Herpes Simplex Virus Type 1 glycoprotein B inhibit viral infection. *Antimicrob. Agents and Chemotherapy* 2009, 53 (3): 987-996.
57. Fisher S, Genbacev O, Maidji E, Pereira L: Human cytomegalovirus infection of placental cytotrophoblasts in vitro and in utero: implications for transmission and pathogenesis. *J. Virol.* 2000, 74(15): 6808-6820.
58. Mostoufi-Zadeh M, Driscoll S G, Biano S A, Kundsin R B: Placental evidence of cytomegalovirus infection of the fetus and neonate. *Arch. Pathol. Lab. Med.* 1984, 108(5): 403-406.
59. von Dadelszen P, and Magee L A: Could an infectious trigger explain the differential maternal response to shared placental pathology of preeclampsia and normotensive intrauterine growth restriction? *Acta. Obstet. Gynecol. Scand.* 2002, 81: 642-648.
60. Istas A S, Demmler G J, Dobbins J D, Stewart J A: Surveillance for congenital cytomegalovirus disease: a report from the National Congenital Cytomegalovirus Disease Registry. *Clin. Infect. Dis.* 1995, 20(3): 665-670.
61. Brennan-Benson P, Pakianathan M, Rice P, Bonora S, Chakraborty R, Charland M: Enfuvirtide prevents vertical transmission of multidrug-resistant HIV-1 in pregnancy but does not cross placenta. *AIDS* 2006, 20(2): 297-299.
62. DeLano W L: The PyMOL Molecular Graphics System. 2002.

We claim:

1. An isolated peptide comprising an HCMV-gB sequence segment bonded to an additional peptide sequence at the N-terminus or C-terminus thereof, wherein the peptide comprises the peptide of SEQ ID NO: 67.

2. A pharmaceutical composition for treating, preventing, or inhibiting a herpesvirus infection comprising the peptide of claim 1 in combination with a pharmaceutically acceptable carrier, vehicle, or diluent.

* * * * *